United States Patent [19]

Pfifner et al.

[11] Patent Number: 5,583,249
[45] Date of Patent: Dec. 10, 1996

[54] PESTICIDES

[75] Inventors: Albert Pfifner, Bülach, Switzerland; Stephen Trah, Freiburg, Germany

[73] Assignee: Ciba-Geigy Corporation, Tarrytown, N.Y.

[21] Appl. No.: 460,175

[22] Filed: Jun. 2, 1995

[30] Foreign Application Priority Data

Aug. 19, 1994 [CH] Switzerland .............................. 2553/94

[51] Int. Cl.$^6$ .......................... C07C 229/36; C07C 69/76
[52] U.S. Cl. ................................. 560/35; 560/60
[58] Field of Search ................................. 560/39, 60, 35

[56] References Cited

U.S. PATENT DOCUMENTS

| | | | |
|---|---|---|---|
| 5,194,662 | 3/1993 | Brand et al. | 560/35 |
| 5,292,759 | 3/1994 | Brand et al. | 514/339 |
| 5,387,607 | 2/1995 | Brand et al. | 514/513 |

FOREIGN PATENT DOCUMENTS

| | | |
|---|---|---|
| 91/78167 | 12/1991 | Australia . |
| 0370629 | 5/1990 | European Pat. Off. . |
| 0403618 | 12/1990 | European Pat. Off. . |
| 0414173 | 2/1991 | European Pat. Off. . |
| 0506149 | 9/1992 | European Pat. Off. . |
| 0585751 | 3/1994 | European Pat. Off. . |
| 95/17376 | 6/1995 | WIPO . |

Primary Examiner—Joseph Conrad
Attorney, Agent, or Firm—Edward McC. Roberts

[57] ABSTRACT

Compounds of formula I are suitable for controlling and preventing infestation by microorganisms, insects and acarina on plants

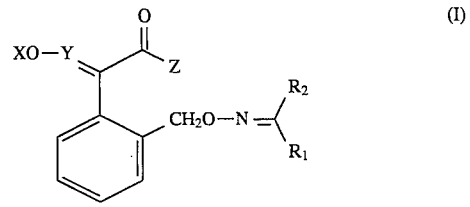

and their possible isomers and mixtures of isomers, wherein a) X is $CH_2F$ or $CHF_2$,
   Y is CH and
   Z is $OCH_3$, or
b) X is $CH_2F$ or $CHF_2$,
   Y is a nitrogen atom and
   Z is $OCH_3$ or $NHCH_3$, and wherein $R_1$ and $R_2$ are each independently of the other hydrogen, cyano, $C_1$–$C_{12}$alkyl, halo-$C_1$–$C_{12}$alkyl, $C_2$–$C_{12}$alkenyl, $C_2$–$C_{12}$alkynyl, $C_3$–$C_6$cycloalkyl, cyclopropylmethyl, $C_1$–$C_4$alkoxy, $C_2$–$C_{12}$alkoxyalkyl, $C_1$–$C_4$alkoxycarbonyl, $C_1$–$C_4$alkylthio, $C_2$–$C_5$alkylthioalkyl; or an unsubstituted or mono- to tri-substituted ring having not more than 15 ring carbon atoms that may be multi-membered and that contains from 0 to 3 hetero atoms N, O or S, it being possible for that ring to be bonded via an aliphatic bridge having not more than 4 carbon atoms and/or via CO, oxygen or sulfur, as desired; or wherein $R_1$ and $R_2$ together with their common carbon atom form an unsubstituted or mono- to tri-substituted ring having not more than 15 ring carbon atoms that may be multi-membered and that contains from 0 to 3 hetero atoms N, O or S.

They can be used in the form of commercially customary formulated compositions.

2 Claims, No Drawings

PESTICIDES

The present invention relates to oxime ethers of the general formula I

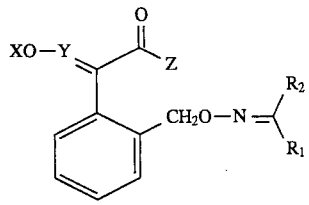

and to their possible isomers and mixtures of isomers, wherein a) X is $CH_2F$ or $CHF_2$,
   Y is CH and
   Z is $OCH_3$, or b) X is $CH_2F$ or $CHF_2$,
   Y is a nitrogen atom and
   Z is $OCH_3$ or $NHCH_3$, and wherein $R_1$ and $R_2$ are each independently of the other hydrogen, cyano, $C_1$–$C_{12}$alkyl, halo-$C_1$–$C_{12}$alkyl, $C_2$–$C_{12}$alkenyl, $C_2$–$C_{12}$alkynyl, $C_3$–$C_6$cycloalkyl, cyclopropylmethyl, $C_1$–$C_4$alkoxy, $C_2$–$C_{12}$alkoxyalkyl, $C_1$–$C_4$alkoxycarbonyl, $C_1$–$C_4$alkylthio, $C_2$–$C_5$alkylthioalkyl; or an unsubstituted or mono- to tri-substituted ring having not more than 15 ring carbon atoms that may be multi-membered and that contains from 0 to 3 hereto atoms N, O or S, it being possible for that ring to be bonded via an aliphatic bridge having not more than 4 carbon atoms and/or via CO, oxygen or sulfur, as desired; or wherein $R_1$ and $R_2$ together with their common carbon atom form an unsubstituted or mono- to tri-substituted ring having not more than 15 ring carbon atoms that may be multi-membered and that contains from 0 to 3 hetero atoms N, O or S;

the possible substituents of all the rings mentioned for $R_1$ and $R_2$, individually or in combination, being selected from $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$alkylcarbonyl, $C_1$–$C_4$alkoxycarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl; phenyl, benzyl, phenoxy, phenylthio, benzyloxy and benzylthio; wherein the last-mentioned aromatic substituents may carry in the phenyl ring not more than five further substituents selected from halogen, $C_1$–$C_4$alkyl, $C_1$–$C_4$alkoxy, $C_1$–$C_4$haloalkyl, $C_1$–$C_4$haloalkoxy, CN and $NO_2$, and wherein two of the not more than five substituents in adjacent positions may form an aliphatic bridge having not more than 5 members that contains from 0 to 2 oxygen atoms and 0 or 1 carbonyl group and that may be substituted not more than four times by halogen, $C_1$–$C_4$alkyl, $C_1$–$C_4$alkoxy and/or by a single phenyl group; or $R_2$ is a group

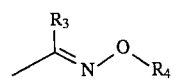

wherein
$R_3$ is hydrogen; $C_1$–$C_6$alkyl; $C_3$–$C_6$cycloalkyl; phenyl that is unsubstituted or mono- or di-substituted by identical or different substituents selected from halogen, $C_1$–$C_4$alkyl, $C_1$–$C_4$alkoxy, $C_1$–$C_2$haloalkyl, $C_1$–$C_2$haloalkoxy, $C_3$–$C_6$alkenyloxy, $C_3$–$C_6$alkynyloxy, $C_1$–$C_4$alkylenedioxy, cyano and nitro; or is thienyl; and $R_4$ is hydrogen; $C_1$–$C_6$alkyl; $C_1$–$C_6$haloalkyl having from 1 to 15 halogen atoms; $C_1$–$C_4$alkoxy-$C_1$–$C_2$alkyl; $C_2$–$C_4$alkenyl-$C_1$–$C_2$alkyl that is unsubstituted or substituted by from 1 to 3 halogen atoms; $C_2$–$C_4$alkynyl-$C_1$–$C_2$alkyl; $C_3$–$C_6$cycloalkyl that is unsubstituted or substituted by from 1 to 4 halogen atoms; $C_3$–$C_6$cycloalkyl-$C_1$–$C_4$alkyl that is unsubstituted or substituted by from 1 to 4 halogen atoms: cyano-$C_1$–$C_4$alkyl; $C_1$–$C_4$alkoxycarbonyl-$C_1$–$C_4$alkyl; phenyl-$C_1$–$C_3$alkyl that is unsubstituted or substituted by halogen, $C_1$–$C_3$alkyl, $C_1$–$C_4$alkoxy, $C_1$–$C_4$haloalkyl, cyano, nitro or by $C_1$–$C_4$alkylenedioxy, wherein the phenyl group may be mono- to tri-substituted by identical or different substituents; phenyl that is unsubstituted or mono- or di-substituted by identical or different substituents selected from $C_1$–$C_4$alkyl, $C_1$–$C_4$alkoxy, halogen, $C_1$–$C_2$haloalkyl having from 1 to 3 halogen atoms, nitro and cyano; or is pyridyl that is unsubstituted or mono- or di-substituted by identical or different substituents selected from $C_1$–$C_4$alkyl, $C_1$–$C_4$alkoxy, halogen, $C_1$–$C_2$haloalkyl having from 1 to 3 halogen atoms, nitro and cyano.

The present invention relates also to compounds of formula I wherein X, Y and Z are as defined above and wherein $R_1$ and $R_2$ are each independently of the other hydrogen, cyano, $C_1$–$C_4$alkyl, halo-$C_1$–$C_4$alkyl, $C_2$–$C_4$alkenyl, $C_2$–$C_4$alkynyl, $C_3$–$C_6$cycloalkyl, cyclopropylmethyl, $C_1$–$C_4$alkoxy, $C_2$–$C_5$alkoxyalkyl, $C_1$–$C_4$alkoxycarbonyl, $C_1$–$C_4$alkylthio, $C_2$–$C_5$alkylthioalkyl, or an unsubstituted or mono- to tri-substituted ring having not more than 15 ring carbon atoms that may be multi-membered and that contains from 0 to 3 hereto atoms N, O or S, it being possible for that ring to be bonded via an aliphatic bridge having not more than 4 carbon atoms and/or via CO, oxygen or sulfur, as desired; or wherein $R_1$ and $R_2$ together with their common carbon atom form an unsubstituted or mono- to tri-substituted ring having not more than 15 ring carbon atoms that may be multi-membered and that contains from 0 to 3 hereto atoms N, O or S; the possible substituents of the rings mentioned for $R_1$ and $R_2$, individually or in combination, being as defined above.

When asymmetric carbon atoms are present in the compounds of formula I, then the compounds occur in optically active form. Purely on the basis of the presence of double bonds, the compounds will in any case occur in the [E]- and/or [Z]-form. Atropisomerism may also occur. Formula I is intended to include all those possible isomeric forms, as well as mixtures thereof, for example racemic mixtures and tiny [E/Z] mixtures.

The compounds according to the invention have fungicidal, insecticidal and acaricidal properties and are suitable as active ingredients in plant protection. The fungicidal action is especially pronounced.

Compounds I having at least one basic centre are capable of forming acid addition salts. Those salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$–$C_4$alkanecarboxylic acids, for example acetic acid, saturated or unsaturated dicarboxylic acids, for example oxalic, malonic, maleic, fumaric or phthalic acid, hydroxycarboxylic acids, for example ascorbic, lactic, malic, tartaric or citric acid, or benzoic acid, or with organic sulfonic acids, such its unsubstituted or substituted, for example halo-substituted, $C_1$–$C_4$alkane- or aryl-sulfonic acids, for example methane- or p-toluenesulfonic acid. In view of the close relationship between the compounds I in free form and in the form of their salts, any reference hereinbefore or hereinafter to the compounds I or their salts is to be understood as including also the corresponding stilts or free compounds I, respectively, where appropriate and expedient.

The general terms used hereinbefore and hereinafter have the meanings given below, unless otherwise defined.

Alkyl groups on their own or as a structural element of other groups are straight-chained or branched, depending upon the number of carbon atoms; for example, $C_1$–$C_{12}$alkyl is methyl, ethyl, propyl, isopropyl, butyl, isobutyl, sec-butyl, tert-butyl, pentyl, hexyl, heptyl, octyl, isooctyl, nonyl, decyl and dodecyl.

Alkenyl as a group or as a structural element of other groups and compounds, such as alkenyloxy, arylalkenyl and heteroarylalkenyl, is either straight-chained or branched, depending upon the number of carbon atoms. $C_1$–$C_{12}$alkenyl is, for example, ethenyl, propen-1-yl or but-1-en-1-yl, propen-2-yl, but-1-en-2-yl, penten-1-yl, penten-3-yl, hexen-1-yl, 4-methyl-3-pentenyl, 4-methyl-3-hexenyl, 4-methyl-3-heptenyl, 4,6-dimethyl-3-heptenyl, nona-3,7-dienyl or 4,8-dimethyl-3,7-nonadienyl.

Alkynyl as a group or as a structural element of other groups and compounds, such as alkynyloxy, is either straight-chained, for example ethynyl, propyn-1-yl or but-1-yn-1-yl, or branched, for example propyn-2-yl or but-1-yn-2-yl.

Cycloalkyl as a group or as a structural element of other groups and compounds, such as cycloalkylmethoxy, is, for example, cyclopropyl, cyclobutyl, cyclopentyl or cyclohexyl.

Carbocyclic rings on their own or as a structural element of other groups, such as aryl-$C_1$–$C_4$alkyl, aryloxy-$C_1$–$C_4$alkyl, arylthio-$C_1$–$C_4$alkyl, arylcarbonyl and aryl-$C_2$–$C_4$alkenyl groups, have especially from 6 to 14 carbon atoms and are, for example, naphthyl, tetrahydronaphthyl, indanyl, fluorenyl, phenanthryl or, especially, phenyl. They may be aromatic, partially hydrogenated or completely saturated. One or two benzene rings may be condensed onto the carbocyclic ring.

Rings containing hetero atoms, as groups by themselves and as structural elements of other groups and compounds, such as heteroaryl-$C_1$–$C_4$alkyl, heteroaryloxy-$C_1$–$C_4$alkyl, heteroarylthio-$C_1$–$C_4$alkyl, heteroarylcarbonyl and heteroaryl-$C_2$–$C_4$-alkenyl groups, have especially from 5 to 14 ring members, of which from 1 to 3 members are hetero atoms selected from the group oxygen, sulfur and nitrogen. There may be mentioned, for example, benzimidazolyl, benzocumarinyl, benzofuryl, benzothiadiazolyl, benzothiazolyl, benzothienyl, benzoxazolyl, benzoxadiazolyl, quinazolinyl, quinolyl, quinoxalinyl, carbazolyl, dihydrobenzofuryl, ethylenedioxyphenyl, furyl, imidazolyl, indazolyl, indolyl, isoquinolyl, isothiazolyl, isoxazolyl, methylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]pyridyl, pyridyl, pyrimidinyl, pyrrolyl, tetrazolyl, thiadiazolyl, thiazolyl, thienyl, triazinyl and triazolyl.

Preferred heteroaryl radicals $R_1$ and/or $R_2$ are benzofuryl, benzothienyl, quinolyl, quinoxalinyl, dihydrobenzofuryl, ethylenedioxy, furyl, methylenedioxy, pyridyl, pyrimidinyl, pyrrolyl, thiazolyl and thienyl.

One or two benzene rings may be condensed onto heterocyclic rings.

Halogen is fluorine, chlorine, bromine or iodine. Examples of haloalkyl and haloalkoxy groups are —$CH_2F$, —$CHF_2$, —$CF_3$, —$CH_2Cl$, —$CHCl_2$, —$CHCl_2$, —$CCl_3$, —$CCl_2CCl_3$, —$CH_2Br$, —$CH_2CH_2Br$, —$CHBrCl$, —$OCHF_2$, $OCF_3$, $OCH_2CF_3$, $OCF_2CHF_2$ and $OCF_2CHFCF_3$.

An especially preferred group of compounds of formula 1 is formed by compounds wherein X is $CH_2F$.

One of the preferred groups of formula I comprises those compounds wherein $R_1$=H, $C_1$–$C_4$alkyl, cyclopropyl, $C_1$–$C_2$alkoxy, $C_1$–$C_2$alkylthio, methoxymethyl, cyano or trifluoromethyl; and $R_2$=halophenyl having from 1 to 3 halogen atoms, mono-$C_1$–$C_2$alkylphenyl, mono-$C_1$–$C_4$alkoxyphenyl, 3-halo-$C_1$–$C_4$alkylphenyl having from 1 to 3 halogen atoms, fluorine- or chlorine-substituted trifluoromethylphenyl, 3-halo-$C_1$–$C_4$alkoxyphenyl having from 1 up to and including 6 halogen atoms (especially fluorine), 3-$C_2$–$C_4$alkenyloxyphenyl, 3-$C_2$–$C_4$alkynyloxyphenyl, 3-$C_3$–$C_6$cycloalkylmethoxyphenyl, 3-cyano-$C_1$–$C_3$alkoxyphenyl, bis(trifluoromethyl)phenyl, fluorine- or chlorine-substituted tolyl, monocyanophenyl, methylthio-substituted trifluoromethylphenyl, 3-trimethylsilylphenyl, methoxynitrophenyl, 3- or 4-phenoxyphenyl, unsubstituted or methoxy-substituted 3-methylsulfinyl- or 3-methylsulfonyl-methylphenyl, 3-trifluoromethyl-4-chlorobenzyl, 3-trifluoromethyl-phenoxymethyl, 3-trifluoromethyl-benzoyl, 2-naphthyl, phenyl substituted in the 3- and 4-positions by straight-chained $C_1$–$C_3$alkylenedioxy (especially methylenedioxy, ethylenedioxy, 2,2-difluoromethylenedioxy, 2-methoxymethylenedioxy), dihydrobenzofur-5-yl, 2-thienyl, benzofur-2-yl, 2-furyl, 5-chloro- or 5-bromo-thien-2-yl, 3-methylbenzo[b]thien-2-yl, 1-methylpyrrol-2-yl, 2-thiazolyl, unsubstituted or halo- or trifluoromethyl-substituted 2-pyridyl, 6- or 7-quinolinyl, 6-quinoxalinyl, 2-pyrimidinyl mono- or di-substituted by halogen, methyl, trifluoromethyl, cyclopropyl, $C_1$–$C_3$alkoxy or by methylthio, or is 1-(2,6-dimethylmorpholinyl);

or $R_1$ and $R_2$ together form a 5,6-dihydro-2H-1,4-thiazine ring substituted in the 3-position by substituted phenyl, or $R_1$ and $R_2$ together form a cyclopentane or tetrahydropyran ring to which an unsubstituted or halo-substituted benzene ring is condensed.

That group is to be designated sub-group IA.

Within the scope of group IA, preference is given to those compounds wherein the substituents have the following meanings:

$R_1$=H, $C_1$–$C_2$alkyl, cyclopropyl, methoxy, methylthio, methoxymethyl, cyano or trifluoromethyl;

$R_2$=monohalo-phenyl, dihalo-phenyl, mono-$C_1$–$C_2$alkylphenyl, mono-$C_1$–$C_2$alkoxyphenyl, 2-naphthyl, 3,4-methylenedioxyphenyl, 3,4-ethylenedioxyphenyl, 2,2-difluoro-5-benzodioxolyl, 2-methoxy-5-benzodioxolyl, 3-(fluoro-$C_1$–$C_2$alkoxy)phenyl having from 1 to 3 fluorine atoms, 3-trifluoromethylphenyl, 3,5-bis(trifluoromethyl)phenyl, 4-fluoro-3-trifluoromethylphenyl, 3-fluoro-5-trifluoromethylphenyl, 4-chloro-3-trifluoromethylphenyl, 4-chloro-3-tolyl, monocyanophenyl, 3-(cyanomethoxy)phenyl, 2-methylthio-5'-trifluoromethylphenyl, 4-methoxy-3-nitrophenyl, 3- or 4-phenoxyphenyl, 3-methylsulfinylmethyl-4-methoxyphenyl, 3-methylsulfonyl-4-methoxy-phenyl, 3-prop-1-en-3-yloxyphenyl, 3-prop-1-yn-3-yloxyphenyl, 3-cyclopropylmethoxyphenyl, 2,3-dihydrobenzofur-5-yl, 3-trifluoromethyl-4-chlorobenzyl, 3-trifluoromethyl-phenoxymethyl, 2-pyridyl, 6-bromo-2-pyridyl, 4-trifluoromethyl-2-pyridyl, 6- or 7-quinolinyl, 6-quinoxalinyl, 2-thienyl, 5-chloro- or 5-bromo-thien-2-yl, 3-methylbenzo[b]thien-2-yl, 2-furyl, benzo[b]-fur-2-yl, 1-methylpyrrol-2-yl, 2-thiazolyl or 1-(2,6-dimethylmorpholinyl); or $R_1$ and $R_2$ together form a 5,6-dihydro-2H-1,4-thiazine ring substituted in the 3-position by mono- or di-halophenyl, methoxyphenyl, trifluoromethylphenyl, phenoxy or by 3,4-methylenedioxyphenyl, or $R_1$ and $R_2$ together form a cyclopentane or tetrahydropyran ring to which an unsubstituted or fluorine-substituted benzene ring is condensed. This group is to be designated sub-group IB.

Within that group, preference is given to compounds wherein the substituents have the following meanings:
$R_1$=methyl, methoxy, ethyl, methylthio or cyclopropyl;
$R_2$=3-halophenyl, 4-halophenyl, 3-trifluoromethylphenyl, 3-haloethoxyphenyl, 4-fluoro-3-trifluoromethoxyphenyl, 4-tolyl, 3,4-methylenedioxyphenyl or 3,4-ethylenedioxyphenyl (compound group IC).

A special group within the scope of formula I comprises compounds wherein the substituents have the following meanings:
$R_1$=methyl or cyclopropyl;
$R_2$=3-chlorophenyl, 3-trifluoromethylphenyl, 3-trifluoromethoxyphenyl or 4-chlorophenyl (sub-group ID).

A preferred group comprises those compounds of formula I wherein
X=monofluoromethyl, Y=CH and Z=methoxy, wherein
$R_1$ is hydrogen, cyano, methyl, ethyl, $CF_3$ or cyclopropyl and $R_2$ is a group

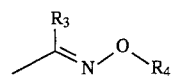

wherein
$R_3$ is $C_1-C_2$alkyl or is phenyl that may be mono- or di-substituted by halogen, $C_1-C_4$alkyl, $C_1-C_4$alkoxy or by $C_3-C_4$alkenyloxy, and
$R_4$ is $C_1-C_4$alkyl, $C_1-C_4$haloalkyl having up to 3 halogen atoms, $C_3-C_4$alkenyl or $C_3-C_4$-alkynyl (sub-group IE).

A further preferred group comprises those compounds of formula I wherein
X=monofluoromethyl, Y=CH and Z=methoxy, wherein
$R_1$ is methyl, ethyl, $CF_3$ or cyclopropyl and
$R_2$ is a phenyl group that is substituted by one or more of the substituents $C_1-C_4$alkyl, $C_1-C_4$alkoxy, $CF_3$, $OCF_3$, $OCHF_2$, halogen or $C_1-C_2$alkylenedioxy or to which a furazan ring is condensed (sub-group IF).

The invention relates also to a process for the preparation of the compounds according to the invention, to fungicidal compositions comprising such compounds as active ingredients, and to the use of such compounds and compositions in the control of phytopathogenic fungi and in the prevention of fungus infestation.

The oxime ethers of the general formula I

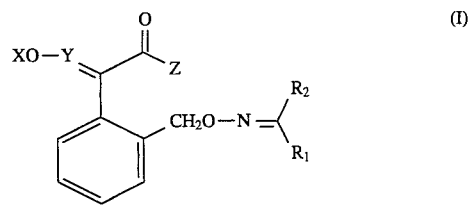

can be prepared in accordance with Scheme 1 below, or in accordance with Scheme 2, or in accordance with Scheme 3.

Scheme 1

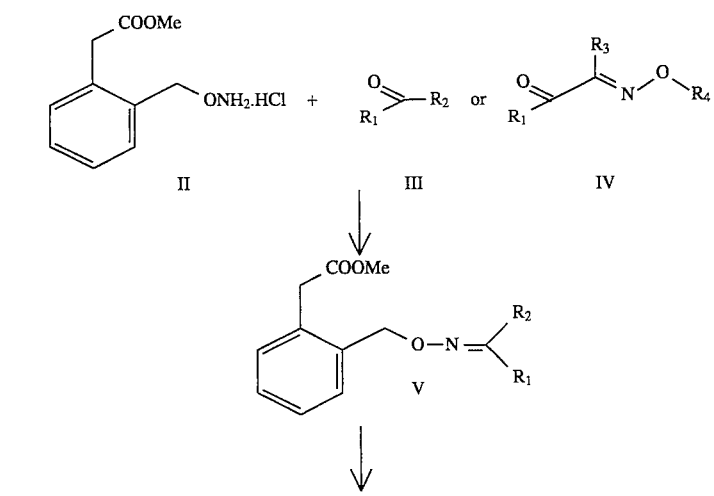

-continued
Scheme 1
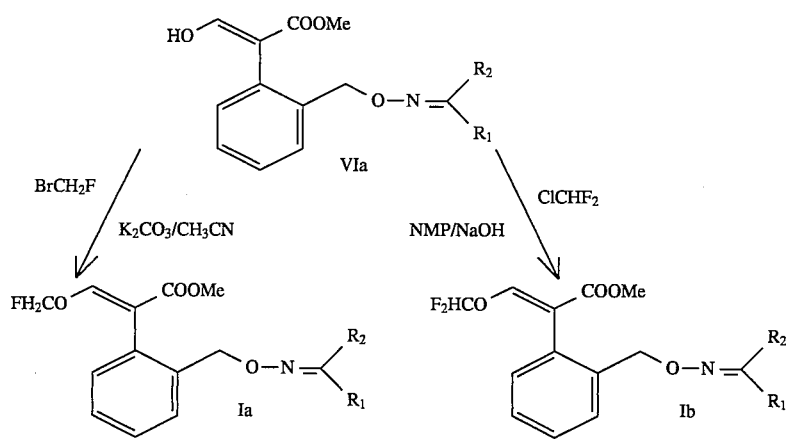
[NMP = N-methylpyrrolidone]
Scheme 2
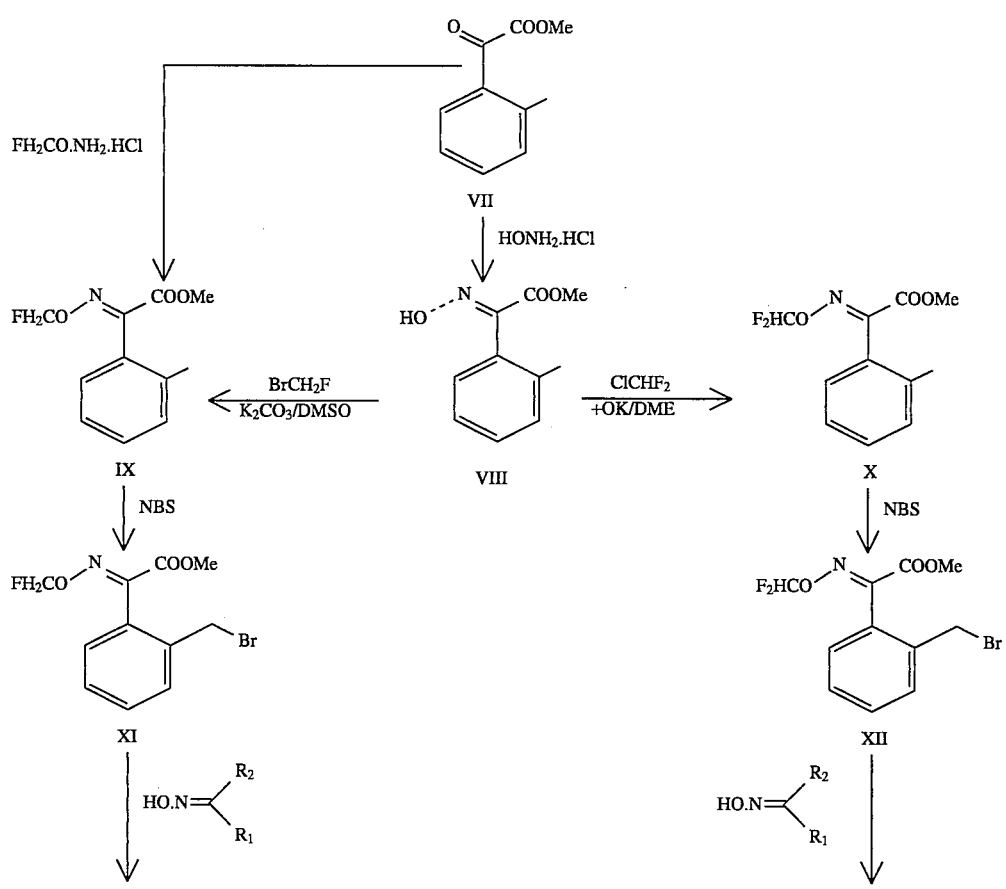

9
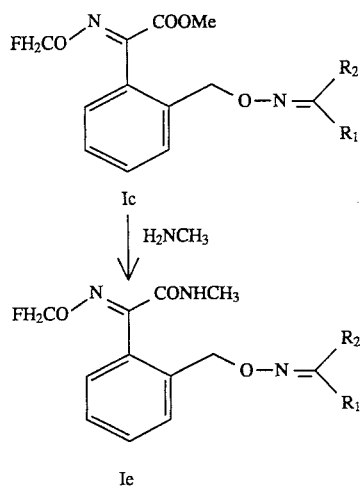
Ic
10
-continued
Scheme 2
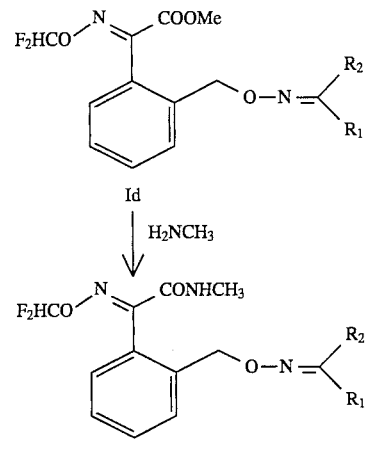
Id
[DMSO = dimethyl sulfoxide, +OK = potassium tert-butoxide, DME = dimethoxyethane, NBS = N-bromosuccinimide]
Scheme 3
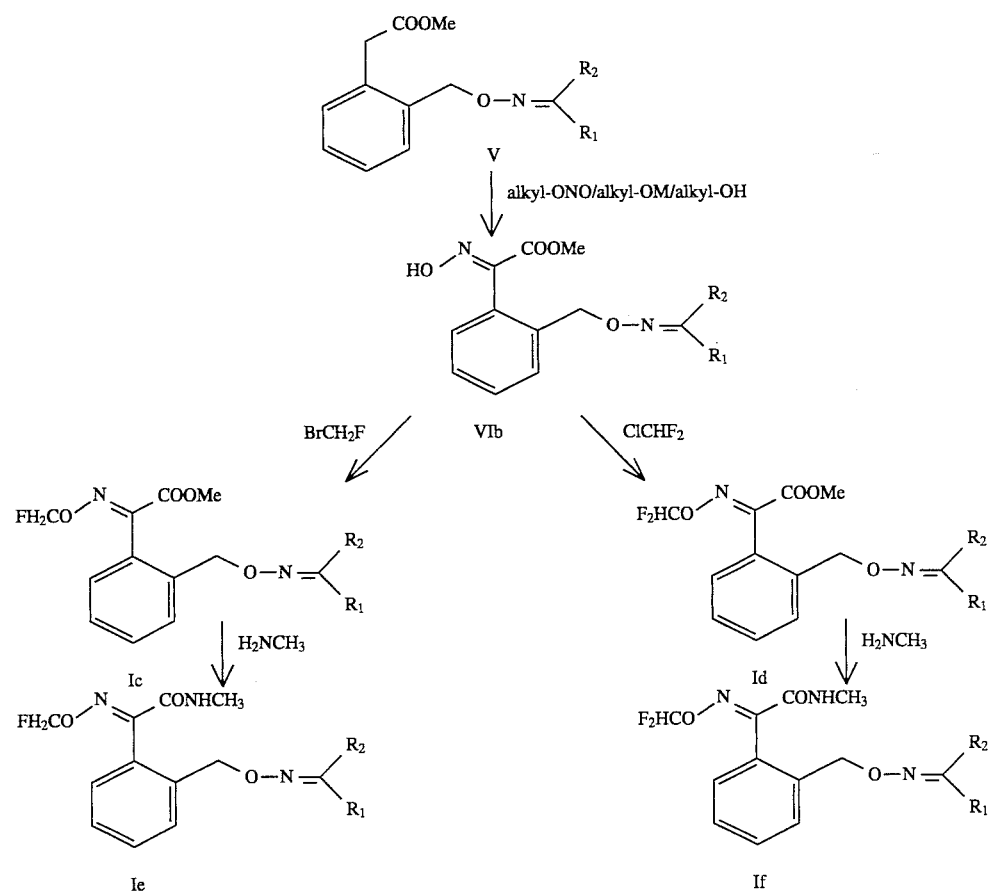

The process for the preparation of compounds of formula I comprises a) where Y=CH, etherifying an oxime ether of formula VIa

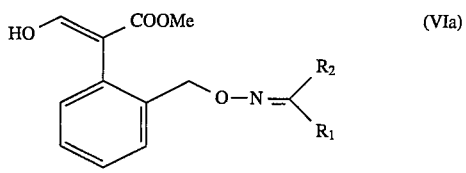

by bromofluoromethane or chlorodifluoromethane in an alkaline medium, or b) where Y=N, etherifying an oxime ether of formula VIb

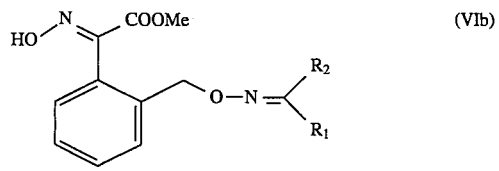

by bromofluoromethane or chlorodifluoromethane, and, if desired, converting the methylcarboxylate group into the N-methylcarboxamide group by treatment with methylamine.

The process for the preparation of compounds of formula I wherein Y is N comprises monobrominating or monochlorinating in the methyl side chain an oximinoglyoxalic acid methyl ester of formula IX or X

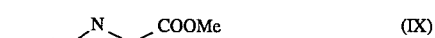

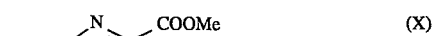

that has been etherified by bromofluoromethane or chlorodifluoromethane, and reacting the halomethyl derivative so obtained with an oximino compound of the formula

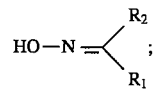

and, if desired, converting the methyl ester side chain into the N-methylcarboxamide group by treatment with methylamine.

Scheme 4 (for the preparation of intermediates)

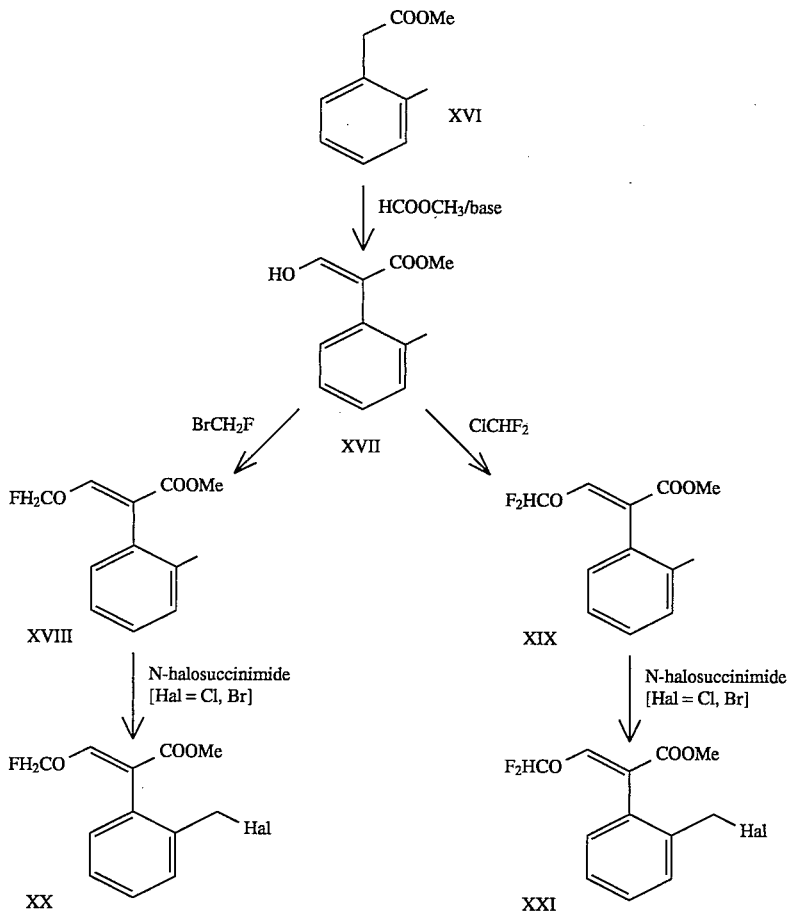

The invention relates also to the intermediates of the formula

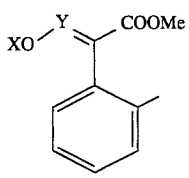

wherein X is CH$_2$F or CHF$_2$ and Y is CH or N, as well as to the intermediates of the formula

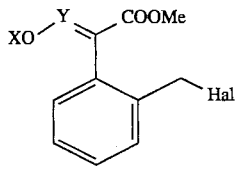

wherein X is CH$_2$F or CHF$_2$, Y is CH or N and Hal is chlorine or bromine.

The compounds of formula II can be prepared in accordance with Scheme 5 below.

Scheme 5

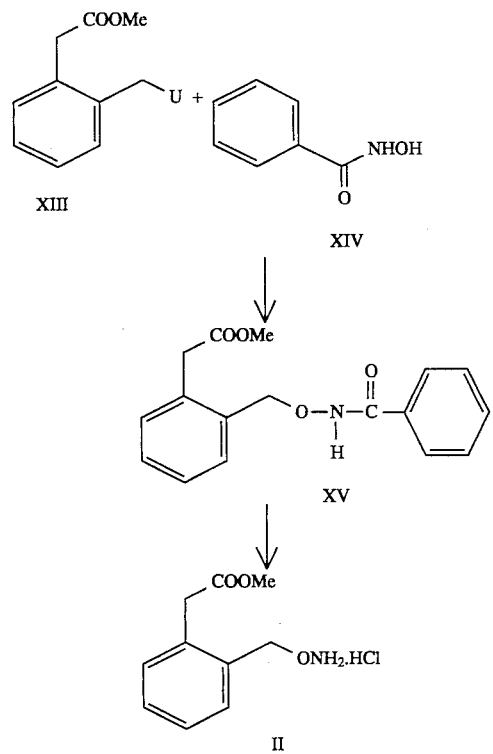

wherein U is a nucleofugal leaving group.

Reaction of a substituted o-tolylacetic acid ester XIII with a benzoylhydroxylamine XIV results in the benzoylated 2-aminooxymethylenephenylacetic acid ester XV which, after acid saponification (=hydrolysis), yields the compound of formula II. Suitable nucleofugal leaving groups U are halides, for example chloride, bromide and iodide, and also benzensulfonate, toluenesulfonate, methanesulfonate, triflate or acetate. Bromide is especially preferred.

The compound of formula II so obtained, whether it be in base form or in the form of a salt, can be converted by reaction with aldehydes or ketones into the corresponding aldimino or ketimino derivatives of formula V, from which compounds of formula VIa or VIb are obtained by formic acid methyl ester condensation or by nitrosation.

Treatment of the compounds of formulae VIa and VIb with BrCH$_2$F yields the compounds of formulae Ia and Ic according to the invention, while treatment with ClCHF$_2$ yields compounds of formulae Ib and Id.

In order to obtain compounds of formulae Ie and If, the compounds of formulae Ic and Id are reacted with methylamine in known manner.

The starting materials XIII and XIV are either known or can be prepared according to known methods (see, for example, Org. Synth. Coll., Vol. II, 67 and J. Amer. Chem. Soc. 31, 3759 (1966)).

Important compounds are the bromides of formulae XI and XII. They can be prepared from the known o-tolylglyoxalic acid methyl ester oxime VIII by reaction with BrCH$_2$F or ClCHF$_2$ in the presence of a base and subsequent bromination with N-bromosuccinimide in boiling carbon tetrachloride.

It has now been found that compounds of formula I, which differ from benzyloxime ethers of the literature inter alia by the novel structural element FH$_2$C—O— or F$_2$HC—O—, have, for practical requirements, a very advantageous microbicidal spectrum in the control of phytopathogenic microorganisms, especially fungi. Compounds of formula I have very advantageous curative, preventive and, in particular, systemic properties, and can be used in the protection of numerous cultivated plants. With the compounds of formula I it is possible to inhibit or destroy the pests which occur on plants or on parts of plants (the fruit, blossom, leaves, stems, tubers, roots) in different crops of useful plants, while at the same time parts of plants which grow later are also protected from phytopathogenic microorganisms.

The compounds of formula I can also be used as dressing agents for protecting seed (fruit, tubers, grains) and plant cuttings against fungus infections as well as against phytopathogenic fungi which occur in the soil.

Compounds of formula I are effective, for example, against the phytopathogenic fungi belonging to the following classes: *Fungi imperfecti* (e.g. Botrytis, also Pyricularia, Helminthosporium, Fusarium, Septoria, Cercospora, Cercosporella and Alternaria); Basidiomycetes (e.g. Rhizoctonia, Hemileia, Puccinia). They are also effective against the class of the Ascomycetes (e.g. Venturia and Erysiphe, Podosphaera, Monilinia, Uncinula), but especially against the class of the Oomycetes (e.g. Phytophthora, Peronospora, Bremia, Pythium, Plasmopara).

Target crops to be protected within the scope of the present invention comprise e.g. the following species of plants:

cereals (wheat, barley, rye, oats, triticale, rice, maize, sorghum and related species); beet (sugar beet and fodder beet); pomes, stone fruit and soft fruit (apples, pears, plums, peaches, almonds, cherries, strawberries, gooseberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, pepper and other spice plants, vines, hops, aubergines, bananas and natural rubber plants, as well as ornamentals.

The compounds of formula I are normally used in the form of compositions and can be applied to the crop area or plant to be treated, simultaneously or in succession, with further compounds. These further compounds can be fertilisers or micronutrient donors or other compositions that influence plant growth. They can also be selective herbicides as well as insecticides, fungicides, bactericides, nematicides, molluscicides or mixtures of several of these compositions, if desired together with further carriers, surfactants or other application-promoting adjuvants customarily employed in formulation technology.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite.

Particularly advantageous application-promoting adjuvants which are able to reduce substantially the rate of application are also natural (animal or vegetable) or synthetic phospholipids of the series of the cephalins and lecithins, which can be obtained e.g. from soybeans.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurine salts.

Non-ionic surfactants are polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

The anionic, non-ionic or cationic surfactants customarily employed in formulation technology are known to the person skilled in the art or can be taken from the relevant specialist literature:

"McCutcheon's Detergents and Emulsifiers Annual", Mc Publishing Corp., Glen Rock, N.J., 1988.

M. and J. Ash. "Encyclopedia of Surfactants", Vol. I–III, Chemical Publishing Co., New York, 1980–1981.

Dr. Helmut Stache, "Tensid-Taschenbuch", Carl Hanser Verlag, Munich/Vienna 1981.

The agrochemical compositions usually comprise 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further adjuvants, such as stabilisers, antifoams, viscosity regulators, binders, tackifiers as well as fertilisers or other active ingredients for obtaining special effects.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with an extender, e.g. with a solvent (mixture), a solid carrier and, where appropriate, surface-active compounds (surfactants).

A preferred method of applying a compound of formula I or an agrochemical composition comprising at least one of those compounds is application to the leaves (foliar application). The frequency and rate of application depend upon the risk of infestation by the pathogen in question. The compounds of formula I can, however, also penetrate the plant through the roots via the soil (systemic action) if the locus of the plant is impregnated with a liquid formulation or if the compounds are introduced in solid form into the soil, e.g. in the form of granules (soil application). In paddy rice crops, such granules may be applied in metered amounts to the flooded rice field. The compounds of formula I may, however, also be applied to seeds (coating) either by impregnating the seeds with a liquid formulation of the active ingredient, or by coating them with a solid formulation. In principle, any kind of plant propagation material can be protected using compounds of formula I, for example the seeds, roots or stems.

The compounds of formula I are used in unmodified form or, preferably, together with the adjuvants conventionally employed in formulation technology. Therefore they are advantageously formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 5 g to 2 kg of active ingredient (a.i.) per ha, preferably from 25 g to 800 g a.i./ha and especially from 50 g to 400 g a.i./ha. When used as seed-dressing agents, amounts of from 0.001 g to 1.0 g of active ingredient per kg of seed are advantageously used.

The Examples which follow serve to illustrate the invention in greater detail, without limiting it.

PREPARATION EXAMPLES

EXAMPLE P-1

Preparation of

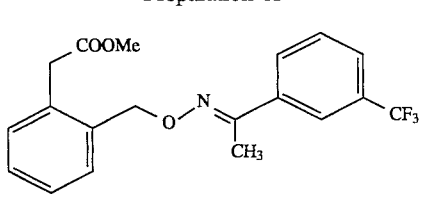

65.4 g of 2-aminooxymethylenephenylacetic acid methyl ester hydrochloride are added at 20° C. to a solution of 53.1 g of 3-trifluoromethyl-acetophenone in 530 ml of pyridine, and the mixture is heated to 90° C. After approximately 2 hours, the reaction is complete and the excess pyridine is evaporated off under a water-jet vacuum. 600 ml of water are added to the residue, the pH is adjusted to 1–2 with concentrated hydrochloric acid, and extraction is carried out three times with ethyl acetate. The combined organic phases are washed once with water and once with 10% sodium hydrogen carbonate solution, dried over sodium sulfate, filtered and concentrated to dryness by evaporation under a water-jet vacuum. A yellow oil is obtained which, according to NMR, is pure oxime in the form of an [E]/[Z] mixture. Boiling point: 168°–178° C./0.1 mbar.

EXAMPLE P-2

Preparation of

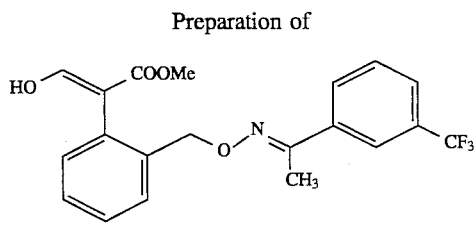

0.5 ml of methanol is added to a suspension of 6.7 g of sodium hydride in 100 ml of tert-butyl methyl ether, and then a mixture of 46 g of oxime ether, 31.3 g of methyl formate and 150 ml of tert-butyl methyl ether is added dropwise thereto at 29°–35° C., over a period of 3 hours. A short induction period must first be allowed to elapse. Then the mixture is stirred for 5 hours at 30°–35° C. For working up, the mixture is cooled to 0°–5° C., approximately 2 ml of methanol and then 100 ml of water are added, approximately 20 ml of acetic acid are added, and the phases are separated. The aqueous phase is then extracted twice with 300 ml of tert-butyl methyl ether. The combined organic phases are washed twice with 5% sodium hydrogen carbonate solution, dried over sodium sulfate, filtered and concentrated to dryness by evaporation. 3-Hydroxy-2-[α-{[(α-methyl-3-trifluoromethylbenzyl)imino]oxy}-o-tolyl]-acrylic acid methyl ester is obtained in the form of a yellow oil.

$^1$H-NMR (CDCl$_3$) δ ppm: 2.25 (s,3H), 3.74 (s,3H), 5.20 (s,2H), 7.17–7.90 (m,9H), 11.95 (d,1H).

EXAMPLE P-3

Preparation of

[Compound 1.77]

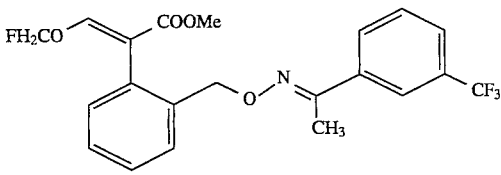

6.46 g of powdered potassium carbonate are added to a solution of 10.1 g of 3-hydroxy-2-[α-{[(α-methyl-3-trifluoromethylbenzyl)imino]oxy}-o-tolyl]-acrylic acid methyl ester in 60 ml of acetonitrile. After 15 minutes, a solution of 4.25 g of bromofluoromethane in 10 ml of acetonitrile is added dropwise at 20° C., with thorough stirring, and the mixture is further stirred for 16 hours. Water is then added and the mixture is rendered slightly acidic with 1N hydrochloric acid. After extraction with ethyl acetate, the combined organic phases are dried over sodium sulfate, filtered and concentrated by evaporation. Chromatography on silica gel with hexane/ethyl acetate (9:1) yields 3-fluoromethoxy-2-[α-{[(α-methyl-3-trifluoromethylbenzyl)imino]oxy}-o-tolyl]-acrylic acid methyl ester in the form of a light-yellow, highly viscous oil.

$^1$H-NMR (CDCl$_3$) δ ppm: 2.23 (s,3H), 3.71 (s,3H), 5.17 (s,2H), 5.45 (d,2H, J=52 Hz), 7.16–7.61 (m,7H), 7.72 (s,1H), 7.78–7.89 (s,1H). MS: m/e 425(M$^+$,6), 407(7), 239(8), 223(100).

EXAMPLE P-4

Preparation of

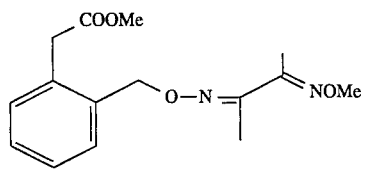

16.65 g of 2-aminooxymethylenephenylacetic acid methyl ester hydrochloride are added at 20° C. to a solution of 15 g of diacetylmonooxime methyl ether in 110 ml of pyridine, and the mixture is heated to 80° C. After 3 hours, the reaction is complete and the excess pyridine is evaporated off under a water-jet vacuum. 200 ml of water are added to the residue, the pH is adjusted to 1–2 with concentrated hydrochloric acid, and extraction is carried out with ethyl acetate. The combined organic phases are washed once with water and once with 10% sodium hydrogen carbonate solution, dried over sodium sulfate, filtered and concentrated to dryness by evaporation under a water-jet vacuum. {[(3-Methoxyimino-2-butyl)imino]oxy}-o-tolylacetic acid methyl ester is obtained in the form of a reddish oil.

$^1$H-NMR (CDCl$_3$) δ ppm: 1.98 (s,3H), 2.01 (s,3H), 3.68 (s,3H), 3.79 (s,2H), 3.94 (s,3H), 5.22 (s,2H), 7.18–7.42 (m,4H).

EXAMPLE P-5

Preparation of

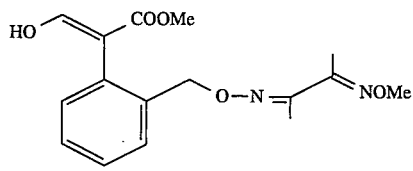

A mixture of 18.74 g of {[(3-methoxyimino-2-butyl-)imino]oxy}-o-tolylacetic acid methyl ester, 15.0 g of methyl formate, 0.2 g of methanol and 70 ml of tert-butyl methyl ether is added dropwise at 25° C., over a period of 2 hours, to a suspension of 2.99 g of sodium hydride in 45 ml of tert-butyl methyl ether. The reaction begins after ¾ hour and can readily be detected by the resulting cloudiness and the change in colour to greenish. The mixture is then stirred for 16 hours at room temperature. For working up, 2 ml of methanol are added in order to destroy any sodium hydride that is still present. After ½ hour, the reaction mixture is added to water and acidified with 20 ml of acetic acid. The phases are then separated and the aqueous phase is then extracted with tert-butyl methyl ether. The combined organic phases are washed twice with 5% sodium hydrogen carbonate solution, dried over sodium sulfate, filtered and concentrated to dryness by evaporation.

3-Hydroxy-2-[{[(3-methoxyimino-2-butyl)imino]oxy}-o-tolyl]-acrylic acid methyl ester is obtained in the form of a reddish oil.

$^1$H-NMR (CDCl$_3$) δ ppm: 1.98 (s,3H), 2.02 (s,3H), 3.73 (s,3H), 3.94 (s,3H), 5.11 (s,2H), 7.15–7.51 (m,5H), 11.95 (d,1H).

EXAMPLE P-6 [Compound 2.1]

Preparation of

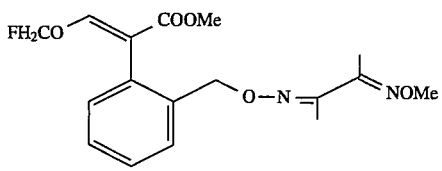

4.52 g of powdered potassium carbonate are added to a solution of 7.0 g of 3-hydroxy-2-[{[(3-methoxyimino-2-butyl)imino]oxy}-o-tolyl]-acrylic acid methyl ester in 80 ml of acetonitrile. After 15 minutes, a solution of 4.05 g of bromofluoromethane in 6 ml of acetonitrile is added dropwise at 20° C., with thorough stirring, and the mixture is then stirred for 16 hours at room temperature. Cold water is then added and the mixture is rendered slightly acidic with 1N hydrochloric acid. After extraction with ethyl acetate, the combined organic phases are washed with a sodium chloride solution, dried over sodium sulfate, filtered and concentrated by evaporation in vacuo. Chromatography on silica gel with hexane/ethyl acetate (2:1) yields 3-fluoromethoxy-2-[{[(3-methoxyimino-2-butyl)imino]oxy}-o-tolyl]-acrylic acid methyl ester in the form of a light-yellow oil.

$^1$H-NMR (CDCl$_3$) δ ppm: 1.96 (s,3H), 2.00 (s,3H), 3.71 (s,3H), 3.93 (s,3H), 5.08 (s,2H), 5.46 (d,2H, J=52 Hz), 7.15–7.50 (m,4H), 7.71 (s,1H). MS: m/e 352M$^+$(11), 223(100)

EXAMPLE P-7 [Compound 3.76]

Preparation of

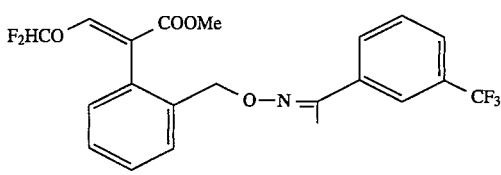

A total of 56 g of chlorodifluoromethane are introduced at 5° C., with thorough stirring, into a solution of 125 g of 3-hydroxy-2-[α-{[(α-methyl-3-trifluoromethylbenzyl)imino]oxy}-o-tolyl]-acrylic acid methyl ester (Example P-2) and 3.3 g of 15-crown-5 in 1500 ml of N-methyl-2-pyrrolidone (NMP). At the same time, a solution of 84 g of sodium hydroxide in 102 g of water is added dropwise over a period of 2.5 hours. After a reaction time of 5 hours, 120 ml of 37% hydrochloric acid are added dropwise at 0°–8° C., the mixture is diluted with 900 ml of toluene and the sodium chloride that forms is filtered off. The filtrate is stirred with potash and is filtered again, and the water is distilled off azeotropically in vacuo with the toluene. The NMP is then distilled off under a fine vacuum (b.p.: 48° C./0.55 mbar). The oil that remains is chromatographed on silica gel with hexane/ethyl acetate (10:1). Pure 3-difluoromethoxy-2-[α-{[(α-methyl-3-trifluoromethylbenzyl)imino]oxy}-o-tolyl]-acrylic acid methyl ester is obtained in the form of a yellow, highly viscous oil.

$^1$H-NMR (CDCl$_3$) δ ppm: 2.22 (s,3H), 3.72 (s,3H), 5.14 (s,2H), 6.32 (t,1H, J=70 Hz), 7.13–7.86 (m,8H), 7.89 (s,1H). MS: m/e 443 M$^+$(4), 425 (6), 257 (8), 241 (100), 225 (34)

EXAMPLE P-8 [Compound 4.1]

Preparation of

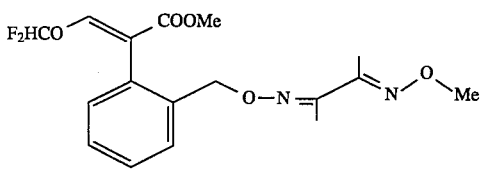

Chlorodifluoromethane is introduced at 5° C., with intensive stirring, into a solution of 9 g of 3-hydroxy-2-[{[(3-methoxyimino-2-butyl)imino]oxy}-o-tolyl]-acrylic acid methyl ester and 0.31 g of 15-crown-5 in 140 ml of NMP. At the same time, a solution of 7.84 g of sodium hydroxide in 9.8 ml of water is slowly added dropwise at 5°–10° C., and the mixture is then stirred for a further hour at the same temperature. It is then poured onto ice-water and acidified with 50 ml of 2N hydrochloric acid. After exhaustive extraction with ethyl acetate, the combined organic phases are washed with a saturated sodium hydrogen carbonate solution, dried over sodium sulfate, filtered and concentrated by evaporation in vacuo. Chromatography on silica gel with hexane/ethyl acetate (9:1) yields pure 3-difluoromethoxy-2-[{[(3-methoxyimino-2-butyl)imino]oxy}-o-tolyl]-acrylic acid methyl ester in the form of a viscous oil.

$^1$H-NMR (CDCl$_3$) δ ppm: 1.96 (s,3H), 1.99 (s,3H), 3.73 (s,3H), 3.93 (s,3H), 5.08 (s,2H), 6.35 (t,1H, J=70 Hz), 7.15–7.50 (m,4H), 7.91 (s,1H). MS: m/e 370 M$^+$(14), 241 (100)

EXAMPLE P-9

Preparation of

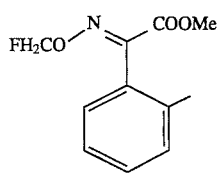

57 g of [E/Z]-o-tolylglyoxalic acid methyl ester oxime and 80 g of powdered potash are placed in 550 ml of dimethyl sulfoxide and the mixture is then stirred for 30 minutes. A solution of 40 g of bromofluoromethane in 30 ml of dimethyl sulfoxide is then added dropwise at 20° C. After 20 hours, the mixture is added to 1200 ml of water and neutralised with 230 ml of 2N hydrochloric acid. Extraction is then carried out with 4×250 ml of ethyl acetate, and the combined organic phases are washed with 200 ml of saturated sodium chloride solution, dried over sodium sulfate and concentrated by evaporation. Chromatography on silica gel with hexane/ethyl acetate (9:1) yields pure [E/Z]-o-tolylglyoxalic acid methyl ester O-fluoromethyl oxime in the form of a viscous oil.

$^1$H-NMR (CDCl$_3$) δ ppm: 2.23+2.47 (s,s,3H, [Z+E]), 3.89+3.90 (s,s,3H, [Z+E]), 5.74 (d,2H, J=52 Hz, [E+Z]), 7.12–7.39 (m,4H).

EXAMPLE P-10

Preparation of

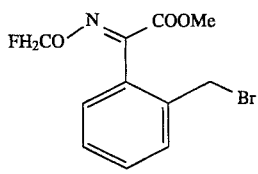

56 g of [E/Z]-o-tolylglyoxalic acid methyl ester O-fluoromethyl oxime and 0.4 g of dibenzoyl peroxide are dissolved in 350 ml of carbon tetrachloride and heated to reflux. While irradiating with a lamp, 44.5 g of N-bromosuccinimide are added in several small portions, the mixture is then allowed to react for 2 hours and, after cooling, the succinimide that has formed is filtered off. After concentration by evaporation the residue is chromatographed on silica gel with hexane/ethyl acetate (9:1). Pure [E/Z]-2-(bromomethyl)-phenylglyoxalic acid methyl ester O-fluoromethyl oxime is obtained in the form of a viscous oil.

$^1$H-NMR (CDCl$_3$) δ ppm: 3.90 (s,3H), 4.36+4.77 (s,s,2H, [Z+E]), 5.75 (d,2H), 7.16–7.53 (m,4H).

To obtain the corresponding 2-(chloromethyl)-phenylglyoxalic acid methyl ester O-fluoromethyl oxime, the mentioned starting material can be reacted with N-chlorosuccinimide.

EXAMPLE P-11 [Compound 5.13]

Preparation of

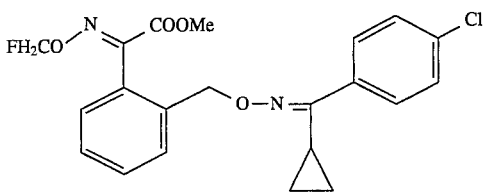

A solution of 10.4 g of 4-chlorophenylcyclopropyl ketoxime in 60 ml of dimethylformamide is added dropwise at 20° C. to a suspension of 1.28 g of sodium hydride in 5 ml of dimethylformamide. After 2 hours, a solution of 18.9 g of [E/Z]-2-(bromomethyl)phenylglyoxalic acid methyl ester O-fluoromethyl oxime in 25 ml of dimethylformamide is added dropwise and the mixture is then allowed to react for 20 hours. In order to remove the unreacted bromide, 1 g of thiourea is added and, after 30 minutes, the mixture is added to 400 ml of water. The mixture is then rendered acidic with 2N hydrochloric acid and is extracted with 3×100 ml of ethyl acetate. The combined organic phases are washed with saturated sodium chloride solution, dried over sodium sulfate, filtered and concentrated by evaporation. By means of chromatography on silica gel with hexane/ethyl acetate (19:1) it is possible to obtain the two isomers in the form of viscous oils:

Isomer A:
$^1$H-NMR (CDCl$_3$) δ ppm: 0.60–0.99 (m,4H), 1.61–1.72+2.22–2.31 (m,m,1H), 3.87+3.90 (s,s,3H), 5.25+5.43 (s,s, 2H), 5.70+5.73 (d,d,2H), 7.04–7.61 (m,8H).

Isomer B:
$^1$H-NMR (CDCl$_3$) δ ppm: 0.53–0.97 (m,4H), 1.57–1.75+2.10–2.27 (m,m,1H), 3.73+3.80 (s,s,3H), 4.93+5.11 (s,s, 2H), 5.65+5.69 (d,d,2H), 7.13–7.51 (m,8H). MS: m/e 418M$^+$(6.5), 116(100)

EXAMPLE P-12 [Compound 7.13]

Preparation of

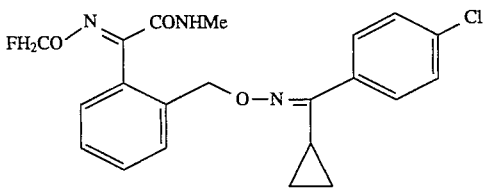

2 ml of 33% methylamine solution (in ethanol) are added to a solution of 0.45 g of {[(α-cyclopropyl-4-chlorobenzyl)imino]oxy}-o-tolylglyoxalic acid methyl ester O-fluoromethyl oxime in 12 ml of methanol, and the mixture is left to stand at room temperature for 24 hours. Concentration by evaporation and chromatography on silica gel with hexane/ethyl acetate (4:1) yield {[(α-cyclopropyl-4-chlorobenzyl)imino]oxy}-o-tolylglyoxalic acid N-methylamide O-fluoromethyl oxime in the form of a viscous oil.

$^1$H-NMR (CDCl$_3$) δ ppm: 0.52–0.97 (m,4H), 1.58–1.68+2.19–2.32 (m,m,1H), 2.44+2.69 (d,d,3H), 5.20+5.36 (s,s, 2H), 5.72+5.74 (d,d,2H), 6.39+6.80 (s[b], s[b], 1H), 7.05–7.58 (m,8H).

EXAMPLE P-13

Preparation of

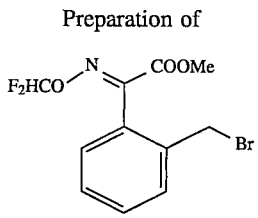

28.4 g of potassium tert-butoxide are introduced at 10°–20° C. into a solution of 19.35 g of [E/Z]-o-tolylglyoxalic acid methyl ester oxime in 250 ml of 1,2-dimethoxyethane. When a fine suspension has formed, chlorodifluoromethane is introduced at 25°–30° C. After 5 hours, concentration is carried out by evaporation in vacuo and water is added to the residue. The mixture is rendered slightly acidic with 2N hydrochloric acid and extraction is carried out with ethyl acetate. The combined organic phases are washed and concentrated by evaporation, and the crude product is then chromatographed on silica gel with hexane/ethyl acetate (5:1). Pure o-tolylglyoxalic acid methyl ester O-difluoromethyl oxime is obtained in the form of a yellow oil.

$^1$H-NMR (CDCl$_3$) δ ppm: 2.20 (s,3H), 3.87 (s,3H), 6.74 (t,1H, J=70 Hz), 7.13–7.40 (m,4H).

EXAMPLE P-14

Preparation of

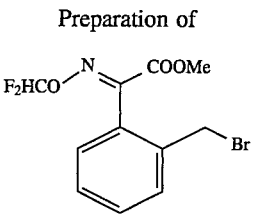

A solution of 5.1 g of O-tolylglyoxalic acid methyl ester O-difluoromethyl oxime, 0.16 g of dibenzoyl peroxide and 40 ml of carbon tetrachloride is heated to reflux. While irradiating with a lamp, 3.55 g of N-bromosuccinimide are added in several small portions and the mixture is then allowed to react under reflux for 30 minutes and is then allowed to cool to 20° C. and the succinimide that has formed is filtered off. Concentration of the filtrate by evaporation and chromatography on silica gel with hexane/ethyl acetate (6:1) yield pure 2-(bromomethyl)-phenylglyoxalic acid methyl ester O-difluoromethyl oxime in the form of a light-yellow oil.

$^1$H-NMR (CDCl$_3$) δ ppm: 3.93 (s,3H), 4.35 (s,2H), 6.77 (t,1H, J=70 Hz), 7.19–7.58 (m,4H).

In a corresponding manner, 2-(chloromethyl)-phenylglyoxalic acid methyl ester O-difluoromethyl oxime can be obtained from the starting material using N-chlorosuccinimide.

EXAMPLE P-15 [Compound 9.77]

Preparation of

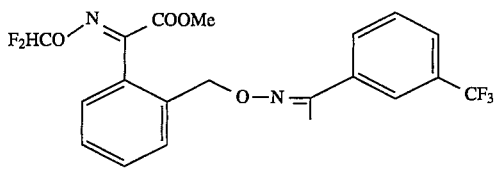

A solution of 1.25 g of 3-trifluoromethylacetophenone oxime in 5 ml of dimethylformamide is added dropwise to a suspension of 0.10 g of sodium hydride in 5 ml of dimethylformamide. When the sodium hydride has reacted, 1.40 g of 2-(bromomethyl)phenylglyoxalic acid methyl ester O-difluoromethyl oxime in 5 ml of dimethylformamide are added dropwise at 20° C. After 2 hours, 0.2 g of thiourea is added and the mixture is allowed to react for 30 minutes. It is then poured onto 200 ml of water and extraction is carried out with ethyl acetate. The combined organic phases are washed with saturated sodium chloride solution, dried over sodium sulfate, filtered and concentrated by evaporation. Chromatography on silica gel with hexane/ethyl acetate (5:1) yields pure {[(α-methyl-3-trifluoromethylbenzyl)imino]oxy}-o-tolylglyoxalic acid methyl ester O-difluoromethyl oxime in the form of a viscous oil.

$^1$H-NMR (CDCl$_3$) δ ppm: 2.20 (s,3H), 3.82 (s,3H), 5.15 (s,2H), 6.70 (t,1H), 7.25–7.86 (m,8H). MS: m/e 444 M$^+$(2.5), 116 (100)

EXAMPLE P-16 [Compound 9.78]

Preparation of

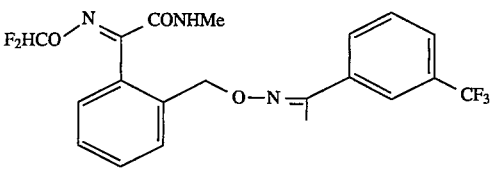

2.5 ml of 33% methylamine solution (in ethanol) are added to a solution of 0.95 g of {[(α-methyl-3-trifluoromethylbenzyl)imino]oxy}-o-tolylglyoxalic acid methyl ester O-difluoromethyl oxime in 5 ml of methanol, and the mixture is left to stand for 24 hours. Concentration by evaporation and chromatography on silica gel with hexane/ethyl acetate (3:2) yield pure {[(α-methyl-3-trifluoromethylbenzyl)imino]oxy}-o-tolylglyoxalic acid N-methylamide O-difluoromethyl oxime in the form of a highly viscous oil.

$^1$H-NMR (CDCl$_3$) δ ppm: 2.19 (s,3H), 2.89 (d,3H), 5.17 (s,2H), 6.56 (t,1H), 6.72 (s[b],1H), 7.20–7.85 (m,8H).

EXAMPLE P-17

Preparation of

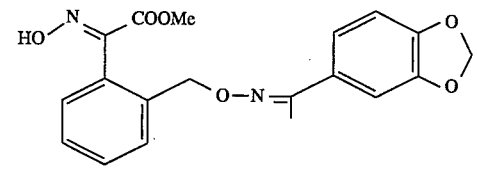

A solution of 22.8 g of {[(α-methyl-3,4-methylenedioxy-benzyl)imino]oxy}-o-tolylacetic acid methyl ester and 24 g of tert-butyl nitrite in 40 ml of tert-butanol is added dropwise at 25°–30° C. to a solution of 7.2 g of potassium tert-butoxide in 60 ml of tert-butanol. After 5 hours' stirring at 25° C., the mixture is cooled to 10° C., ice-water is added, and the mixture is acidified with 5 g of acetic acid. After exhaustive extraction with ethyl acetate, the combined organic phases are washed with saturated sodium chloride solution, dried over sodium sulfate, filtered and concentrated by evaporation in vacuo. 50 ml of diethyl ether are added to the crude product, whereupon {[(α-methyl-3,4-methylene-dioxybenzyl)imino]oxy}-o-tolylglyoxalic acid methyl ester oxime is obtained in the form of fine crystals having a melting point of 142°–146° C.

EXAMPLE P-18 [Compound 9.58]

Preparation of

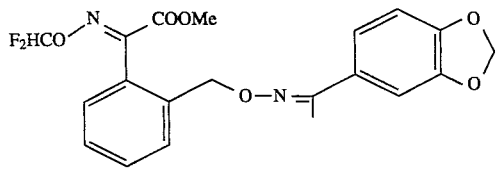

1.79 g of potassium tert-butoxide are added in portions at 20° C. to a solution of 5.57 g of {[(α-methyl-3,4-methyl-enedioxybenzyl)imino]oxy}-o-tolylglyoxalic acid methyl ester oxime in 110 ml of diethylene glycol dimethyl ether. After 20 minutes' stirring, chlorodifluoromethane is introduced at 20°–30° C., and the mixture is then stirred for a further 8 hours. For working up, the mixture is poured onto 300 ml of saturated sodium chloride solution and, after acidification with 2N hydrochloric acid, exhaustive extraction is carried out with ethyl acetate. The combined organic phases are washed with saturated sodium chloride solution and, after drying over sodium sulfate, are concentrated by evaporation in vacuo. Chromatography on silica gel with hexane/ethyl acetate (10:1) yields pure {[(α-methyl-3,4-methylenedioxybenzyl)imino]oxy}-o-tolylglyoxalic acid methyl ester O-difluoromethyl oxime in the form of a viscous oil.

$^1$H-NMR (CDCl$_3$) δ ppm: 2.13 (s,3H), 3.83 (s,3H), 5.11 (s,2H), 5.94 (s,2H), 6.70 (t,1H), 6.73–6.80 (m,1H), 7.01–7.48 (m,6H).

EXAMPLE P-19 [Compound 9.59]

Preparation of

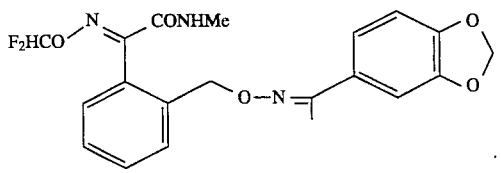

2 ml of 33% methylamine solution (in ethanol) are added to a solution of 0.36 g of {[(α-methyl-3,4-methylenedioxy-benzyl)imino]oxy}-o-tolylglyoxalic acid methyl ester O-di-fluoromethyl oxime in 5 ml of methanol, and the mixture is left to stand for 24 hours. After concentration by evaporation, chromatography is carried out on silica gel with hex-ane/ethyl acetate (2:1). Pure {[(α-methyl-3,4-methylene-dioxybenzyl)imino]oxy}-o-tolylglyoxalic acid N-methylamide O-difluoromethyl oxime is obtained in the form of a highly viscous oil.

$^1$-NMR (CDCl$_3$) δ ppm: 2.13 (s,3H), 2.86 (d,3H), 5.11 (s,2H), 5.95 (s,2H), 6.60 (t,1H), 6.67 (s[b],1H), 6.75 (d,1H), 6.99–7.53 (m,6H).

The following compounds can be prepared in that manner or analogously to one of the methods described above:
(abbreviations: Me=methyl, Et=ethyl, ⊲=cyclopropyl, b.p.= boiling point, m.p.=melting point).

TABLE 1

| Ex. No. | $R_1$ | $R_2$ | Phys. data MS: mol. peak (%) base peak |
|---|---|---|---|
| 1.1 | Me | phenyl | |
| 1.2 | Me | 2-fluorophenyl | |
| 1.3 | Me | 3-fluorophenyl | |
| 1.4 | Me | 4-fluorophenyl | |
| 1.5 | ⊲ | 4-fluorophenyl | |
| 1.6 | Me | 3-chlorophenyl | |
| 1.7 | ⊲ | 3-chlorophenyl | |
| 1.8 | Me | 4-chlorophenyl | |
| 1.9 | Me | 2-bromophenyl | |
| 1.10 | Me | 3-bromophenyl | |
| 1.11 | Me | 4-bromophenyl | |
| 1.12 | ⊲ | 4-bromophenyl | |
| 1.13 | ⊲ | 4-chlorophenyl | 417(4)/223 |
| 1.14 | CH$_3$S | 4-chlorophenyl | |
| 1.15 | CH$_3$O | 4-chlorophenyl | |
| 1.16 | CH$_3$OCH$_2$ | 4-chlorophenyl | |
| 1.17 | CH$_3$SCH$_2$ | 4-chlorophenyl | |
| 1.18 | CF$_3$ | 4-chlorophenyl | |
| 1.19 | CN | 4-chlorophenyl | |
| 1.20 | Et | 4-chlorophenyl | |
| 1.21 | propyl | 4-chlorophenyl | |
| 1.22 | isopropyl | 4-chlorophenyl | |
| 1.23 | Me | 2,4-difluorophenyl | |
| 1.24 | Me | 3,4-difluorophenyl | |
| 1.25 | Me | 2,3-difluorophenyl | |
| 1.26 | Me | 3,4-difluorophenyl | |
| 1.27 | Me | 2,5-difluorophenyl | |
| 1.28 | Me | 3,5-difluorophenyl | |
| 1.29 | Me | 2,4-dichlorophenyl | |
| 1.30 | Me | 3,4-dichlorophenyl | |
| 1.31 | Me | 2,5-dichlorophenyl | |
| 1.32 | Me | 3,5-dichlorophenyl | |
| 1.33 | Me | 3-Cl,4-F-phenyl | |
| 1.34 | Me | 4-Cl,2-F-phenyl | |
| 1.35 | Me | 2,3,4-trifluorophenyl | |
| 1.36 | Me | 2,3,6-trifluorophenyl | |
| 1.37 | Me | 2,4,6-trifluorophenyl | |
| 1.38 | Me | 2,4,5-trifluorophenyl | |
| 1.39 | Me | 2,3,4-trichlorophenyl | |

TABLE 1-continued (Ia) structure: FH₂CO—C(=C(COOMe))—[phenyl with ortho CH₂—O—N=C(R₁)(R₂)]

| No. | R₁ | R₂ | data |
|---|---|---|---|
| 1.40 | Me | 3,4,5-trichlorophenyl | |
| 1.41 | Me | 2,4,5-trichlorophenyl | |
| 1.42 | Me | 1-naphthyl | |
| 1.43 | Me | 2-naphthyl | |
| 1.44 | cyclopropyl | 2-naphthyl | |
| 1.45 | Me | 2-methylphenyl | |
| 1.46 | Me | 3-methylphenyl | |
| 1.47 | Me | 4-methylphenyl | |
| 1.48 | cyclopropyl | 4-methylphenyl | |
| 1.49 | Me | 2,3-dimethylphenyl | |
| 1.50 | Me | 2,4-dimethylphenyl | |
| 1.51 | Me | 2,4-dimethylphenyl | |
| 1.52 | Me | 3,4-dimethylphenyl | |
| 1.53 | Me | 3,5-dimethylphenyl | |
| 1.54 | Me | 2-methoxyphenyl | |
| 1.55 | Me | 3-methoxyphenyl | |
| 1.56 | Me | 4-methoxyphenyl | |
| 1.57 | Me | 3,4-dimethoxyphenyl | |
| 1.58 | Me | 3,5-dimethoxyphenyl | |
| 1.59 | Me | 3,4-methylenedioxyphenyl | |
| 1.60 | cyclopropyl | 3,4-methylenedioxyphenyl | |
| 1.61 | SMe | 3,4-methylenedioxyphenyl | |
| 1.62 | OMe | 3,4-methylenedioxyphenyl | |
| 1.63 | Me | 3,4-ethylenedioxyphenyl | |
| 1.64 | cyclopropyl | 3,4-ethylenedioxyphenyl | |
| 1.65 | Me | 2,2-difluoro-5-benzodioxolyl | |
| 1.66 | Et | 2,2-difluoro-5-benzodioxolyl | |
| 1.67 | Me | 3-difluoromethoxyphenyl | 423(5)/223 |
| 1.68 | Me | 4-difluoromethoxyphenyl | |
| 1.69 | Me | 3-(2,2,2-trifluoroethoxy)-phenyl | |
| 1.70 | Me | 3-(1,1,2,2-tetrafluoro-ethoxy)-phenyl | |
| 1.71 | Me | 3-(1,1,2,3,3,3-Hexafluoro-propoxy)phenyl | |
| 1.72 | Me | 4-(2,2,2-trifluoroethoxy)-phenyl | |
| 1.73 | Me | 4-(1,1,2,2-tetrafluoro-ethoxy)-phenyl | |
| 1.74 | Me | 3-trifluoromethoxyphenyl | 441(6)/223 |
| 1.75 | Me | 4-trifluoromethoxyphenyl | |
| 1.76 | Me | 2-trifluoromethylphenyl | |
| 1.77 | Me | 3-trifluoromethylphenyl | 425(6)/223 |
| 1.78 | cyclopropyl | 3-trifluoromethylphenyl | |
| 1.79 | Et | 3-trifluoromethylphenyl | |
| 1.80 | CN | 3-trifluoromethylphenyl | |
| 1.81 | OMe | 3-trifluoromethylphenyl | |
| 1.82 | SMe | 3-trifluoromethylphenyl | |
| 1.83 | CH₂OCH₃ | 3-trifluoromethylphenyl | |
| 1.84 | Me | 3,5-bis(trifluoromethyl)-phenyl | |
| 1.85 | Me | 4-F,3-CF₃-phenyl | |
| 1.86 | cyclopropyl | 4-F,3-CF₃-phenyl | |
| 1.87 | Me | 2-Cl,5-CF₃-phenyl | |
| 1.88 | Me | 3,5-dichloro-2-fluoro-4-methoxy-phenyl | 473(6)/223 |
| 1.89 | Me | 3,5-dichloro-2,4-dimethoxy-phenyl | 485(4)/223 |
| 1.90 | Me | 3-acetylphenyl | |
| 1.91 | Me | 4-acetylphenyl | |
| 1.92 | Me | 3-carboxyphenyl | |
| 1.93 | Me | 4-carboxyphenyl | |
| 1.94 | Me | 3-carbethoxyphenyl | |
| 1.95 | Me | 4-carbethoxyphenyl | |
| 1.96 | Me | 2-cyanophenyl | |
| 1.97 | Me | 3-cyanophenyl | |
| 1.98 | Me | 4-cyanophenyl | |
| 1.99 | Me | 3-cyanomethylphenyl | |
| 1.100 | Me | 3-cyanomethoxyphenyl | |
| 1.101 | Me | 4-cyanomethylphenyl | |
| 1.102 | Me | 4-cyclohexylphenyl | |
| 1.103 | Me | 4-biphenylyl | |
| 1.104 | Me | 2-fluorenyl | |
| 1.105 | Me | 3-benzyloxyphenyl | |
| 1.106 | Me | 4-benzyloxyphenyl | |
| 1.107 | Me | 3,5-dibenzyloxyphenyl | |
| 1.108 | Me | 4-bromo-2-fluorophenyl | |
| 1.109 | Me | 4-bromo-3-methylphenyl | |
| 1.110 | Me | 6-(2,2-difluoro-1,4-benzodioxanyl) | |
| 1.111 | Me | 6-(2,2,3-trifluoro-1,4-benzodioxanyl) | |
| 1.112 | Me | pentafluorophenyl | |
| 1.113 | Me | 3-F,5-CF₃-phenyl | |
| 1.114 | Me | 3-OMe,5-CF₃-phenyl | |
| 1.115 | Me | 3-NO₂,5-CF₃-phenyl | |
| 1.116 | Me | 4-Br,3-CF₃-phenyl | |
| 1.117 | Me | 4-tert-butylphenyl | |
| 1.118 | Me | 4-sec-butylphenyl | |
| 1.119 | Me | 4-butylphenyl | |
| 1.120 | Me | 4-butoxyphenyl | |
| 1.121 | Me | 3-F,4-MeO-phenyl | 405(10)/166 |
| 1.122 | Me | 3-Cl,4-MeO-phenyl | |
| 1.123 | Me | 3-Cl,4-Me-phenyl | |
| 1.124 | Me | 4-Cl,2-Me-phenyl | |
| 1.125 | Me | 4-Cl,3-Me-phenyl | |
| 1.126 | Me | 5-Cl,2-Me-phenyl | |
| 1.127 | Me | 4-Cl,3-NO₂-phenyl | |
| 1.128 | Me | 5-indanyl | |
| 1.129 | Me | 3,5-dinitrophenyl | |
| 1.130 | Me | 2-nitrophenyl | |
| 1.131 | Me | 3-nitrophenyl | |
| 1.132 | Me | 4-nitrophenyl | |
| 1.133 | Me | 2-ethylphenyl | |
| 1.134 | Me | 3-ethylphenyl | |
| 1.135 | Me | 4-ethylphenyl | |
| 1.136 | Me | 3-ethoxyphenyl | |
| 1.137 | Me | 4-ethoxyphenyl | |
| 1.138 | Me | 3-F,4-CH₃-phenyl | |
| 1.139 | Me | 4-F,3-NO₂-phenyl | |
| 1.140 | Me | 4-Cl,3-CF₃-phenyl | |
| 1.141 | Et | 3-hydroxyphenyl | |
| 1.142 | Me | 4-hydroxyphenyl | |
| 1.143 | Me | 3-hydroxy-4-methoxyphenyl | |
| 1.144 | Me | 4-hydroxy-3-methylphenyl | |
| 1.145 | Me | 4-hydroxy-3-nitrophenyl | |
| 1.146 | Me | 4-isopropylphenyl | |
| 1.147 | Me | 3-iodophenyl | |
| 1.148 | Me | 4-iodophenyl | |
| 1.149 | Me | 3-mercaptophenyl | |

TABLE 1-continued

(Ia)

| | | |
|---|---|---|
| 1.150 | Me | 4-mercaptophenyl |
| 1.151 | Me | 2-NH$_2$C(S)-phenyl |
| 1.152 | Me | 3-NH$_2$C(S)-phenyl |
| 1.153 | Me | 4-NH$_2$C(S)-phenyl |
| 1.154 | Me | 3-methylmercaptophenyl |
| 1.155 | Me | 4-methylmercaptophenyl |
| 1.156 | Me | 2-methylthio-5-CF$_3$-phenyl |
| 1.157 | Me | 4-CH$_3$,3-NO$_2$-phenyl |
| 1.158 | Me | 4-CH$_3$,2-NO$_2$-phenyl |
| 1.159 | Me | 2-CH$_3$,4-NO$_2$-phenyl |
| 1.160 | Me | 2-CH$_3$,5-NO$_2$-phenyl |
| 1.161 | Me | 4-methoxy,3-NO$_2$-phenyl |
| 1.162 | Me | 4-(4-morpholino)phenyl |
| 1.163 | Me | 3-phenoxyphenyl |
| 1.164 | Me | 4-phenoxyphenyl |
| 1.165 | Me | 4-propylphenyl |
| 1.166 | Me | 3-methanesulfinylmethyl-4-MeO-phenyl |
| 1.167 | Me | 4-sulfamoylphenyl |
| 1.168 | Me | 4-MeO,3-CH$_3$SCH$_2$-phenyl |
| 1.169 | Me | 3-trifluoromethylsulfonyl-phenyl |
| 1.170 | Me | 3-rhodanophenyl |
| 1.171 | Me | 4-rhodanophenyl |
| 1.172 | Me | 3-rhodanomethylphenyl |
| 1.173 | Me | 4-rhodanomethylphenyl |
| 1.174 | Me | 3-prop-1-en-3-yloxyphenyl |
| 1.175 | Me | 2-cyclopropylmethoxyphenyl |
| 1.176 | Me | 2,3,4,5-tetrafluorophenyl |
| 1.177 | Me | 2,3,5,6-tetrafluorophenyl |
| 1.178 | Me | 2,3,4-trimethoxyphenyl |
| 1.179 | Me | 3,4,5-trimethoxyphenyl |
| 1.180 | Me | 5,6,7,8-tetrahydro-1-naphthyl |
| 1.181 | Me | 2,3-dihydrobenzofur-5-yl |
| 1.182 | Me | 2,3-dihydrobenzofur-6-yl |
| 1.183 | Me | 7-OMe,2,3-dihydrobenzo-fur-5-yl |
| 1.184 | Me | 3-trimethylsilylphenyl |
| 1.185 | CF$_3$ | 3-trimethylsilylphenyl |
| 1.186 | Me | benzyl |
| 1.187 | Me | 3-CF$_3$-benzyl |
| 1.188 | Me | 4-chlorobenzyl |
| 1.189 | Me | 3-CF$_3$,4-chlorobenzyl |
| 1.190 | Me | phenoxymethyl |
| 1.191 | Me | 3-chlorophenoxymethyl |
| 1.192 | Me | 3-CF$_3$-phenoxymethyl |
| 1.193 | Me | 2-methoxy-5-benzodioxolyl |
| 1.194 | Me | 2-methyl-5-benzodioxolyl |
| 1.195 | Me | 2-phenyl-5-benzodioxolyl |
| 1.196 | Me | 3-methoxycarbonyl-phenyl |
| 1.197 | Me | 4-methoxycarbonyl-phenyl |
| 1.198 | Me | 3-methoximinomethyl-phenyl |
| 1.199 | Me | 3-ethoximinomethyl-phenyl |
| 1.200 | Me | 4-methoximinomethyl-phenyl |
| 1.201 | Me | 2-pyrazinyl |
| 1.202 | Me | 3,5-dimethyl-pyrazin-2-yl |
| 1.203 | Me | 3-ethoxy-pyrazin-2-yl |
| 1.204 | Me | 5-CONHCH$_3$-pyrazin-2-yl |
| 1.205 | Me | 2-pyrimidinyl |
| 1.206 | Me | 4-chloro-pyrimidin-2-yl |
| 1.207 | Me | 4-ethoxy-pyrimidin-2-yl |
| 1.208 | Me | 4-methoxy-pyrimidin-2-yl |
| 1.209 | Me | 4-(2,2,2-trifluoroethoxy)-pyrimidin-2-yl |
| 1.210 | Me | 2-SCH$_3$-pyrimidin-4-yl |
| 1.211 | Me | 4-isopropoxy-pyrimidin-2-yl |
| 1.212 | Me | 4,6-dimethyl-pyrimidin-2-yl |
| 1.213 | Me | 4-Me,6-cyclopropyl-pyrimidin-2-yl |
| 1.214 | Me | 4,6-diethoxy-pyrimidin-2-yl |

TABLE 1-continued

(Ia)

| | | | |
|---|---|---|---|
| 1.215 | Me | 4-Me,6-OMe-pyrimidin-2-yl | |
| 1.216 | Me | 4-Me,6-CF$_3$-pyrimidin-2-yl | |
| 1.217 | Me | 2-pyridyl | |
| 1.218 | Me | 3-pyridyl | |
| 1.219 | ◁ | 4-pyridyl | |
| 1.220 | Me | 2,6-dichloro-4-pyridyl | |
| 1.221 | Me | 2-chloro-4-pyridyl | |
| 1.222 | Me | 2-quinolinyl | |
| 1.223 | Me | 6-quinolinyl | |
| 1.224 | Me | 7-quinolinyl | |
| 1.225 | Me | 5-isoquinolinyl | |
| 1.226 | Me | 2-benzimidazolyl | |
| 1.227 | Me | 3,4-benzocumarin-6-yl | |
| 1.228 | Me | 2-thienyl | |
| 1.229 | Me | 3-methylbenzo(b)thien-2-yl | |
| 1.230 | Me | 5-chlorothien-2-yl | |
| 1.231 | Me | 5-bromothien-2-yl | |
| 1.232 | Me | 2-methoxycarbonyl-3-thienyl | |
| 1.233 | Me | 2-furyl | |
| 1.234 | Me | benzo[b]fur-2-yl | |
| 1.235 | Me | 1-methylpyrrol-2-yl | |
| 1.236 | Me | 4-methylthien-2-yl | |
| 1.237 | Me | 5-methylfur-2-yl | |
| 1.238 | Me | 6-bromo-2-pyridyl | |
| 1.239 | Me | 4-trifluoromethyl-2-pyridyl | |
| 1.240 | Me | 4-ethoxy-pyrimidin-2-yl | |
| 1.241 | Me | 5-chloro-2-pyridyl | |
| 1.242 | Me | 5-bromo-2-pyridyl | |
| 1.243 | Me | 6-trifluoromethyl-2-pyridyl | |
| 1.244 | Me | 6-quinoxalinyl | |
| 1.245 | Me | 2-quinoxalinyl | |
| 1.246 | Me | 6-chloro-2-quinoxalinyl | |
| 1.247 | Me | 2-thiazolyl | |
| 1.248 | Me | 5-trifluoromethyl-2-pyridyl | |
| 1.249 | Me | 2,1,3-benzothiadiazol-5-yl | |
| 1.250 | Me | 2,1,3-benzoxadiazol-5-yl | |
| 1.251 | Me | 4-CN-2-pyridyl | |
| 1.252 | Me | 5-bromo-3-pyridyl | |
| 1.253 | Me | 6-methyl-3-pyridyl | |
| 1.254 | Me | 1-morpholinyl | |
| 1.255 | Me | 1-(2,6-dimethylmorpholinyl) | |
| 1.256 | Me | 1-(2-methylmorpholinyl) | |
| 1.257 | Me | 1-piperidinyl | |
| 1.258 | Me | 1-piperazinyl | |
| 1.259 | Me | methyl | |
| 1.260 | Me | ethyl | |
| 1.261 | Me | propyl | |
| 1.262 | Me | isopropyl | |
| 1.263 | Me | cyclopropyl | |
| 1.264 | ◁ | cyclopropyl | |
| 1.265 | CN | isopropyl | |
| 1.266 | CN | cyclopropyl | |
| 1.267 | CN | phenyl | |
| 1.268 | Me | 4-Me,3-pentenyl | 363(4.7)/82 |
| 1.269 | Me | 4-Me,3-hexenyl | 377(9.5)/96 |
| 1.270 | Me | 4-Me,3-heptenyl | 391(8)/95 |
| 1.271 | Me | 4,6-Me$_2$,3-heptenyl | 405(10)/109 |
| 1.272 | Me | 4,8-Me$_2$;3,7-nonadienyl | 431(3)/69 |
| 1.273 | Me | 4-MeO-2,3,5,6-tetrafluoro-phenyl | 459(3)/223 |
| 1.274 | Me | 5-benzofurazanyl | 86–89° C. |

TABLE 1-continued (Ia) structure: FH₂CO-CH=C(COOMe)-[phenyl]-CH₂-O-N=C(R₁)R₂

| Ex. No. | N=C(R₁)R₂ | Phys. data |
|---|---|---|
| 1.275 | 4-fluoro-indan-1-ylidene imino | |
| 1.276 | 5-fluoro-chroman-4-ylidene imino | |
| 1.277 | 3-(4-chlorophenyl)-5,6-dihydro-2H-1,4-thiazin-2-ylidene imino | |
| 1.278 | 3-(4-methoxyphenyl)-5,6-dihydro-2H-1,4-thiazin-2-ylidene imino | |
| 1.279 | 3-(4-trifluoromethylphenyl)-5,6-dihydro-2H-1,4-thiazin-2-ylidene imino | |
| 1.280 | 3-(2,5-difluorophenyl)-5,6-dihydro-2H-1,4-thiazin-2-ylidene imino | |
| 1.281 | 3-isopropyl-5,6-dihydro-2H-1,4-thiazin-2-ylidene imino | |
| 1.282 | 3-(3,4-methylenedioxyphenyl)-5,6-dihydro-2H-1,4-thiazin-2-ylidene imino | |
| 1.283 | 3-(4-phenoxyphenyl)-5,6-dihydro-2H-1,4-thiazin-2-ylidene imino | |
| 1.284 | 3-(4-fluorophenyl)-5,6-dihydro-2H-1,4-thiazin-2-ylidene imino | |

TABLE 2

$$\text{(Ia)}$$

Structure: FH₂CO and COOMe groups on a C=C, attached to a phenyl ring with a -CH₂-O-N=C(R₁)-C(R₃)=N-O-R₄ substituent.

| Ex. No. | R₁ | R₃ | R₄ | Phys. data m.p. or MS: mol. peak (%) base peak |
|---|---|---|---|---|
| 2.1 | Me | Me | Me | 352(11)/223 |
| 2.2 | Δ | Me | Me | |
| 2.3 | Me | Δ | Me | |
| 2.4 | Me | Me | phenyl | |
| 2.5 | Me | Δ | phenyl | |
| 2.6 | Me | Me | benzyl | |
| 2.7 | Me | Me | Et | |
| 2.8 | Δ | Me | Et | |
| 2.9 | Me | Δ | Et | |
| 2.10 | H | Me | methoxymethyl | |
| 2.11 | Me | Me | methoxymethyl | |
| 2.12 | Me | Δ | methoxymethyl | |
| 2.13 | Δ | Me | methoxymethyl | |
| 2.14 | Me | Me | ethoxymethyl | |
| 2.15 | H | Me | cyanomethyl | |
| 2.16 | Me | Me | cyanomethyl | |
| 2.17 | Δ | Me | cyanomethyl | |
| 2.18 | H | Me | tert-butyl | |
| 2.19 | Me | Me | tert-butyl | |
| 2.20 | Me | Me | propargyl | |
| 2.21 | Δ | Me | propargyl | |
| 2.22 | Me | Δ | propargyl | |
| 2.23 | Me | Me | 2,2-dichlorocyclo-propylmethyl | |
| 2.24 | Δ | Me | 2,2-dichlorocyclo-propylmethyl | |
| 2.25 | H | Me | allyl | |
| 2.26 | Me | Me | allyl | 378(10)/223 |
| 2.27 | Me | Me | CF₃CH₂ | 420(2)/147 |
| 2.28 | Δ | Me | CF₃CH₂ | |
| 2.29 | Me | Me | CF₃CH₂CH₂ | |
| 2.30 | Me | Me | CF₃CH₂CH₂CH₂ | |
| 2.31 | Δ | Me | CF₃CH₂CH₂CH₂ | |
| 2.32 | Me | Me | 2-chloro-2-propenyl | |
| 2.33 | Δ | Me | 2-chloro-2-propenyl | |
| 2.34 | Me | Me | propyl | |
| 2.35 | Me | Me | butyl | |
| 2.36 | Me | Me | hexyl | |
| 2.37 | Me | Me | methoxycarbonylmethyl | |
| 2.38 | Me | Me | 3-fluorobenzyl | |
| 2.39 | Me | Me | 4-chlorobenzyl | |
| 2.40 | Me | Me | 2-chlorobenzyl | |
| 2.41 | Me | Me | 2-CF₃-benzyl | |
| 2.42 | Me | Me | 3-CF₃-benzyl | |
| 2.43 | Me | Me | 4-CF₃-benzyl | |
| 2.44 | Me | Me | 3,4-dichlorobenzyl | |
| 2.45 | Me | Me | 2,4,6-trimethylbenzyl | |
| 2.46 | Me | Me | 4-chloro-2-nitrobenzyl | |
| 2.47 | Me | Me | 3-methoxybenzyl | |
| 2.48 | Me | Me | 2-phenethyl | |
| 2.49 | Me | Me | 3-phenylpropyl | |
| 2.50 | Me | Me | 2-(4-nitrophenyl)ethyl | |
| 2.51 | Me | Me | 2-(2-CF₃-phenyl)ethyl | |
| 2.52 | Me | Me | 2-(4-methoxyphenyl)ethyl | |
| 2.53 | Me | Me | 2-chloro-6-fluorobenzyl | |
| 2.54 | Me | Me | 3,4-methylenedioxybenzyl | |
| 2.55 | Me | Me | 2-cyanobenzyl | |
| 2.56 | Me | Me | 2-(4-chlorophenyl)ethyl | |
| 2.57 | Me | Me | cyclopropylmethyl | 392(7.5)/55 |
| 2.58 | Me | Me | 2-(1,3-dioxolanyl)methyl | |
| 2.59 | Me | Me | 2,2,3,3-tetrafluorocyclo-butylmethyl | |
| 2.60 | Me | Me | α-fluoroethoxycarbonylmethyl | |
| 2.61 | Me | 3-CF₃-pehnyl | Me | |
| 2.62 | Me | 4-chloro-phenyl | Me | |
| 2.63 | Me | 3-chloro- | Me | |

TABLE 2-continued $$FH_2CO\text{-}C(COOMe)=CH\text{-}[2\text{-}(CH_2ON=C(R_1)C(R_3)=NOR_4)C_6H_4]$$ (Ia)

| Ex. No. | $R_1$ | $R_3$ | $R_4$ | Phys. data m.p. or MS: mol. peak (%) base peak |
|---|---|---|---|---|
| 2.64 | Me | 2-fluoro-phenyl | Me | |
| 2.65 | Me | 4-methyl-phenyl | Me | |
| 2.66 | Me | 4-methoxy-phenyl | Me | |
| 2.67 | Me | 4-bromo-phenyl | Me | |
| 2.68 | Me | 2-thienyl | Me | |
| 2.69 | Me | 4-fluoro-phenyl | Me | |
| 2.70 | Me | 3-fluoro-5-CF$_3$-phenyl | Me | |
| 2.71 | Me | phenyl | Me | |
| 2.72 | Me | 2-methyl-phenyl | Me | |
| 2.73 | Me | 3-bromo-phenyl | Me | |
| 2.74 | Me | 3,4-methylene-dioxyphenyl | Me | |
| 2.75 | Me | 4-methyl-phenyl | Et | |
| 2.76 | Me | Δ | CH$_2$CH$_2$F | |
| 2.77 | Δ | Me | CH$_2$CH$_2$F | |
| 2.78 | Me | Me | CH$_2$CH$_2$F | 384(14)/223 |
| 2.79 | Me | 4-allyloxy-phenyl | Me | 470(2.05)/41 |
| 2.80 | SMe | 4-methyl-phenyl | Me | |
| 2.81 | Et | 4-methyl-phenyl | Me | |
| 2.82 | Me | 4-isobutyl-phenyl | Me | |
| 2.83 | Me | 4-propargyl-oxyphenyl | Me | |
| 2.84 | Me | 4-(2,2,2-tri-fluoroethoxy)-phenyl | Me | |
| 2.85 | Me | 4-ethoxy-phenyl | Me | 458(11.8)/147 |
| 2.86 | CN | 4-methyl-phenyl | Me | |
| 2.87 | CN | 4-chloro-phenyl | Me | |
| 2.88 | CN | 3,4-dichloro-phenyl | Me | |
| 2.89 | CN | 4-trifluoro-methoxyphenyl | Me | |
| 2.90 | CN | 3-trifluoro-methylphenyl | Me | |
| 2.91 | CN | 2-chloro-phenyl | Me | |
| 2.92 | CN | 4-fluoro-phenyl | Me | |
| 2.93 | Me | 3-ethoxy-phenyl | Me | |
| 2.94 | Me | 3-propoxy-phenyl | Me | |
| 2.95 | Me | 4-propoxy-phenyl | Me | |
| 2.96 | Me | 3-MeS-phenyl | Me | |
| 2.97 | Me | 4-MeS-phenyl | Me | |
| 2.98 | Me | 3-propyl-S-phenyl | Me | |
| 2.99 | Me | 3-ethyl-S-phenyl | Me | |

TABLE 2-continued

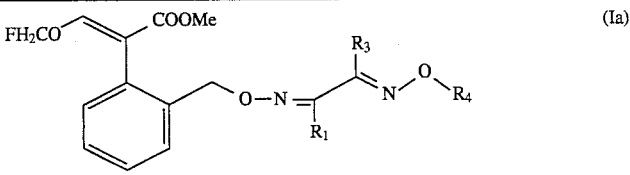

| Ex. No. | R₁ | R₃ | R₄ | Phys. data m.p. or MS: mol. peak (%) base peak |
|---|---|---|---|---|
| 2.100 | Me | 4-ethyl-S-phenyl | Me | |
| 2.101 | Me | 4-ethoxy-phenyl | Me | |
| 2.102 | Me | 4-propyl-S-phenyl | Me | |
| 2.103 | Me | 4-(3-F-phenoxy)-phenyl | Me | |
| 2.104 | Me | 4-(4-F-phenoxy)-phenyl | Me | |

TABLE 3

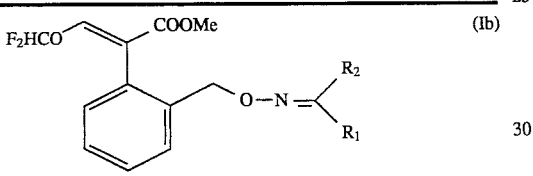

| Ex. No. | R₁ | R₂ | Phys. data MS: mol. peak (%) base peak |
|---|---|---|---|
| 3.1 | Me | phenyl | |
| 3.2 | Me | 2-fluorophenyl | |
| 3.3 | Me | 3-fluorophenyl | |
| 3.4 | Me | 4-fluorophenyl | |
| 3.5 | ◁ | 4-fluorophenyl | |
| 3.6 | Me | 3-chlorophenyl | |
| 3.7 | ◁ | 3-chlorophenyl | |
| 3.8 | Me | 4-chlorophenyl | 435(6)/241 |
| 3.9 | Me | 2-bromophenyl | |
| 3.10 | Me | 3-bromophenyl | |
| 3.11 | Me | 4-bromophenyl | |
| 3.12 | ◁ | 4-bromophenyl | |
| 3.13 | ◁ | 4-chlorophenyl | |
| 3.14 | CH₃S | 4-chlorophenyl | |
| 3.15 | CH₃O | 4-chlorophenyl | |
| 3.16 | CH₃OCH₂ | 4-chlorophenyl | |
| 3.17 | CH₃SCH₂ | 4-chlorophenyl | |
| 3.18 | CF₃ | 4-chlorophenyl | |
| 3.19 | CN | 4-chlorophenyl | |
| 3.20 | Et | 4-chlorophenyl | |
| 3.21 | propyl | 4-chlorophenyl | |
| 3.22 | isopropyl | 4-chlorophenyl | |
| 3.23 | Me | 2,4-difluorophenyl | |
| 3.24 | Me | 3,4-difluorophenyl | |
| 3.25 | Me | 2,3-difluorophenyl | |

TABLE 3-continued

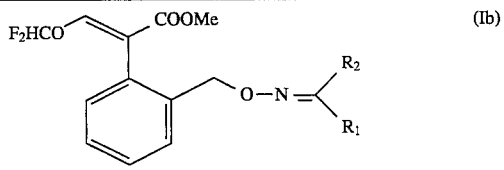

| Ex. No. | R₁ | R₂ |
|---|---|---|
| 3.26 | Me | 2,5-difluorophenyl |
| 3.27 | Me | 3,5-difluorophenyl |
| 3.28 | Me | 2,4-dichlorophenyl |
| 3.29 | Me | 3,4-dichlorophenyl |
| 3.30 | Me | 2,5-dichlorophenyl |
| 3.31 | Me | 3,5-dichlorophenyl |
| 3.32 | Me | 3-Cl,4-F-phenyl |
| 3.33 | Me | 4-Cl,2-F-phenyl |
| 3.34 | Me | 2,3,4-trifluorophenyl |
| 3.35 | Me | 2,3,6-trifluorophenyl |
| 3.36 | Me | 2,4,6-trifluorophenyl |
| 3.37 | Me | 2,4,5-trifluorophenyl |
| 3.38 | Me | 2,3,4-trichlorophenyl |
| 3.39 | Me | 3,4,5-trichlorophenyl |
| 3.40 | Me | 2,4,5-trichlorophenyl |
| 3.41 | Me | 1-naphthyl |
| 3.42 | Me | 2-naphthyl |
| 3.43 | ◁ | 2-naphthyl |
| 3.44 | Me | 2-methylphenyl |
| 3.45 | Me | 3-methylphenyl |
| 3.46 | Me | 4-methylphenyl |
| 3.47 | ◁ | 4-methylphenyl |
| 3.48 | Me | 2,3-dimethylphenyl |
| 3.49 | Me | 2,4-dimethylphenyl |
| 3.50 | Me | 2,5-dimethylphenyl |
| 3.51 | Me | 3,4-dimethylphenyl |
| 3.52 | Me | 3,5-dimethylphenyl |
| 3.53 | Me | 2-methoxyphenyl |
| 3.54 | Me | 3-methoxyphenyl |
| 3.55 | Me | 4-methoxyphenyl |
| 3.56 | Me | 3,4-dimethoxyphenyl |
| 3.57 | Me | 3,5-dimethoxyphenyl |
| 3.58 | Me | 3,4-methylenedioxyphenyl |
| 3.59 | ◁ | 3,4-methylenedioxyphenyl |

TABLE 3-continued (Ib) structure: F₂HCO—C(=CH...)—COOMe attached to benzene ring with ortho -CH₂-O-N=C(R₁)(R₂)

| No. | R₂ | R₁ | |
|---|---|---|---|
| 3.60 | SMe | 3,4-methylenedioxyphenyl | |
| 3.61 | OMe | 3,4-methylenedioxyphenyl | |
| 3.62 | Me | 3,4-ethylenedioxyphenyl | |
| 3.63 | ◁ | 3,4-ethylenedioxyphenyl | |
| 3.64 | Me | 2,2-difluoro-5-benzodioxolyl | |
| 3.65 | Et | 2,2-difluoro-5-benzodioxolyl | |
| 3.66 | Me | 3-difluoromethoxyphenyl | 441(10)/241 |
| 3.67 | Me | 4-difluoromethoxyphenyl | |
| 3.68 | Me | 3-(2,2,2-trifluoroethoxy)-phenyl | |
| 3.69 | Me | 3-(1,1,2,2-tetrafluoro-ethoxy)-phenyl | |
| 3.70 | Me | 3-(1,1,2,3,3,3-hexafluoro-propoxy)phenyl | |
| 3.71 | Me | 4-(2,2,2-trifluoroethoxy)-phenyl | |
| 3.72 | Me | 4-(1,1,2,2-tetrafluoro-ethoxy)-phenyl | |
| 3.73 | Me | 3-trifluoromethoxyphenyl | |
| 3.74 | Me | 4-trifluoromethoxyphenyl | |
| 3.75 | Me | 2-trifluoromethylphenyl | |
| 3.76 | Me | 3-trifluoromethylphenyl | 443(4)/241 |
| 3.77 | ◁ | 3-trifluoromethylphenyl | |
| 3.78 | Et | 3-trifluoromethylphenyl | |
| 3.79 | CN | 3-trifluoromethylphenyl | |
| 3.80 | OMe | 3-trifluoromethylphenyl | |
| 3.81 | SMe | 3-trifluoromethylphenyl | |
| 3.82 | CH₂OCH₃ | 3-trifluoromethylphenyl | |
| 3.83 | Me | 3,5-bis(trifluoromethyl)-phenyl | |
| 3.84 | Me | 4-F,3-CF₃-phenyl | |
| 3.85 | ◁ | 4-F,3-CF₃-phenyl | |
| 3.86 | Me | 2-Cl,5-CF₃-phenyl | |
| 3.87 | Me | 3,5-dichloro-2-fluoro-4-methoxy-phenyl | 491(4)/241 |
| 3.88 | Me | 3,5-dichloro-2,4-dimethoxy-phenyl | |
| 3.89 | Me | 3-acetylphenyl | |
| 3.90 | Me | 4-acetylphenyl | |
| 3.91 | Me | 3-carboxyphenyl | |
| 3.92 | Me | 4-carboxyphenyl | |
| 3.93 | Me | 3-carbethoxyphenyl | |
| 3.94 | Me | 4-carbethoxyphenyl | |
| 3.95 | Me | 2-cyanophenyl | |
| 3.96 | Me | 3-cyanophenyl | |
| 3.97 | Me | 4-cyanophenyl | |
| 3.98 | Me | 3-cyanomethylphenyl | |
| 3.99 | Me | 3-cyanomethoxyphenyl | |
| 3.100 | Me | 4-cyanomethylphenyl | |
| 3.101 | Me | 4-cyclohexylphenyl | |
| 3.102 | Me | 4-biphenylyl | |
| 3.103 | Me | 2-fluorenyl | |
| 3.104 | Me | 3-benzyloxyphenyl | |
| 3.105 | Me | 4-benzyloxyphenyl | |
| 3.106 | Me | 3,5-dibenzyloxyphenyl | |
| 3.107 | Me | 4-bromo-2-fluorophenyl | |
| 3.108 | Me | 4-bromo-3-methylphenyl | |
| 3.109 | Me | 6-(2,2-difluoro-1,4-benzo-dioxanyl) | |
| 3.110 | Me | 6-(2,2,3-trifluoro-1,4-benzodioxanyl) | |
| 3.111 | Me | pentafluorophenyl | |
| 3.112 | Me | 3-F,5-CF₃-phenyl | |
| 3.113 | Me | 3-OMe,5-CF₃-phenyl | |
| 3.114 | Me | 3-NO₂,5-CF₃-phenyl | |
| 3.115 | Me | 4-Br,3-CF₃-phenyl | |
| 3.116 | Me | 4-tert-butylphenyl | |
| 3.117 | Me | 4-sec-butylphenyl | |
| 3.118 | Me | 4-butylphenyl | |
| 3.119 | Me | 4-butoxyphenyl | |
| 3.120 | Me | 3-F,4-MeO-phenyl | 423(18)/241 |
| 3.121 | Me | 3-Cl,4-MeO-phenyl | |
| 3.122 | Me | 3-Cl,4-Me-phenyl | |
| 3.123 | Me | 4-Cl,2-Me-phenyl | |
| 3.124 | Me | 4-Cl,3-Me-phenyl | |
| 3.125 | Me | 5-Cl,2-Me-phenyl | |
| 3.126 | Me | 4-Cl,3-NO₂-phenyl | |
| 3.127 | Me | 5-indanyl | |
| 3.128 | Me | 3,5-dinitrophenyl | |
| 3.129 | Me | 2-nitrophenyl | |
| 3.130 | Me | 3-nitrophenyl | |
| 3.131 | Me | 4-nitrophenyl | |
| 3.132 | Me | 2-ethylphenyl | |
| 3.133 | Me | 3-ethylphenyl | |
| 3.134 | Me | 4-ethylphenyl | |
| 3.135 | Me | 3-ethoxyphenyl | |
| 3.136 | Me | 4-ethoxyphenyl | |
| 3.137 | Me | 3-F,4-CH₃-phenyl | |
| 3.138 | Me | 4-F,3-NO₂-phenyl | |
| 3.139 | Me | 4-Cl,3-CF₃-phenyl | |
| 3.140 | Et | 3-hydroxyphenyl | |
| 3.141 | Me | 4-hydroxyphenyl | |
| 3.142 | Me | 3-hydroxy-4-methoxyphenyl | |
| 3.143 | Me | 4-hydroxy-3-methylphenyl | |
| 3.144 | Me | 4-hydroxy-3-nitrophenyl | |
| 3.145 | Me | 4-isopropylphenyl | |
| 3.146 | Me | 3-iodophenyl | |
| 3.147 | Me | 4-iodophenyl | |
| 3.148 | Me | 3-mercaptophenyl | |
| 3.149 | Me | 4-mercaptophenyl | |
| 3.150 | Me | 2-NH₂C(S)-phenyl | |
| 3.151 | Me | 3-NH₂C(S)-phenyl | |
| 3.152 | Me | 4-NH₂C(S)-phenyl | |
| 3.153 | Me | 3-methylmercaptophenyl | |
| 3.154 | Me | 4-methylmercaptophenyl | |
| 3.155 | Me | 2-methylthio-5-CF₃-phenyl | |
| 3.156 | Me | 4-CH₃,3-NO₂-phenyl | |
| 3.157 | Me | 4-CH₃,2-NO₂-phenyl | |
| 3.158 | Me | 2-CH₃,4-NO₂-phenyl | |
| 3.159 | Me | 2-CH₃,5-NO₂-phenyl | |
| 3.160 | Me | 4-methoxy,3-NO₂-phenyl | |
| 3.161 | Me | 4-(4-morpholino)phenyl | |
| 3.162 | Me | 3-phenoxyphenyl | |
| 3.163 | Me | 4-phenoxyphenyl | |
| 3.164 | Me | 4-propylphenyl | |
| 3.165 | Me | 3-methanesulfinylmethyl-4-MeO-phenyl | |
| 3.166 | Me | 4-sulfamoylphenyl | |
| 3.167 | Me | 4-MeO,3-CH₃SCH₂-phenyl | |
| 3.168 | Me | 3-trifluoromethylsulfonyl-phenyl | |
| 3.169 | Me | 3-rhodanophenyl | |
| 3.170 | Me | 4-rhodanophenyl | |
| 3.171 | Me | 3-rhodanomethylphenyl | |
| 3.172 | Me | 4-rhodanomethylphenyl | |
| 3.173 | Me | 3-prop-1-en-3-yloxyphenyl | |
| 3.174 | Me | 2-cyclopropylmethoxyphenyl | |
| 3.175 | Me | 2,3,4,5-tetrafluorophenyl | |
| 3.176 | Me | 2,3,5,6-tetrafluorophenyl | |
| 3.177 | Me | 2,3,4-trimethoxyphenyl | |
| 3.178 | Me | 3,4,5-trimethoxyphenyl | |

TABLE 3-continued

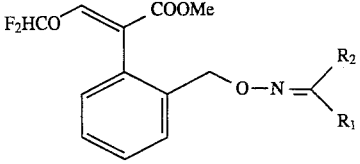
(Ib)

| | | |
|---|---|---|
| 3.179 | Me | 5,6,7,8-tetrahydro-1-naphthyl |
| 3.180 | Me | 2,3-dihydrobenzofur-5-yl |
| 3.181 | Me | 2,3-dihydrobenzofur-6-yl |
| 3.182 | Me | 7-OMe,2,3-dihydrobenzo-fur-5-yl |
| 3.183 | Me | 3-trimethylsilylphenyl |
| 3.184 | CF$_3$ | 3-trimethylsilylphenyl |
| 3.185 | Me | benzyl |
| 3.186 | Me | 3-CF$_3$-benzyl |
| 3.187 | Me | 4-chlorobenzyl |
| 3.188 | Me | 3-CF$_3$,4-chlorobenzyl |
| 3.189 | Me | phenoxymethyl |
| 3.190 | Me | 3-chlorophenoxymethyl |
| 3.191 | Me | 3-CF$_3$-phenoxymethyl |
| 3.192 | Me | 2-methoxy-5-benzodioxolyl |
| 3.193 | Me | 2-methyl-5-benzodioxolyl |
| 3.194 | Me | 2-phenyl-5-benzodioxolyl |
| 3.195 | Me | 3-methoxycarbonyl-phenyl |
| 3.196 | Me | 4-methoxycarbonyl-phenyl |
| 3.197 | Me | 3-methoximinomethyl-phenyl |
| 3.198 | Me | 3-ethoximinomethyl-phenyl |
| 3.199 | Me | 4-methoximinomethyl-phenyl |
| 3.200 | Me | 2-pyrazinyl |
| 3.201 | Me | 3,5-dimethyl-pyrazin-2-yl |
| 3.202 | Me | 3-ethoxy-pyrazin-2-yl |
| 3.203 | Me | 5-CONHCH$_3$-pyrazin-2-yl |
| 3.204 | Me | 2-pyrimidinyl |
| 3.205 | Me | 4-chloro-pyrimidin-2-yl |
| 3.206 | Me | 4-ethoxy-pyrimidin-2-yl |
| 3.207 | Me | 4-methoxy-pyrimidin-2-yl |
| 3.208 | Me | 4-(2,2,2-trifluoroethoxy)-pyrimidin-2-yl |
| 3.209 | Me | 2-SCH$_3$-pyrimidin-4-yl |
| 3.210 | Me | 4-isopropoxy-pyrimidin-2-yl |
| 3.211 | Me | 4,6-dimethyl-pyrimidin-2-yl |
| 3.212 | Me | 4-Me,6-cyclopropyl-pyrimidin-2-yl |
| 3.213 | Me | 4,6-diethoxy-pyrimidin-2-yl |
| 3.214 | Me | 4-Me,6-OMe-pyrimidin-2-yl |
| 3.215 | Me | 4-Me,6-CF$_3$-pyrimidin-2-yl |
| 3.216 | Me | 2-pyridyl |
| 3.217 | Me | 3-pyridyl |
| 3.218 |  | 4-pyridyl |
| 3.219 | Me | 2,6-dichloro-4-pyridyl |
| 3.220 | Me | 2-chloro-4-pyridyl |
| 3.221 | Me | 2-quinolinyl |
| 3.222 | Me | 6-quinolinyl |
| 3.223 | Me | 7-quinolinyl |
| 3.224 | Me | 5-isoquinolinyl |
| 3.225 | Me | 2-benzimidazolyl |
| 3.226 | Me | 3,4-benzocumarin-6-yl |
| 3.227 | Me | 2-thienyl |
| 3.228 | Me | 3-methylbenzo(b)thien-2-yl |
| 3.229 | Me | 5-chlorothien-2-yl |
| 3.230 | Me | 5-bromothien-2-yl |
| 3.231 | Me | 2-methoxycarbonyl-3-thienyl |
| 3.232 | Me | 2-furyl |
| 3.233 | Me | benzo[b]fur-2-yl |
| 3.234 | Me | 1-methylpyrrol-2-yl |
| 3.235 | Me | 4-methylthien-2-yl |
| 3.236 | Me | 5-methylfur-2-yl |
| 3.237 | Me | 6-bromo-2-pyridyl |
| 3.238 | Me | 4-trifluoromethyl-2-pyridyl |
| 3.239 | Me | 4-ethoxy-pyrimidin-2-yl |
| 3.240 | Me | 5-chloro-2-pyridyl |
| 3.241 | Me | 5-bromo-2-pyridyl |
| 3.242 | Me | 6-trifluoromethyl-2-pyridyl |
| 3.243 | Me | 6-quinoxalinyl |
| 3.244 | Me | 2-quinoxalinyl |
| 3.245 | Me | 6-chloro-2-quinoxalinyl |
| 3.246 | Me | 2-thiazolyl |
| 3.247 | Me | 5-trifluoromethyl-2-pyridyl |
| 3.248 | Me | 2,1,3-benzothiadiazol-5-yl |
| 3.249 | Me | 2,1,3-benzoxadiazol-5-yl |
| 3.250 | Me | 4-CN-2-pyridyl |
| 3.251 | Me | 5-bromo-3-pyridyl |
| 3.252 | Me | 6-methyl-3-pyridyl |
| 3.253 | Me | 1-morpholinyl |
| 3.254 | Me | 1-(2,6-dimethylmorpholinyl) |
| 3.255 | Me | 1-(2-methylmorpholinyl) |
| 3.256 | Me | 1-piperidinyl |
| 3.257 | Me | 1-piperazinyl |
| 3.258 | Me | methyl |
| 3.259 | Me | ethyl |
| 3.260 | Me | propyl |
| 3.261 | Me | isopropyl |
| 3.262 | Me | cyclopropyl |
| 3.263 | 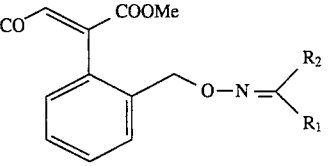 | cyclopropyl |
| 3.264 | CN | isopropyl |
| 3.265 | CN | cyclopropyl |
| 3.266 | CN | phenyl |
| 3.267 | Me | 4-Me,3-pentenyl | 381(3.1)/82 |
| 3.268 | Me | 4-Me,3-heptenyl | 409(7.65)/95 |
| 3.269 | Me | 4,6-Me$_2$,3-heptenyl | 423(6.05)/109 |
| 3.270 | Me | 4,8-Me$_2$;3,7-nonadienyl | 449(3.5)/69 |
| 3.271 | Me | 4-MeO-2,3,5,6-tetrafluoro-phenyl | |
| 3.272 | Me | 5-benzofurazanyl | |

| Ex. No. | N=C(R$_1$)R$_2$ | Phys. data |
|---|---|---|
| 3.273 | 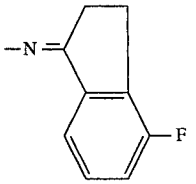 | |
| 3.274 | 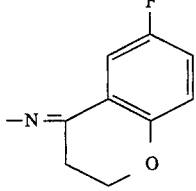 | |
| 3.275 | 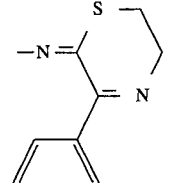 | |

TABLE 3-continued
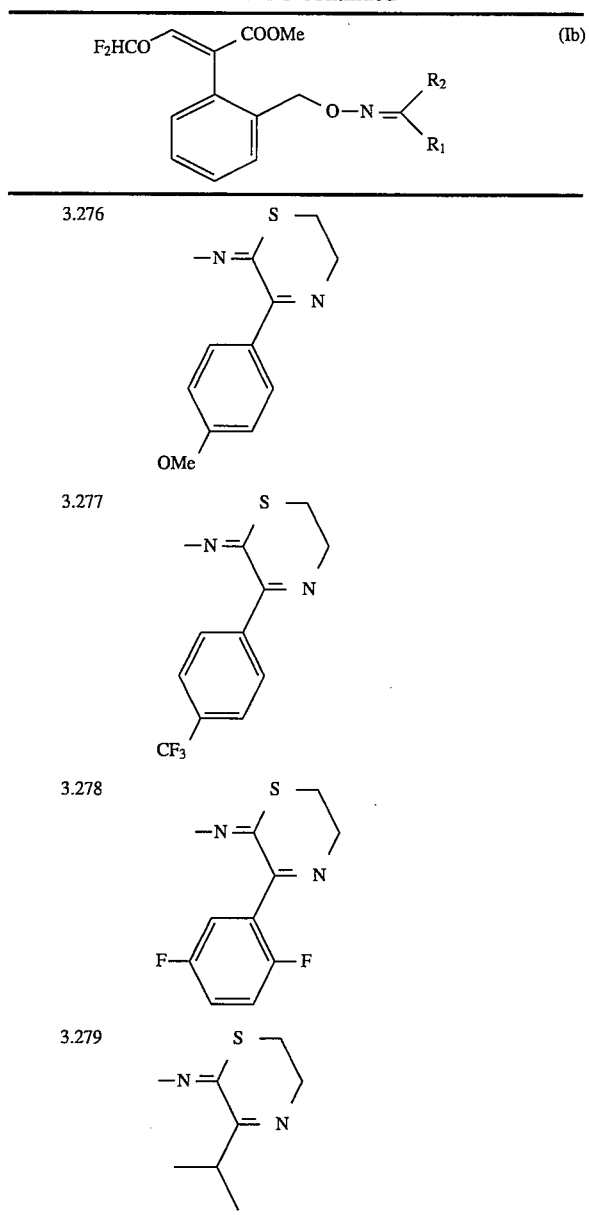
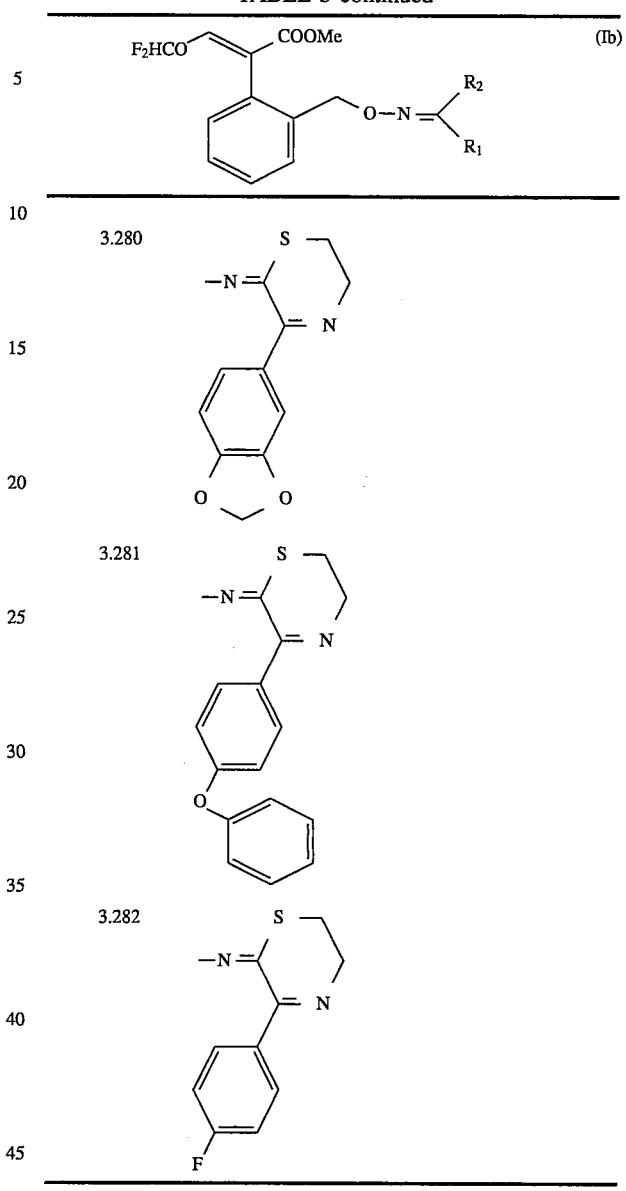
TABLE 4
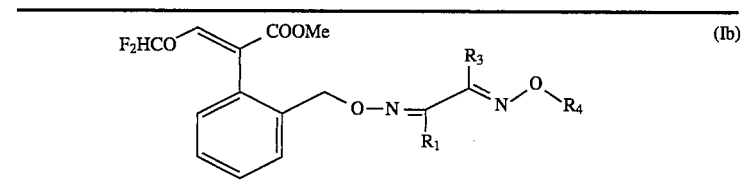
| Ex. No. | $R_1$ | $R_3$ | $R_4$ | Phys. data m.p. or MS: mol. peak (%) base peak |
|---|---|---|---|---|
| 4.1 | Me | Me | Me | 370(14)/241 |
| 4.2 | Δ | Me | Me | |
| 4.3 | Me | Δ | Me | |
| 4.4 | Me | Me | phenyl | |
| 4.5 | Me | Δ | phenyl | |
| 4.6 | Me | Me | benzyl | |

TABLE 4-continued $$\text{(Ib)}$$

Structure: F₂HCO-CH=C(COOMe)-C₆H₄-CH₂-O-N=C(R₁)-C(R₃)=N-O-R₄

| Ex. No. | R₁ | R₃ | R₄ | Phys. data m.p. or MS: mol. peak (%) base peak |
|---|---|---|---|---|
| 4.7 | Me | Me | Et | |
| 4.8 | Δ | Me | Et | |
| 4.9 | Me | Δ | Et | |
| 4.10 | H | Me | methoxymethyl | |
| 4.11 | Me | Me | methoxymethyl | |
| 4.12 | Me | Δ | methoxymethyl | |
| 4.13 | Δ | Me | methoxymethyl | |
| 4.14 | Me | Me | ethoxymethyl | |
| 4.15 | H | Me | cyanomethyl | |
| 4.16 | Me | Me | cyanomethyl | |
| 4.17 | Δ | Me | cyanomethyl | |
| 4.18 | H | Me | tert-butyl | |
| 4.19 | Me | Me | tert-butyl | |
| 4.20 | Me | Me | propargyl | |
| 4.21 | Δ | Me | propargyl | |
| 4.22 | Me | Δ | propargyl | |
| 4.23 | Me | Me | 2,2-dichlorocyclopropylmethyl | |
| 4.24 | Δ | Me | 2,2-dichlorocyclopropylmethyl | |
| 4.25 | H | Me | allyl | |
| 4.26 | Me | Me | allyl | 396(10)/241 |
| 4.27 | Me | Me | CF₃CH₂ | 438(1.5)/59 |
| 4.28 | Δ | Me | CF₃CH₂ | |
| 4.29 | Me | Me | CF₃CH₂CH₂ | |
| 4.30 | Me | Me | CF₃CH₂CH₂CH₂ | |
| 4.31 | Δ | Me | CF₃CH₂CH₂CH₂ | |
| 4.32 | Me | Me | 2-chloro-2-propenyl | |
| 4.33 | Δ | Me | 2-chloro-2-propenyl | |
| 4.34 | Me | Me | propyl | |
| 4.35 | Me | Me | butyl | |
| 4.36 | Me | Me | hexyl | |
| 4.37 | Me | Me | methoxycarbonylmethyl | |
| 4.38 | Me | Me | 3-fluorobenzyl | |
| 4.39 | Me | Me | 4-chlorobenzyl | |
| 4.40 | Me | Me | 2-chloobenzyl | |
| 4.41 | Me | Me | 2-CF₃-benzyl | |
| 4.42 | Me | Me | 3-CF₃-benzyl | |
| 4.43 | Me | Me | 4-CF₃-benzyl | |
| 4.44 | Me | Me | 3,4-dichlorobenzyl | |
| 4.45 | Me | Me | 2,4,6-trimethylbenzyl | |
| 4.46 | Me | Me | 4-chloro-2-nitrobenzyl | |
| 4.47 | Me | Me | 3-methoxybenzyl | |
| 4.48 | Me | Me | 2-phenethyl | |
| 4.49 | Me | Me | 3-phenylpropyl | |
| 4.50 | Me | Me | 2-(4-nitrophenyl)ethyl | |
| 4.51 | Me | Me | 2-(2-CF₃-phenyl)ethyl | |
| 4.52 | Me | Me | 2-(4-methoxyphenyl)ethyl | |
| 4.53 | Me | Me | 2-chloro-6-fluorobenzyl | |
| 4.54 | Me | Me | 3,4-methylenedioxybenzyl | |
| 4.55 | Me | Me | 2-cyanobenzyl | |
| 4.56 | Me | Me | 2-(4-chlorophenyl)ethyl | |
| 4.57 | Me | Me | cyclopropylmethyl | 410(5.55)/55 |
| 4.58 | Me | Me | 2-(1,3-dioxolanyl)methyl | |
| 4.59 | Me | Me | 2,2,3,3-tetrafluorocyclobutylmethyl | |
| 4.60 | Me | Me | α-fluoro-ethoxycarbonylmethyl | |
| 4.61 | Me | 3-CF₃-phenyl | Me | |
| 4.62 | Me | 4-chlorophenyl | Me | |
| 4.63 | Me | 3-chlorophenyl | Me | |
| 4.64 | Me | 2-fluorophenyl | Me | |
| 4.65 | Me | 4-methylphenyl | Me | |
| 4.66 | Me | 4-methoxy- | Me | |

TABLE 4-continued $$\text{(Ib)}$$

Structure: F$_2$HCO and COOMe on vinyl attached to phenyl ring with -CH$_2$-O-N=C(R$_1$)-C(R$_3$)=N-O-R$_4$ substituent

| Ex. No. | R$_1$ | R$_3$ | R$_4$ | Phys. data m.p. or MS: mol. peak (%) base peak |
|---|---|---|---|---|
| 4.67 | Me | 4-bromo-phenyl | Me | |
| 4.68 | Me | 2-thienyl | Me | |
| 4.69 | Me | 4-fluoro-phenyl | Me | |
| 4.70 | Me | 3-fluoro-5-CF$_3$-phenyl | Me | |
| 4.71 | Me | phenyl | Me | |
| 4.72 | Me | 2-methyl-phenyl | Me | |
| 4.73 | Me | 3-bromo-phenyl | Me | |
| 4.74 | Me | 3,4-methylene-dioxyphenyl | Me | |
| 4.75 | Me | 4-methyl-phenyl | Et | |
| 4.76 | Me | Δ | CH$_2$CH$_2$F | |
| 4.77 | Δ | Me | CH$_2$CH$_2$F | |
| 4.78 | Me | Me | CH$_2$CH$_2$F | 402(8)/241 |
| 4.79 | Me | 4-allyloxy-phenyl | Me | 488(18)/241 |
| 4.80 | SMe | 4-methyl-phenyl | Me | |
| 4.81 | Et | 4-methyl-phenyl | Me | |
| 4.82 | Me | 4-isobutyl-phenyl | Me | |
| 4.83 | Me | 4-propargyl-oxyphenyl | Me | |
| 4.84 | Me | 4-(2,2,2-tri-fluoroethoxy)-phenyl | Me | |
| 4.85 | Me | 4-ethoxy-phenyl | Me | |
| 4.86 | CN | 4-methyl-phenyl | Me | |
| 4.87 | CN | 4-Cl-phenyl | Me | |
| 4.88 | CN | 3,4-dichloro-phenyl | Me | |
| 4.89 | CN | 4-trifluoro-methoxyphenyl | Me | |
| 4.90 | Me | 3-EtO-phenyl | Me | |
| 4.91 | Me | 3-propoxy-phenyl | Me | |
| 4.92 | Me | 4-propoxy-phenyl | Me | |
| 4.93 | Me | 3-MeS-phenyl | Me | |
| 4.94 | Me | 4-MeS-phenyl | Me | |
| 4.95 | Me | 3-propyl-S-phenyl | Me | |
| 4.96 | Me | 4-propyl-S-phenyl | Me | |
| 4.97 | Me | 4-(3-F-phen-oxy)-phenyl | Me | |
| 4.98 | Me | 4-(4-F-phen-oxy)-phenyl | Me | |
| 4.99 | Me | 3-EtS-phenyl | Me | |
| 4.100 | Me | 4-EtS-phenyl | Me | |
| 4.101 | Me | 4-EtO-phenyl | Me | |
| 4.102 | CN | 3-trifluoro-methylphenyl | Me | |
| 4.103 | CN | 2-chloro-phenyl | Me | |
| 4.104 | CN | 4-fluoro-phenyl | Me | |

TABLE 5

| Ex. No. | R₁ | R₂ | Phys. data MS: mol. peak (%) base peak |
|---|---|---|---|
| 5.1 | Me | phenyl | |
| 5.2 | Me | 2-fluorophenyl | |
| 5.3 | Me | 3-fluorophenyl | |
| 5.4 | Me | 4-fluorophenyl | |
| 5.5 | ▷ | 4-fluorophenyl | |
| 5.6 | Me | 3-chlorophenyl | |
| 5.7 | ▷ | 3-chlorophenyl | |
| 5.8 | Me | 4-chlorophenyl | |
| 5.9 | Me | 2-bromophenyl | |
| 5.10 | Me | 3-bromophenyl | |
| 5.11 | Me | 4-bromophenyl | |
| 5.12 | ▷ | 4-bromophenyl | |
| 5.13 | ▷ | 4-chlorophenyl | 418(6.5)/116 |
| 5.14 | CH₃S | 4-chlorophenyl | |
| 5.15 | CH₃O | 4-chlorophenyl | |
| 5.16 | CH₃OCH₂ | 4-chlorophenyl | |
| 5.17 | CH₃SCH₂ | 4-chlorophenyl | |
| 5.18 | CF₃ | 4-chlorophenyl | |
| 5.19 | CN | 4-chlorophenyl | |
| 5.20 | Et | 4-chlorophenyl | |
| 5.21 | propyl | 4-chlorophenyl | |
| 5.22 | isopropyl | 4-chlorophenyl | |
| 5.23 | Me | 2,4-difluorophenyl | |
| 5.24 | Me | 3,4-difluorophenyl | |
| 5.25 | Me | 2,3-difluorophenyl | |
| 5.26 | Me | 2,5-difluorophenyl | |
| 5.27 | Me | 3,5-difluorophenyl | |
| 5.28 | Me | 2,4-dichlorophenyl | |
| 5.29 | Me | 3,4-dichlorophenyl | |
| 5.30 | Me | 2,5-dichlorophenyl | |
| 5.31 | Me | 3,5-dichlorophenyl | |
| 5.32 | Me | 3-Cl,4-F-phenyl | |
| 5.33 | Me | 4-Cl,2-F-phenyl | |
| 5.34 | Me | 2,3,4-trifluorophenyl | |
| 5.35 | Me | 2,3,6-trifluorophenyl | |
| 5.36 | Me | 2,4,6-trifluorophenyl | |
| 5.37 | Me | 2,4,5-trifluorophenyl | |
| 5.38 | Me | 2,3,4-trichlorophenyl | |
| 5.39 | Me | 3,4,5-trichlorophenyl | |
| 5.40 | Me | 2,4,5-trichlorophenyl | |
| 5.41 | Me | 1-naphthyl | |
| 5.42 | Me | 2-naphthyl | |
| 5.43 | ▷ | 2-naphthyl | |
| 5.44 | Me | 2-methylphenyl | |
| 5.45 | Me | 3-methylphenyl | |
| 5.46 | Me | 4-methylphenyl | |
| 5.47 | ▷ | 4-methylphenyl | |
| 5.48 | Me | 2,3-dimethylphenyl | |
| 5.49 | Me | 2,4-dimethylphenyl | |
| 5.50 | Me | 2,4-dimethylphenyl | |
| 5.51 | Me | 3,4-dimethylphenyl | |
| 5.52 | Me | 3,5-dimethylphenyl | |
| 5.53 | Me | 2-methoxyphenyl | |
| 5.54 | Me | 3-methoxyphenyl | |
| 5.55 | Me | 4-methoxyphenyl | |
| 5.56 | Me | 3,4-dimethoxyphenyl | |
| 5.57 | Me | 3,5-dimethoxyphenyl | |
| 5.58 | Me | 3,4-methylenedioxyphenyl | 402(14)/162 |
| 5.59 | ▷ | 3,4-methylenedioxyphenyl | |
| 5.60 | SMe | 3,4-methylenedioxyphenyl | |
| 5.61 | OMe | 3,4-methylenedioxyphenyl | |
| 5.62 | Me | 3,4-ethylenedioxyphenyl | |
| 5.63 | ▷ | 3,4-ethylenedioxyphenyl | |
| 5.64 | Me | 2,2-difluoro-5-benzodioxolyl | |
| 5.65 | Et | 2,2-difluoro-5-benzodioxolyl | |
| 5.66 | Me | 3-difluoromethoxyphenyl | 423(5)/223 |
| 5.67 | Me | 4-difluoromethoxyphenyl | |
| 5.68 | Me | 3-(2,2,2-trifluoroethoxy)-phenyl | |
| 5.69 | Me | 3-(1,1,2,2-tetrafluoro-ethoxy)-phenyl | |
| 5.70 | Me | 3-(1,1,2,3,3,3-hexafluoro-propoxy)phenyl | |
| 5.71 | Me | 4-(2,2,2-trifluoroethoxy)-phenyl | |
| 5.72 | Me | 4-(1,1,2,2-tetrafluoro-ethoxy)-phenyl | |
| 5.73 | Me | 3-trifluoromethoxyphenyl | |
| 5.74 | Me | 4-trifluoromethoxyphenyl | |
| 5.75 | Me | 2-trifluoromethylphenyl | |
| 5.76 | Me | 3-trifluoromethylphenyl | 426(2)/116 |
| 5.77 | ▷ | 3-trifluoromethylphenyl | |
| 5.78 | Et | 3-trifluoromethylphenyl | |
| 5.79 | CN | 3-trifluoromethylphenyl | |
| 5.80 | OMe | 3-trifluoromethylphenyl | |
| 5.81 | SMe | 3-trifluoromethylphenyl | |
| 5.82 | CH₂OCH₃ | 3-trifluoromethylphenyl | |
| 5.83 | Me | 3,5-bis(trifluoromethyl)-phenyl | |
| 5.84 | Me | 4-F,3-CF₃-phenyl | |
| 5.85 | ▷ | 4-F,3-CF₃-phenyl | |
| 5.86 | Me | 2-Cl,5-CF₃-phenyl | |
| 5.87 | Me | 3,5-dichloro-2-fluoro-4-methoxy-phenyl | |
| 5.88 | Me | 3,5-dichloro-2,4-dimethoxy-phenyl | |
| 5.89 | Me | 3-acetylphenyl | |
| 5.90 | Me | 4-acetylphenyl | |
| 5.91 | Me | 3-carboxyphenyl | |
| 5.92 | Me | 4-carboxyphenyl | |
| 5.93 | Me | 3-carbethoxyphenyl | |
| 5.94 | Me | 4-carbethoxyphenyl | |
| 5.95 | Me | 2-cyanophenyl | |
| 5.96 | Me | 3-cyanophenyl | |
| 5.97 | Me | 4-cyanophenyl | |

TABLE 5-continued

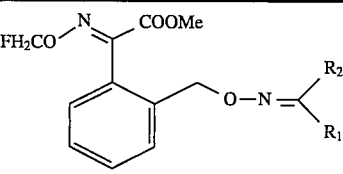

(Ic)

| | | |
|---|---|---|
| 5.98 | Me | 3-cyanomethylphenyl |
| 5.99 | Me | 3-cyanomethoxyphenyl |
| 5.100 | Me | 4-cyanomethylphenyl |
| 5.101 | Me | 4-cyclohexylphenyl |
| 5.102 | Me | 4-biphenylyl |
| 5.103 | Me | 2-fluorenyl |
| 5.104 | Me | 3-benzyloxyphenyl |
| 5.105 | Me | 4-benzyloxyphenyl |
| 5.106 | Me | 3,5-dibenzyloxyphenyl |
| 5.107 | Me | 4-bromo-2-fluorophenyl |
| 5.108 | Me | 4-bromo-3-methylphenyl |
| 5.109 | Me | 6-(2,2-difluoro-1,4-benzodioxanyl) |
| 5.110 | Me | 6-(2,2,3-trifluoro-1,4-benzodioxanyl) |
| 5.111 | Me | pentafluorophenyl |
| 5.112 | Me | 3-F,5-CF$_3$-phenyl |
| 5.113 | Me | 3-OMe,5-CF$_3$-phenyl |
| 5.114 | Me | 3-NO$_2$,5-CF$_3$-phenyl |
| 5.115 | Me | 4-Br,3-CF$_3$-phenyl |
| 5.116 | Me | 4-tert-butylphenyl |
| 5.117 | Me | 4-sec-butylphenyl |
| 5.118 | Me | 4-butylphenyl |
| 5.119 | Me | 4-butoxyphenyl |
| 5.120 | Me | 3-F,4-MeO-phenyl |
| 5.121 | Me | 3-Cl,4-MeO-phenyl |
| 5.122 | Me | 3-Cl,4-Me-phenyl |
| 5.123 | Me | 4-Cl,2-Me-phenyl |
| 5.124 | Me | 4-Cl,3-Me-phenyl |
| 5.125 | Me | 5-Cl,2-Me-phenyl |
| 5.126 | Me | 4-Cl,3-NO$_2$-phenyl |
| 5.127 | Me | 5-indanyl |
| 5.128 | Me | 3,5-dinitrophenyl |
| 5.129 | Me | 2-nitrophenyl |
| 5.130 | Me | 3-nitrophenyl |
| 5.131 | Me | 4-nitrophenyl |
| 5.132 | Me | 2-ethylphenyl |
| 5.133 | Me | 3-ethylphenyl |
| 5.134 | Me | 4-ethylphenyl |
| 5.135 | Me | 3-ethoxyphenyl |
| 5.136 | Me | 4-ethoxyphenyl |
| 5.137 | Me | 3-F,4-CH$_3$-phenyl |
| 5.138 | Me | 4-F,3-NO$_2$-phenyl |
| 5.139 | Me | 4-Cl,3-CF$_3$-phenyl |
| 5.140 | Et | 3-hydroxyphenyl |
| 5.141 | Me | 4-hydroxyphenyl |
| 5.142 | Me | 3-hydroxy-4-methoxyphenyl |
| 5.143 | Me | 4-hydroxy-3-methylphenyl |
| 5.144 | Me | 4-hydroxy-3-nitrophenyl |
| 5.145 | Me | 4-isopropylphenyl |
| 5.146 | Me | 3-iodophenyl |
| 5.147 | Me | 4-iodophenyl |
| 5.148 | Me | 3-mercaptophenyl |
| 5.149 | Me | 4-mercaptophenyl |
| 5.150 | Me | 2-NH$_2$C(S)-phenyl |
| 5.151 | Me | 3-NH$_2$C(S)-phenyl |
| 5.152 | Me | 4-NH$_2$C(S)-phenyl |
| 5.153 | Me | 3-methylmercaptophenyl |
| 5.154 | Me | 4-methylmercaptophenyl |
| 5.155 | Me | 2-methylthio-5-CF$_3$-phenyl |
| 5.156 | Me | 4-CH$_3$,3-NO$_2$-phenyl |
| 5.157 | Me | 4-CH$_3$,2-NO$_2$-phenyl |
| 5.158 | Me | 2-CH$_3$,4-NO$_2$-phenyl |
| 5.159 | Me | 2-CH$_3$,5-NO$_2$-phenyl |
| 5.160 | Me | 4-methoxy,3-NO$_2$-phenyl |
| 5.161 | Me | 4-(4-morpholino)phenyl |
| 5.162 | Me | 3-phenoxyphenyl |
| 5.163 | Me | 4-phenoxyphenyl |
| 5.164 | Me | 4-propylphenyl |
| 5.165 | Me | 3-methanesulfinylmethyl-4-MeO-phenyl |
| 5.166 | Me | 4-sulfamoylphenyl |
| 5.167 | Me | 4-MeO,3-CH$_3$SCH$_2$-phenyl |
| 5.168 | Me | 3-trifluoromethylsulfonyl-phenyl |
| 5.169 | Me | 3-rhodanophenyl |
| 5.170 | Me | 4-rhodanophenyl |
| 5.171 | Me | 3-rhodanomethylphenyl |
| 5.172 | Me | 4-rhodanomethylphenyl |
| 5.173 | Me | 3-prop-1-en-3-yloxyphenyl |
| 5.174 | Me | 2-cyclopropylmethoxyphenyl |
| 5.175 | Me | 2,3,4,5-tetrafluorophenyl |
| 5.176 | Me | 2,3,5,6-tetrafluorophenyl |
| 5.177 | Me | 2,3,4-trimethoxyphenyl |
| 5.178 | Me | 3,4,5-trimethoxyphenyl |
| 5.179 | Me | 5,6,7,8-tetrahydro-1-naphthyl |
| 5.180 | Me | 2,3-dihydrobenzofur-5-yl |
| 5.181 | Me | 2,3-dihydrobenzofur-6-yl |
| 5.182 | Me | 7-OMe,2,3-dihydrobenzofur-5-yl |
| 5.183 | Me | 3-trimethylsilylphenyl |
| 5.184 | CF$_3$ | 3-trimethylsilylphenyl |
| 5.185 | Me | benzyl |
| 5.186 | Me | 3-CF$_3$-benzyl |
| 5.187 | Me | 4-chlorobenzyl |
| 5.188 | Me | 3-CF$_3$,4-chlorobenzyl |
| 5.189 | Me | phenoxymethyl |
| 5.190 | Me | 3-chlorophenoxymethyl |
| 5.191 | Me | 3-CF$_3$-phenoxymethyl |
| 5.192 | Me | 2-methoxy-5-benzodioxolyl |
| 5.193 | Me | 2-methyl-5-benzodioxolyl |
| 5.194 | Me | 2-phenyl-5-benzodioxolyl |
| 5.195 | Me | 3-methoxycarbonyl-phenyl |
| 5.196 | Me | 4-methoxycarbonyl-phenyl |
| 5.197 | Me | 3-methoximinomethyl-phenyl |
| 5.198 | Me | 3-ethoximinomethyl-phenyl |
| 5.199 | Me | 4-methoximinomethyl-phenyl |
| 5.200 | Me | 2-pyrazinyl |
| 5.201 | Me | 3,5-dimethyl-pyrazin-2-yl |
| 5.202 | Me | 3-ethoxy-pyrazin-2-yl |
| 5.203 | Me | 5-CONHCH$_3$-pyrazin-2-yl |
| 5.204 | Me | 2-pyrimidinyl |
| 5.205 | Me | 4-chloro-pyrimidin-2-yl |
| 5.206 | Me | 4-ethoxy-pyrimidin-2-yl |
| 5.207 | Me | 4-methoxy-pyrimidin-2-yl |
| 5.208 | Me | 4-(2,2,2-trifluoroethoxy)-pyrimidin-2-yl |
| 5.209 | Me | 2-SCH$_3$-pyrimidin-4-yl |
| 5.210 | Me | 4-isopropoxy-pyrimidin-2-yl |
| 5.211 | Me | 4,6-dimethyl-pyrimidin-2-yl |
| 5.212 | Me | 4-Me,6-cyclopropyl-pyrimidin-2-yl |
| 5.213 | Me | 4,6-diethoxy-pyrimidin-2-yl |
| 5.214 | Me | 4-Me,6-OMe-pyrimidin-2-yl |
| 5.215 | Me | 4-Me,6-CF$_3$-pyrimidin-2-yl |
| 5.216 | Me | 2-pyridyl |
| 5.217 | Me | 3-pyridyl |
| 5.218 | 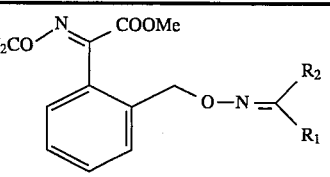 | 4-pyridyl |
| 5.219 | Me | 2,6-dichloro-4-pyridyl |
| 5.220 | Me | 2-chloro-4-pyridyl |
| 5.221 | Me | 2-quinolinyl |
| 5.222 | Me | 6-quinolinyl |
| 5.223 | Me | 7-quinolinyl |
| 5.224 | Me | 5-isoquinolinyl |
| 5.225 | Me | 2-benzimidazolyl |
| 5.226 | Me | 3,4-benzocumarin-6-yl |

TABLE 5-continued (Ic) structure: FH₂CO-N=C(COOMe)- attached to benzene with -CH₂-O-N=C(R₁)(R₂) substituent

| Ex. No. | R₁ | R₂ |
|---|---|---|
| 5.227 | Me | 2-thienyl |
| 5.228 | Me | 3-methylbenzo(b)thien-2-yl |
| 5.229 | Me | 5-chlorothien-2-yl |
| 5.230 | Me | 5-bromothien-2-yl |
| 5.231 | Me | 2-methoxycarbonyl-3-thienyl |
| 5.232 | Me | 2-furyl |
| 5.233 | Me | benzo[b]fur-2-yl |
| 5.234 | Me | 1-methylpyrrol-2-yl |
| 5.235 | Me | 4-methylthien-2-yl |
| 5.236 | Me | 5-methylfur-2-yl |
| 5.237 | Me | 6-bromo-2-pyridyl |
| 5.238 | Me | 4-trifluoromethyl-2-pyridyl |
| 5.239 | Me | 4-ethoxy-pyrimidin-2-yl |
| 5.240 | Me | 5-chloro-2-pyridyl |
| 5.241 | Me | 5-bromo-2-pyridyl |
| 5.242 | Me | 6-trifluoromethyl-2-pyridyl |
| 5.243 | Me | 6-quinoxalinyl |
| 5.244 | Me | 2-quinoxalinyl |
| 5.245 | Me | 6-chloro-2-quinoxalinyl |
| 5.246 | Me | 2-thiazolyl |
| 5.247 | Me | 5-trifluoromethyl-2-pyridyl |
| 5.248 | Me | 2,1,3-benzothiadiazol-5-yl |
| 5.249 | Me | 2,1,3-benzoxadiazol-5-yl |
| 5.250 | Me | 4-CN-2-pyridyl |
| 5.251 | Me | 5-bromo-3-pyridyl |
| 5.252 | Me | 6-methyl-3-pyridyl |
| 5.253 | Me | 1-morpholinyl |
| 5.254 | Me | 1-(2,6-dimethylmorpholinyl) |
| 5.255 | Me | 1-(2-methylmorpholinyl) |
| 5.256 | Me | 1-piperidinyl |
| 5.257 | Me | 1-piperazinyl |
| 5.258 | Me | methyl |
| 5.259 | Me | ethyl |
| 5.260 | Me | propyl |
| 5.261 | Me | isopropyl |
| 5.262 | Me | cyclopropyl |
| 5.263 | cyclopropyl | cyclopropyl |
| 5.264 | CN | isopropyl |
| 5.265 | CN | cyclopropyl |
| 5.266 | CN | phenyl |

| Ex. No. | N=C(R₁)R₂ | Phys. data |
|---|---|---|
| 5.267 | =N-(4-fluoroindan-1-ylidene) | |
| 5.268 | =N-(5-fluoro-chroman-4-ylidene) | |
| 5.269 | dihydrothiazine with 4-Cl-phenyl | |
| 5.270 | dihydrothiazine with 4-OMe-phenyl | |
| 5.271 | dihydrothiazine with 4-CF₃-phenyl | |
| 5.272 | dihydrothiazine with 2,5-difluorophenyl | |
| 5.273 | dihydrothiazine with isopropyl | |

TABLE 5-continued

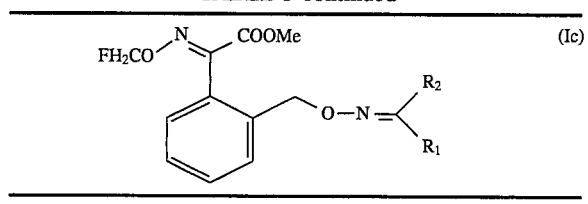

| 5.274 | 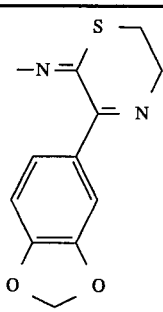 |
|---|---|
| 5.275 | 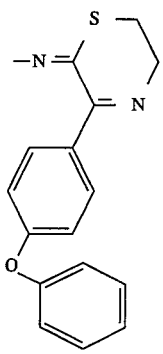 |

TABLE 5-continued

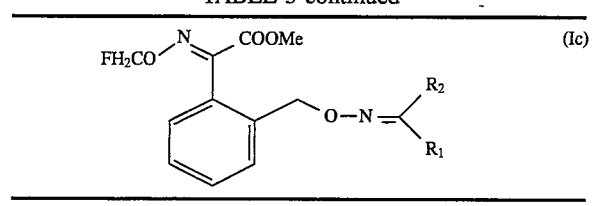

| 5.276 | 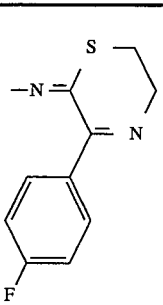 |
|---|---|

TABLE 6

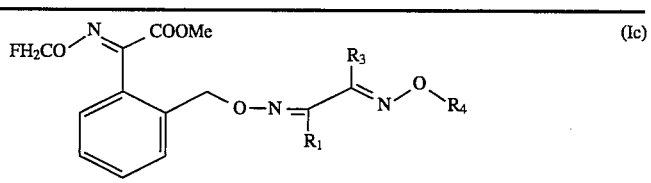

| Ex. No. | $R_1$ | $R_3$ | $R_4$ | Phys. data m.p. or MS: mol. peak (%) base peak |
|---|---|---|---|---|
| 6.1 | Me | Me | Me | |
| 6.2 | Δ | Me | Me | |
| 6.3 | Me | Δ | Me | |
| 6.4 | Me | Me | phenyl | |
| 6.5 | Me | Δ | phenyl | |
| 6.6 | Me | Me | benzyl | |
| 6.7 | Me | Me | Et | |
| 6.8 | Δ | Me | Et | |
| 6.9 | Me | Δ | Et | |
| 6.10 | H | Me | methoxymethyl | |
| 6.11 | Me | Me | methoxymethyl | |
| 6.12 | Me | Δ | methoxymethyl | |
| 6.13 | Δ | Me | methoxymethyl | |
| 6.14 | Me | Me | ethoxymethyl | |
| 6.15 | H | Me | cyanomethyl | |
| 6.16 | Me | Me | cyanomethyl | |
| 6.17 | Δ | Me | cyanomethyl | |
| 6.18 | H | Me | tert-butyl | |
| 6.19 | Me | Me | tert-butyl | |
| 6.20 | Me | Me | propargyl | |
| 6.21 | Δ | Me | propargyl | |
| 6.22 | Me | Δ | propargyl | |

TABLE 6-continued (Ic)

FH₂CO-N=C(COOMe)-C₆H₄-CH₂-O-N=C(R₁)-C(R₃)=N-O-R₄

| Ex. No. | R₁ | R₃ | R₄ | Phys. data m.p. or MS: mol. peak (%) base peak |
|---|---|---|---|---|
| 6.23 | Me | Me | 2,2-dichlorocyclopropylmethyl | |
| 6.24 | Δ | Me | 2,2-dichlorocyclopropylmethyl | |
| 6.25 | H | Me | allyl | |
| 6.26 | Me | Me | allyl | 396(10)/241 |
| 6.27 | Me | Me | CF₃CH₂ | |
| 6.28 | Δ | Me | CF₃CH₂ | |
| 6.29 | Me | Me | CF₃CH₂CH₂ | |
| 6.30 | Me | Me | CF₃CH₂CH₂CH₂ | |
| 6.31 | Δ | Me | CF₃CH₂CH₂CH₂ | |
| 6.32 | Me | Me | 2-chloro-2-propenyl | ¹H-NMR(CDCl₃)δppm: 1.95(s, 3H), 2.0(s, 3H), 3.85(s, 3H), 4.67 (s, 2H), 5.1(s, 2H), 5.36(m, 2H), 5.75(d, 2H), 7.25–7.5(m, 4H) |
| 6.33 | Δ | Me | 2-chloro-2-propenyl | |
| 6.34 | Me | Me | propyl | |
| 6.35 | Me | Me | butyl | |
| 6.36 | Me | Me | hexyl | |
| 6.37 | Me | Me | methoxycarbonylmethyl | |
| 6.38 | Me | Me | 3-fluorobenzyl | |
| 6.39 | Me | Me | 4-chlorobenzyl | |
| 6.40 | Me | Me | 2-chlorobenzyl | |
| 6.41 | Me | Me | 2-CF₃-benzyl | |
| 6.42 | Me | Me | 3-CF₃-benzyl | |
| 6.43 | Me | Me | 4-CF₃-benzyl | |
| 6.44 | Me | Me | 3,4-dichlorobenzyl | |
| 6.45 | Me | Me | 2,4,6-trimethylbenzyl | |
| 6.46 | Me | Me | 4-chloro-2-nitrobenzyl | |
| 6.47 | Me | Me | 3-methoxybenzyl | |
| 6.48 | Me | Me | 2-phenethyl | |
| 6.49 | Me | Me | 3-phenylpropyl | |
| 6.50 | Me | Me | 2-(4-nitrophenyl)ethyl | |
| 6.51 | Me | Me | 2-(2-CF₃-phenyl)ethyl | |
| 6.52 | Me | Me | 2-(4-methoxyphenyl)ethyl | |
| 6.53 | Me | Me | 2-chloro-6-fluorobenzyl | |
| 6.54 | Me | Me | 3,4-methylenedioxybenzyl | |
| 6.55 | Me | Me | 2-cyanobenzyl | |
| 6.56 | Me | Me | 2-(4-chlorophenyl)ethyl | |
| 6.57 | Me | Me | cyclopropylmethyl | 393(26)/55 |
| 6.58 | Me | Me | 2-(1,3-dioxolanyl)methyl | |
| 6.59 | Me | Me | 2,2,3,3-tetrafluorocyclobutylmethyl | |
| 6.60 | Me | Me | α-fluoro-ethoxycarbonylmethyl | |
| 6.61 | Me | 3-CF₃-phenyl | Me | |
| 6.62 | Me | 4-chlorophenyl | Me | |
| 6.63 | Me | 3-chlorophenyl | Me | |
| 6.64 | Me | 2-fluorophenyl | Me | |
| 6.65 | Me | 4-methylphenyl | Me | |
| 6.66 | Me | 4-methoxyphenyl | Me | |
| 6.67 | Me | 4-bromophenyl | Me | |
| 6.68 | Me | 2-thienyl | Me | |
| 6.69 | Me | 4-fluorophenyl | Me | |
| 6.70 | Me | 3-fluoro-5-CF₃-phenyl | Me | |
| 6.71 | Me | phenyl | Me | |
| 6.72 | Me | 2-methylphenyl | Me | |

TABLE 6-continued (Ic) structure: FH₂CO-N=C(COOMe)-C₆H₄-CH₂-O-N=C(R₁)-C(R₃)=N-O-R₄

| Ex. No. | R₁ | R₃ | R₄ | Phys. data m.p. or MS: mol. peak (%) base peak |
|---|---|---|---|---|
| 6.73 | Me | 3-bromophenyl | Me | |
| 6.74 | Me | 3,4-methylenedioxyphenyl | Me | |
| 6.75 | Me | 4-methylphenyl | Et | |
| 6.76 | Me | Δ | CH₂CH₂F | |
| 6.77 | Δ | Me | CH₂CH₂F | |
| 6.78 | Me | Me | CH₂CH₂F | 402(8)/241 |
| 6.79 | Me | 4-allyloxyphenyl | Me | 488(18)/241 |
| 6.80 | SMe | 4-methylphenyl | Me | |
| 6.81 | Et | 4-methylphenyl | Me | |
| 6.82 | Me | 4-isobutylphenyl | Me | |
| 6.83 | Me | 4-propargyloxyphenyl | Me | |
| 6.84 | Me | 4-(2,2,2-trifluoroethoxy)-phenyl | Me | |
| 6.85 | Me | 4-ethoxyphenyl | Me | |
| 6.86 | CN | 4-methylphenyl | Me | |
| 6.87 | CN | 4-chlorophenyl | Me | |
| 6.88 | CN | 3,4-dichlorophenyl | Me | |
| 6.89 | CN | 4-trifluoromethoxyphenyl | Me | |
| 6.90 | Me | 3-EtO-phenyl | Me | |
| 6.91 | Me | 3-propoxyphenyl | Me | |
| 6.92 | Me | 4-propoxyphenyl | Me | |
| 6.93 | Me | 3-MeS-phenyl | Me | |
| 6.94 | Me | 4-MeS-phenyl | Me | |
| 6.95 | Me | 3-propyl-S-phenyl | Me | |
| 6.96 | Me | 4-propyl-S-phenyl | Me | |
| 6.97 | Me | 4-(3-F-phenoxy)-phenyl | Me | |
| 6.98 | Me | 4-(4-F-phenoxy)-phenyl | Me | |
| 6.99 | Me | 3-EtS-phenyl | Me | |
| 6.100 | Me | 4-EtS-phenyl | Me | |
| 6.101 | Me | 4-EtO-phenyl | Me | |
| 6.102 | CN | 3-trifluoromethylphenyl | Me | |
| 6.103 | CN | 2-chlorophenyl | Me | |
| 6.104 | CN | 4-fluorophenyl | Me | |
| 6.105 | Me | Me | CH₂F | 75–79° C. |

TABLE 7

(Ie)

| Ex. No. | R₁ | R₂ | Phys. data MS: mol. peak (%) base peak |
|---|---|---|---|
| 7.1 | Me | phenyl | |
| 7.2 | Me | 2-fluorophenyl | |
| 7.3 | Me | 3-fluorophenyl | |
| 7.4 | Me | 4-fluorophenyl | |
| 7.5 | cyclopropyl | 4-fluorophenyl | |
| 7.6 | Me | 3-chlorophenyl | |
| 7.7 | cyclopropyl | 3-chlorophenyl | |
| 7.8 | Me | 4-chlorophenyl | |
| 7.9 | Me | 2-bromophenyl | |
| 7.10 | Me | 3-bromophenyl | |
| 7.11 | Me | 4-bromophenyl | |
| 7.12 | cyclopropyl | 4-bromophenyl | |
| 7.13 | cyclopropyl | 4-chlorophenyl | NMR(Ex. P-12) |
| 7.14 | CH₃S | 4-chlorophenyl | |
| 7.15 | CH₃O | 4-chlorophenyl | |
| 7.16 | CH₃OCH₂ | 4-chlorophenyl | |
| 7.17 | CH₃SCH₂ | 4-chlorophenyl | |
| 7.18 | CF₃ | 4-chlorophenyl | |
| 7.19 | CN | 4-chlorophenyl | |
| 7.20 | Et | 4-chlorophenyl | |
| 7.21 | propyl | 4-chlorophenyl | |
| 7.22 | isopropyl | 4-chlorophenyl | |
| 7.23 | Me | 2,4-difluorophenyl | |
| 7.24 | Me | 3,4-difluorophenyl | |
| 7.25 | Me | 2,3-difluorophenyl | |
| 7.26 | Me | 2,5-difluorophenyl | |
| 7.27 | Me | 3,5-difluorophenyl | |
| 7.28 | Me | 2,4-dichlorophenyl | |
| 7.29 | Me | 3,4-dichlorophenyl | |
| 7.30 | Me | 2,5-dichlorophenyl | |
| 7.31 | Me | 3,5-dichlorophenyl | |
| 7.32 | Me | 3-Cl,4-F-phenyl | |
| 7.33 | Me | 4-Cl,2-F-phenyl | |
| 7.34 | Me | 2,3,4-trifluorophenyl | |
| 7.35 | Me | 2,3,6-trifluorophenyl | |
| 7.36 | Me | 2,4,6-trifluorophenyl | |
| 7.37 | Me | 2,4,5-trifluorophenyl | |
| 7.38 | Me | 2,3,4-trichlorophenyl | |
| 7.39 | Me | 3,4,5-trichlorophenyl | |
| 7.40 | Me | 2,4,5-trichlorophenyl | |
| 7.41 | Me | 1-naphthyl | |
| 7.42 | Me | 2-naphthyl | |
| 7.43 | cyclopropyl | 2-naphthyl | |
| 7.44 | Me | 2-methylphenyl | |
| 7.45 | Me | 3-methylphenyl | |
| 7.46 | Me | 4-methylphenyl | |
| 7.47 | cyclopropyl | 4-methylphenyl | |
| 7.48 | Me | 2,3-dimethylphenyl | |
| 7.49 | Me | 2,4-dimethylphenyl | |
| 7.50 | Me | 2,5-dimethylphenyl | |
| 7.51 | Me | 3,4-dimethylphenyl | |
| 7.52 | Me | 3,5-dimethylphenyl | |
| 7.53 | Me | 2-methoxyphenyl | |
| 7.54 | Me | 3-methoxyphenyl | |
| 7.55 | Me | 4-methoxyphenyl | |
| 7.56 | Me | 3,4-dimethoxyphenyl | |
| 7.57 | Me | 3,5-dimethoxyphenyl | |
| 7.58 | Me | 3,4-methylenedioxyphenyl | 79–81° C. 401(12)/58 |
| 7.59 | cyclopropyl | 3,4-methylenedioxyphenyl | |
| 7.60 | SMe | 3,4-methylenedioxyphenyl | |
| 7.61 | OMe | 3,4-methylenedioxyphenyl | |
| 7.62 | Me | 3,4-ethylenedioxyphenyl | |
| 7.63 | cyclopropyl | 3,4-ethylenedioxyphenyl | |
| 7.64 | Me | 2,2-difluoro-5-benzodioxolyl | |
| 7.65 | Et | 2,2-difluoro-5-benzodioxolyl | |
| 7.66 | Me | 3-difluoromethoxyphenyl | |
| 7.67 | Me | 4-difluoromethoxyphenyl | |
| 7.68 | Me | 3-(2,2,2-trifluoroethoxy)-phenyl | |
| 7.69 | Me | 3-(1,1,2,2-tetrafluoro-ethoxy)-phenyl | |
| 7.70 | Me | 3-(1,1,2,3,3,3-hexafluoro-propoxy)phenyl | |
| 7.71 | Me | 4-(2,2,2-trifluoroethoxy)-phenyl | |
| 7.72 | Me | 4-(1,1,2,2-tetrafluoro-ethoxy)-phenyl | |
| 7.73 | Me | 3-trifluoromethoxyphenyl | |
| 7.74 | Me | 4-trifluoromethoxyphenyl | |
| 7.75 | Me | 2-trifluoromethylphenyl | |
| 7.76 | Me | 3-trifluoromethylphenyl | 425(0.3)/116 |
| 7.77 | cyclopropyl | 3-trifluoromethylphenyl | |
| 7.78 | Et | 3-trifluoromethylphenyl | |
| 7.79 | CN | 3-trifluoromethylphenyl | |
| 7.80 | OMe | 3-trifluoromethylphenyl | |
| 7.81 | SMe | 3-trifluoromethylphenyl | |
| 7.82 | CH₂OCH₃ | 3-trifluoromethylphenyl | |
| 7.83 | Me | 3,5-bis(trifluoromethyl)-phenyl | |
| 7.84 | Me | 4-F,3-CF₃-phenyl | |
| 7.85 | cyclopropyl | 4-F,3-CF₃-phenyl | |
| 7.86 | Me | 2-Cl,5-CF₃-phenyl | |
| 7.87 | Me | 3,5-dichloro-2-fluoro-4-methoxy-phenyl | |
| 7.88 | Me | 3,5-dichloro-2,4-dimethoxy-phenyl | |
| 7.89 | Me | 3-acetylphenyl | |
| 7.90 | Me | 4-acetylphenyl | |
| 7.91 | Me | 3-carboxyphenyl | |
| 7.92 | Me | 4-carboxyphenyl | |
| 7.93 | Me | 3-carbethoxyphenyl | |
| 7.94 | Me | 4-carbethoxyphenyl | |
| 7.95 | Me | 2-cyanophenyl | |
| 7.96 | Me | 3-cyanophenyl | |

TABLE 7-continued

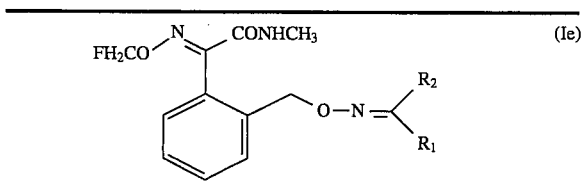

(Ie)

| | | |
|---|---|---|
| 7.97 | Me | 4-cyanophenyl |
| 7.98 | Me | 3-cyanomethylphenyl |
| 7.99 | Me | 3-cyanomethoxyphenyl |
| 7.100 | Me | 4-cyanomethylphenyl |
| 7.101 | Me | 4-cyclohexylphenyl |
| 7.102 | Me | 4-biphenylyl |
| 7.103 | Me | 2-fluorenyl |
| 7.104 | Me | 3-benzyloxyphenyl |
| 7.105 | Me | 4-benzyloxyphenyl |
| 7.106 | Me | 3,5-dibenzyloxyphenyl |
| 7.107 | Me | 4-bromo-2-fluorophenyl |
| 7.108 | Me | 4-bromo-3-methylphenyl |
| 7.109 | Me | 6-(2,2-difluoro-1,4-benzo-dioxanyl) |
| 7.110 | Me | 6-(2,2,3-trifluoro-1,4-benzodioxanyl) |
| 7.111 | Me | pentafluorophenyl |
| 7.112 | Me | 3-F,5-CF$_3$-phenyl |
| 7.113 | Me | 3-OMe,5-CF$_3$-phenyl |
| 7.114 | Me | 3-NO$_2$,5-CF$_3$-phenyl |
| 7.115 | Me | 4-Br,3-CF$_3$-phenyl |
| 7.116 | Me | 4-tert-butylphenyl |
| 7.117 | Me | 4-sec-butylphenyl |
| 7.118 | Me | 4-butylphenyl |
| 7.119 | Me | 4-butoxyphenyl |
| 7.120 | Me | 3-F,4-MeO-phenyl |
| 7.121 | Me | 3-Cl,4-MeO-phenyl |
| 7.122 | Me | 3-Cl,4-Me-phenyl |
| 7.123 | Me | 4-Cl,2-Me-phenyl |
| 7.124 | Me | 4-Cl,3-Me-phenyl |
| 7.125 | Me | 5-Cl,2-Me-phenyl |
| 7.126 | Me | 4-Cl,3-NO$_2$-phenyl |
| 7.127 | Me | 5-indanyl |
| 7.128 | Me | 3,5-dinitrophenyl |
| 7.129 | Me | 2-nitrophenyl |
| 7.130 | Me | 3-nitrophenyl |
| 7.131 | Me | 4-nitrophenyl |
| 7.132 | Me | 2-ethylphenyl |
| 7.133 | Me | 3-ethylphenyl |
| 7.134 | Me | 4-ethylphenyl |
| 7.135 | Me | 3-ethoxyphenyl |
| 7.136 | Me | 4-ethoxyphenyl |
| 7.137 | Me | 3-F,4-CH$_3$-phenyl |
| 7.138 | Me | 4-F,3-NO$_2$-phenyl |
| 7.139 | Me | 4-Cl,3-CF$_3$-phenyl |
| 7.140 | Et | 3-hydroxyphenyl |
| 7.141 | Me | 4-hydroxyphenyl |
| 7.142 | Me | 3-hydroxy-4-methoxyphenyl |
| 7.143 | Me | 4-hydroxy-3-methylphenyl |
| 7.144 | Me | 4-hydroxy-3-nitrophenyl |
| 7.145 | Me | 4-isopropylphenyl |
| 7.146 | Me | 3-iodophenyl |
| 7.147 | Me | 4-iodophenyl |
| 7.148 | Me | 3-mercaptophenyl |
| 7.149 | Me | 4-mercaptophenyl |
| 7.150 | Me | 2-NH$_2$C(S)-phenyl |
| 7.151 | Me | 3-NH$_2$C(S)-phenyl |
| 7.152 | Me | 4-NH$_2$C(S)-phenyl |
| 7.153 | Me | 3-methylmercaptophenyl |
| 7.154 | Me | 4-methylmercaptophenyl |
| 7.155 | Me | 2-methylthio-5-CF$_3$-phenyl |
| 7.156 | Me | 4-CH$_3$,3-NO$_2$-phenyl |
| 7.157 | Me | 4-CH$_3$,2-NO$_2$-phenyl |
| 7.158 | Me | 2-CH$_3$,4-NO$_2$-phenyl |
| 7.159 | Me | 2-CH$_3$,5-NO$_2$-phenyl |
| 7.160 | Me | 4-methoxy,3-NO$_2$-phenyl |
| 7.161 | Me | 4-(4-morpholino)phenyl |
| 7.162 | Me | 3-phenoxyphenyl |
| 7.163 | Me | 4-phenoxyphenyl |
| 7.164 | Me | 4-propylphenyl |
| 7.165 | Me | 3-methanesulfinylmethyl-4-MeO-phenyl |
| 7.166 | Me | 4-sulfamoylphenyl |
| 7.167 | Me | 4-MeO,3-CH$_3$SCH$_2$-phenyl |
| 7.168 | Me | 3-trifluoromethylsulfonyl-phenyl |
| 7.169 | Me | 3-rhodanophenyl |
| 7.170 | Me | 4-rhodanophenyl |
| 7.171 | Me | 3-rhodanomethylphenyl |
| 7.172 | Me | 4-rhodanomethylphenyl |
| 7.173 | Me | 3-prop-1-en-3-yloxyphenyl |
| 7.174 | Me | 2-cyclopropylmethoxyphenyl |
| 7.175 | Me | 2,3,4,5-tetrafluorophenyl |
| 7.176 | Me | 2,3,5,6-tetrafluorophenyl |
| 7.177 | Me | 2,3,4-trimethoxyphenyl |
| 7.178 | Me | 3,4,5-trimethoxyphenyl |
| 7.179 | Me | 5,6,7,8-tetrahydro-1-naphthyl |
| 7.180 | Me | 2,3-dihydrobenzofur-5-yl |
| 7.181 | Me | 2,3-dihydrobenzofur-6-yl |
| 7.182 | Me | 7-OMe,2,3-dihydrobenzo-fur-5-yl |
| 7.183 | Me | 3-trimethylsilylphenyl |
| 7.184 | CF$_3$ | 3-trimethylsilylphenyl |
| 7.185 | Me | benzyl |
| 7.186 | Me | 3-CF$_3$-benzyl |
| 7.187 | Me | 4-chlorobenzyl |
| 7.188 | Me | 3-CF$_3$,4-chlorobenzyl |
| 7.189 | Me | phenoxymethyl |
| 7.190 | Me | 3-chlorophenoxymethyl |
| 7.191 | Me | 3-CF$_3$-phenoxymethyl |
| 7.192 | Me | 2-methoxy-5-benzodioxolyl |
| 7.193 | Me | 2-methyl-5-benzodioxolyl |
| 7.194 | Me | 2-phenyl-5-benzodioxolyl |
| 7.195 | Me | 3-methoxycarbonyl-phenyl |
| 7.196 | Me | 4-methoxycarbonyl-phenyl |
| 7.197 | Me | 3-methoximinomethyl-phenyl |
| 7.198 | Me | 3-ethoximinomethyl-phenyl |
| 7.199 | Me | 4-methoximinomethyl-phenyl |
| 7.200 | Me | 2-pyrazinyl |
| 7.201 | Me | 3,5-dimethyl-pyrazin-2-yl |
| 7.202 | Me | 3-ethoxy-pyrazin-2-yl |
| 7.203 | Me | 5-CONHCH$_3$-pyrazin-2-yl |
| 7.204 | Me | 2-pyrimidinyl |
| 7.205 | Me | 4-chloro-pyrimidin-2-yl |
| 7.206 | Me | 4-ethoxy-pyrimidin-2-yl |
| 7.207 | Me | 4-methoxy-pyrimidin-2-yl |
| 7.208 | Me | 4-(2,2,2-trifluoroethoxy)-pyrimidin-2-yl |
| 7.209 | Me | 2-SCH$_3$-pyrimidin-4-yl |
| 7.210 | Me | 4-isopropoxy-pyrimidin-2-yl |
| 7.211 | Me | 4,6-dimethyl-pyrimidin-2-yl |
| 7.212 | Me | 4-Me,6-cyclopropyl-pyrimidin-2-yl |
| 7.213 | Me | 4,6-diethoxy-pyrimidin-2-yl |
| 7.214 | Me | 4-Me,6-OMe-pyrimidin-2-yl |
| 7.215 | Me | 4-Me,6-CF$_3$-pyrimidin-2-yl |
| 7.216 | Me | 2-pyridyl |
| 7.217 | Me | 3-pyridyl |
| 7.218 | ▷ | 4-pyridyl |
| 7.219 | Me | 2,6-dichloro-4-pyridyl |
| 7.220 | Me | 2-chloro-4-pyridyl |
| 7.221 | Me | 2-quinolinyl |
| 7.222 | Me | 6-quinolinyl |
| 7.223 | Me | 7-quinolinyl |
| 7.224 | Me | 5-isoquinolinyl |
| 7.225 | Me | 2-benzimidazolyl |

TABLE 7-continued

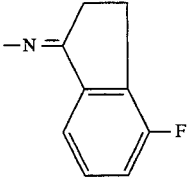 (Ie)

| 7.226 | Me | 3,4-benzocumarin-6-yl |
| 7.227 | Me | 2-thienyl |
| 7.228 | Me | 3-methylbenzo(b)thien-2-yl |
| 7.229 | Me | 5-chlorothien-2-yl |
| 7.230 | Me | 5-bromothien-2-yl |
| 7.231 | Me | 2-methoxycarbonyl-3-thienyl |
| 7.232 | Me | 2-furyl |
| 7.233 | Me | benzo[b]fur-2-yl |
| 7.234 | Me | 1-methylpyrrol-2-yl |
| 7.235 | Me | 4-methylthien-2-yl |
| 7.236 | Me | 5-methylfur-2-yl |
| 7.237 | Me | 6-bromo-2-pyridyl |
| 7.238 | Me | 4-trifluoromethyl-2-pyridyl |
| 7.239 | Me | 4-ethoxy-pyrimidin-2-yl |
| 7.240 | Me | 5-chloro-2-pyridyl |
| 7.241 | Me | 5-bromo-2-pyridyl |
| 7.242 | Me | 6-trifluoromethyl-2-pyridyl |
| 7.243 | Me | 6-quinoxalinyl |
| 7.244 | Me | 2-quinoxalinyl |
| 7.245 | Me | 6-chloro-2-quinoxalinyl |
| 7.246 | Me | 2-thiazolyl |
| 7.247 | Me | 5-trifluoromethyl-2-pyridyl |
| 7.248 | Me | 2,1,3-benzothiadiazol-5-yl |
| 7.249 | Me | 2,1,3-benzoxadiazol-5-yl |
| 7.250 | Me | 4-CN-2-pyridyl |
| 7.251 | Me | 5-bromo-3-pyridyl |
| 7.252 | Me | 6-methyl-3-pyridyl |
| 7.253 | Me | 1-morpholinyl |
| 7.254 | Me | 1-(2,6-dimethylmorpholinyl) |
| 7.255 | Me | 1-(2-methylmorpholinyl) |
| 7.256 | Me | 1-piperidinyl |
| 7.257 | Me | 1-piperazinyl |
| 7.258 | Me | methyl |
| 7.259 | Me | ethyl |
| 7.260 | Me | propyl |
| 7.261 | Me | isopropyl |
| 7.262 | Me | cyclopropyl |
| 7.263 | 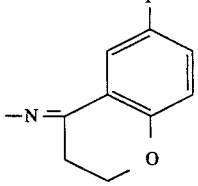 | cyclopropyl |
| 7.264 | CN | isopropyl |
| 7.265 | CN | cyclopropyl |
| 7.266 | CN | phenyl |

| Ex. No. | $N=C(R_1)R_2$ | Phys. data |

7.267 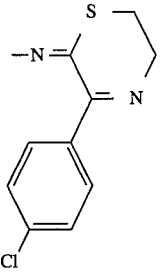

7.268 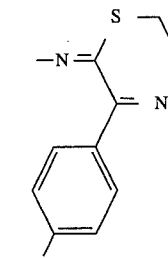

7.269 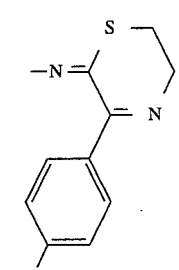

7.270 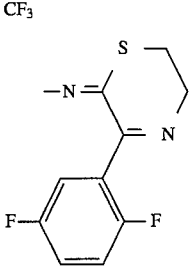

7.271 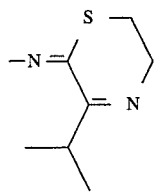

7.272

7.273

TABLE 7-continued

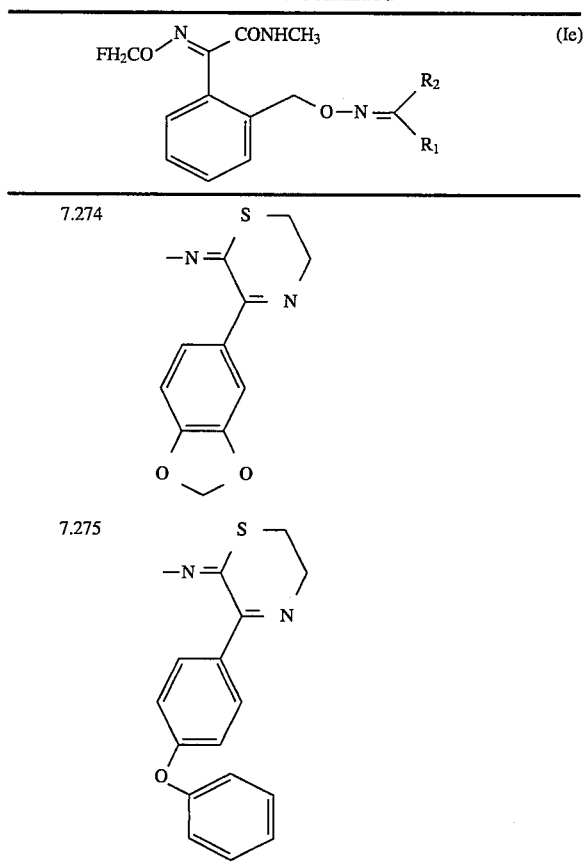

TABLE 7-continued

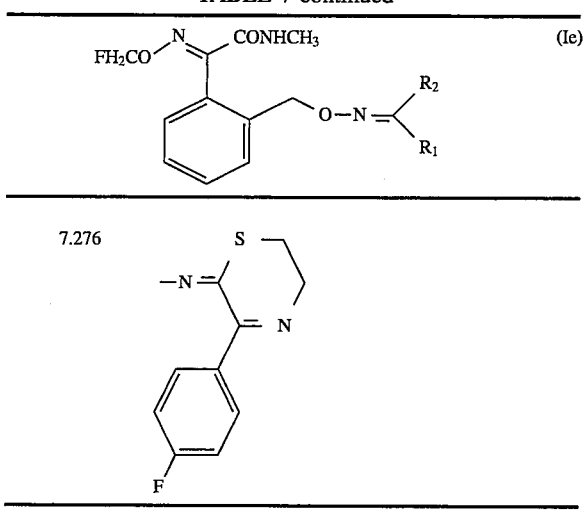

TABLE 8

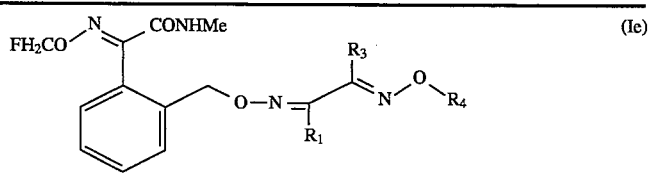

| Ex. No. | $R_1$ | $R_3$ | $R_4$ | Phys. data m.p. or MS: mol. peak (%) base peak |
|---|---|---|---|---|
| 8.1 | Me | Me | Me | |
| 8.2 | Δ | Me | Me | |
| 8.3 | Me | Δ | Me | |
| 8.4 | Me | Me | phenyl | |
| 8.5 | Me | Δ | phenyl | |
| 8.6 | Me | Me | benzyl | |
| 8.7 | Me | Me | Et | |
| 8.8 | Δ | Me | Et | |
| 8.9 | Me | Δ | Et | |
| 8.10 | H | Me | methoxymethyl | |
| 8.11 | Me | Me | methoxymethyl | |
| 8.12 | Me | Δ | methoxymethyl | |
| 8.13 | Δ | Me | methoxymethyl | |
| 8.14 | Me | Me | ethoxymethyl | |
| 8.15 | H | Me | cyanomethyl | |
| 8.16 | Me | Me | cyanomethyl | |
| 8.17 | Δ | Me | cyanomethyl | |
| 8.18 | H | Me | tert-butyl | |
| 8.19 | Me | Me | tert-butyl | |
| 8.20 | Me | Me | propargyl | |
| 8.21 | Δ | Me | propargyl | |
| 8.22 | Me | Δ | propargyl | |

TABLE 8-continued (Ie)

[Structure: FH₂CO-N=C(CONHMe)-phenyl-CH₂-O-N=C(R₁)-C(R₃)=N-O-R₄]

| Ex. No. | R₁ | R₃ | R₄ | Phys. data m.p. or MS: mol. peak (%) base peak |
|---|---|---|---|---|
| 8.23 | Me | Me | 2,2-dichlorocyclopropylmethyl | |
| 8.24 | Δ | Me | 2,2-dichlorocyclopropylmethyl | |
| 8.25 | H | Me | allyl | |
| 8.26 | Me | Me | allyl | |
| 8.27 | Me | Me | CF₃CH₂ | |
| 8.28 | Δ | Me | CF₃CH₂ | |
| 8.29 | Me | Me | CF₃CH₂CH₂ | |
| 8.30 | Me | Me | CF₃CH₂CH₂CH₂ | |
| 8.31 | Δ | Me | CF₃CH₂CH₂CH₂ | |
| 8.32 | Me | Me | 2-chloro-2-propenyl | ¹H-NMR(CDCl₃)δppm: 1.95(s, 3H), 2.0(s, 3H), 2.92(d, 3H), 4.65 (s, 3H), 5.1(s, 2H), 5.36(m, 2H), 5.75(d, 2H), 6.76(m, 1H), 7.2–7.5(m, 4H) |
| 8.33 | Δ | Me | 2-chloro-2-propenyl | |
| 8.34 | Me | Me | propyl | |
| 8.35 | Me | Me | butyl | |
| 8.36 | Me | Me | hexyl | |
| 8.37 | Me | Me | methoxycarbonylmethyl | |
| 8.38 | Me | Me | 3-fluorobenzyl | |
| 8.39 | Me | Me | 4-chlorobenzyl | |
| 8.40 | Me | Me | 2-chlorobenzyl | |
| 8.41 | Me | Me | 2-CF₃-benzyl | |
| 8.42 | Me | Me | 3-CF₃-benzyl | |
| 8.43 | Me | Me | 4-CF₃-benzyl | |
| 8.44 | Me | Me | 3,4-dichlorobenzyl | |
| 8.45 | Me | Me | 2,4,6-trimethylbenzyl | |
| 8.46 | Me | Me | 4-chloro-2-nitrobenzyl | |
| 8.47 | Me | Me | 3-methoxybenzyl | |
| 8.48 | Me | Me | 2-phenethyl | |
| 8.49 | Me | Me | 3-phenylpropyl | |
| 8.50 | Me | Me | 2-(4-nitrophenyl)ethyl | |
| 8.51 | Me | Me | 2-(2-CF₃-phenyl)ethyl | |
| 8.52 | Me | Me | 2-(4-methoxyphenyl)ethyl | |
| 8.53 | Me | Me | 2-chloro-6-fluorobenzyl | |
| 8.54 | Me | Me | 3,4-methylenedioxybenzyl | |
| 8.55 | Me | Me | 2-cyanobenzyl | |
| 8.56 | Me | Me | 2-(4-chlorophenyl)ethyl | |
| 8.57 | Me | Me | cyclopropylmethyl | |
| 8.58 | Me | Me | 2-(1,3-dioxolanyl)methyl | |
| 8.59 | Me | Me | 2,2,3,3-tetrafluorocyclobutylmethyl | |
| 8.60 | Me | Me | α-fluoro-ethoxycarbonylmethyl | |
| 8.61 | Me | 3-CF₃-phenyl | Me | |
| 8.62 | Me | 4-chlorophenyl | Me | |
| 8.63 | Me | 3-chlorophenyl | Me | |
| 8.64 | Me | 2-fluorophenyl | Me | |
| 8.65 | Me | 4-methylphenyl | Me | |
| 8.66 | Me | 4-methoxyphenyl | Me | |
| 8.67 | Me | 4-bromophenyl | Me | |
| 8.68 | Me | 2-thienyl | Me | |
| 8.69 | Me | 4-fluorophenyl | Me | |
| 8.70 | Me | 3-fluoro-5-CF₃-phenyl | Me | |
| 8.71 | Me | phenyl | Me | |
| 8.72 | Me | 2-methyl- | Me | |

TABLE 8-continued

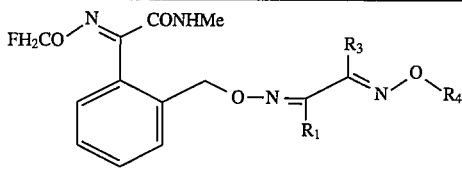

(Ie)

| Ex. No. | $R_1$ | $R_3$ | $R_4$ | Phys. data m.p. or MS: mol. peak (%) base peak |
|---|---|---|---|---|
| 8.73 | Me | 3-bromo-phenyl | Me | |
| 8.74 | Me | 3,4-methylene-dioxyphenyl | Me | |
| 8.75 | Me | 4-methyl-phenyl | Et | |
| 8.76 | Me | Δ | $CH_2CH_2F$ | |
| 8.77 | Δ | Me | $CH_2CH_2F$ | |
| 8.78 | Me | Me | $CH_2CH_2F$ | |
| 8.79 | Me | 4-allyloxy-phenyl | Me | |
| 8.80 | SMe | 4-methyl-phenyl | Me | |
| 8.81 | Et | 4-methyl-phenyl | Me | |
| 8.82 | Me | 4-isobutyl-phenyl | Me | |
| 8.83 | Me | 4-propargyl-oxyphenyl | Me | |
| 8.84 | Me | 4-(2,2,2-tri-fluoroethoxy)-phenyl | Me | |
| 8.85 | Me | 4-ethoxy-phenyl | Me | |
| 8.86 | CN | 4-methyl-phenyl | Me | |
| 8.87 | CN | 4-chloro-phenyl | Me | |
| 8.88 | CN | 3,4-dichloro-phenyl | Me | |
| 8.89 | CN | 4-trifluoro-methoxyphenyl | Me | |
| 8.90 | Me | 3-EtO-phenyl | Me | |
| 8.91 | Me | 3-propoxy-phenyl | Me | |
| 8.92 | Me | 4-propoxy-phenyl | Me | |
| 8.93 | Me | 3-MeS-phenyl | Me | |
| 8.94 | Me | 4-MeS-phenyl | Me | |
| 8.95 | Me | 3-propyl-S-phenyl | Me | |
| 8.96 | Me | 4-propyl-S-phenyl | Me | |
| 8.97 | Me | 4-(3-F-phen-oxy)-phenyl | Me | |
| 8.98 | Me | 4-(4-F-phen-oxy)-phenyl | Me | |
| 8.99 | Me | 3-EtS-phenyl | Me | |
| 8.100 | Me | 4-EtS-phenyl | Me | |
| 8.101 | Me | 4-EtO-phenyl | Me | |
| 8.102 | CN | 3-trifluoro-methylphenyl | Me | |
| 8.103 | CN | 2-chloro-phenyl | Me | |
| 8.104 | CN | 4-fluoro-phenyl | Me | |
| 8.105 | Me | Me | $CH_2F$ | |

TABLE 9

Unless indicated otherwise, this Table describes under each number a compound of type Id and a compound of type If.

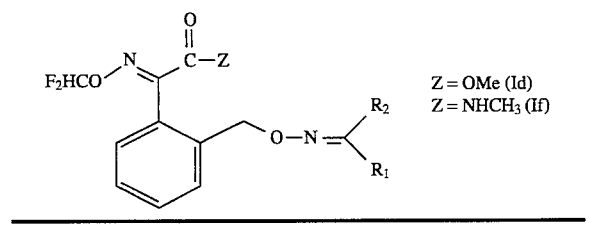

Z = OMe (Id)
Z = NHCH₃ (If)

| Ex. No. | R₁ | R₂ | Phys. data MS: mol. peak (%) base peak |
|---|---|---|---|
| 9.1 | Me | phenyl | |
| 9.2 | Me | 2-fluorophenyl | |
| 9.3 | Me | 3-fluorophenyl | |
| 9.4 | Me | 4-fluorophenyl | |
| 9.5 | cyclopropyl | 4-fluorophenyl | |
| 9.6 | Me | 3-chlorophenyl | |
| 9.7 | cyclopropyl | 3-chlorophenyl | |
| 9.8 | Me | 4-chlorophenyl | |
| 9.9 | Me | 2-bromophenyl | |
| 9.10 | Me | 3-bromophenyl | |
| 9.11 | Me | 4-bromophenyl | |
| 9.12 | cyclopropyl | 4-bromophenyl | |
| 9.13 | cyclopropyl | 4-chlorophenyl | |
| 9.14 | CH₃S | 4-chlorophenyl | |
| 9.15 | CH₃O | 4-chlorophenyl | |
| 9.16 | CH₃OCH₂ | 4-chlorophenyl | |
| 9.17 | CH₃SCH₂ | 4-chlorophenyl | |
| 9.18 | CF₃ | 4-chlorophenyl | |
| 9.19 | CN | 4-chlorophenyl | |
| 9.20 | Et | 4-chlorophenyl | |
| 9.21 | propyl | 4-chlorophenyl | |
| 9.22 | isopropyl | 4-chlorophenyl | |
| 9.23 | Me | 2,4-difluorophenyl | |
| 9.24 | Me | 3,4-difluorophenyl | |
| 9.25 | Me | 2,3-difluorophenyl | |
| 9.26 | Me | 2,5-difluorophenyl | |
| 9.27 | Me | 3,5-difluorophenyl | |
| 9.28 | Me | 2,4-dichlorophenyl | |
| 9.29 | Me | 3,4-dichlorophenyl | |
| 9.30 | Me | 2,5-dichlorophenyl | |
| 9.31 | Me | 3,5-dichlorophenyl | |
| 9.32 | Me | 3-Cl,4-F-phenyl | |
| 9.33 | Me | 4-Cl,2-F-phenyl | |
| 9.34 | Me | 2,3,4-trifluorophenyl | |
| 9.35 | Me | 2,3,6-trifluorophenyl | |
| 9.36 | Me | 2,4,6-trifluorophenyl | |
| 9.37 | Me | 2,4,5-trifluorophenyl | |
| 9.38 | Me | 2,3,4-trichlorophenyl | |
| 9.39 | Me | 3,4,5-trichlorophenyl | |
| 9.40 | Me | 2,4,5-trichlorophenyl | |
| 9.41 | Me | 1-naphthyl | |
| 9.42 | Me | 2-naphthyl | |
| 9.43 | cyclopropyl | 2-naphthyl | |
| 9.44 | Me | 2-methylphenyl | |
| 9.45 | Me | 3-methylphenyl | |
| 9.46 | Me | 4-methylphenyl | |
| 9.47 | cyclopropyl | 4-methylphenyl | |
| 9.48 | Me | 2,3-dimethylphenyl | |
| 9.49 | Me | 2,4-dimethylphenyl | |
| 9.50 | Me | 2,4-dimethylphenyl | |
| 9.51 | Me | 3,4-dimethylphenyl | |
| 9.52 | Me | 3,5-dimethylphenyl | |
| 9.53 | Me | 2-methoxyphenyl | |
| 9.54 | Me | 3-methoxyphenyl | |
| 9.55 | Me | 4-methoxyphenyl | |
| 9.56 | Me | 3,4-dimethoxyphenyl | |
| 9.57 | Me | 3,5-dimethoxyphenyl | |
| 9.58 | Me | 3,4-methylenedioxyphenyl | Z = OMe; NMR(Ex. P-18) |
| 9.59 | Me | 3,4-methylenedioxyphenyl | Z = NHMe; NMR(Ex. P-19) |
| 9.60 | cyclopropyl | 3,4-methylenedioxyphenyl | |
| 9.61 | SMe | 3,4-methylenedioxyphenyl | |
| 9.62 | OMe | 3,4-methylenedioxyphenyl | |
| 9.63 | Me | 3,4-ethylenedioxyphenyl | |
| 9.64 | cyclopropyl | 3,4-ethylenedioxyphenyl | |
| 9.65 | Me | 2,2-difluoro-5-benzodioxolyl | |
| 9.66 | Et | 2,2-difluoro-5-benzodioxolyl | |
| 9.67 | Me | 3-difluoromethoxyphenyl | |
| 9.68 | Me | 4-difluoromethoxyphenyl | |
| 9.69 | Me | 3-(2,2,2-trifluoroethoxy)-phenyl | |
| 9.70 | Me | 3-(1,1,2,2-tetrafluoroethoxy)-phenyl | |
| 9.71 | Me | 3-(1,1,2,3,3,3-hexafluoropropoxy)phenyl | |
| 9.72 | Me | 4-(2,2,2-trifluoroethoxy)-phenyl | |
| 9.73 | Me | 4-(1,1,2,2-tetrafluoroethoxy)-phenyl | |
| 9.74 | Me | 3-trifluoromethoxyphenyl | |
| 9.75 | Me | 4-trifluoromethoxyphenyl | |
| 9.76 | Me | 2-trifluoromethylphenyl | |
| 9.77 | Me | 3-trifluoromethylphenyl | 444(2.5)/116 Z = OMe |
| 9.78 | Me | 3-trifluoromethylphenyl | NMR(Ex. P-16) Z = NHMe |
| 9.79 | cyclopropyl | 3-trifluoromethylphenyl | |
| 9.80 | Et | 3-trifluoromethylphenyl | |
| 9.81 | CN | 3-trifluoromethylphenyl | |
| 9.82 | OMe | 3-trifluoromethylphenyl | |
| 9.83 | SMe | 3-trifluoromethylphenyl | |
| 9.84 | CH₂OCH₃ | 3-trifluoromethylphenyl | |
| 9.85 | Me | 3,5-bis(trifluoromethyl)-phenyl | |
| 9.86 | Me | 4-F,3-CF₃-phenyl | |

TABLE 9-continued

Unless indicated otherwise, this Table describes under each number a compound of type Id and a compound of type If.

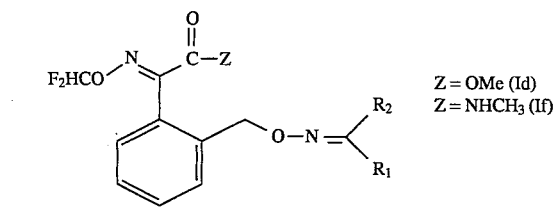

Z = OMe (Id)
Z = NHCH₃ (If)

| | | |
|---|---|---|
| 9.87 | cyclopropyl | 4-F,3-CF₃-phenyl |
| 9.88 | Me | 2-Cl,5-CF₃-phenyl |
| 9.89 | Me | 3,5-dichloro-2-fluoro-4-methoxy-phenyl |
| 9.90 | Me | 3,5-dichloro-2,4-dimethoxy-phenyl |
| 9.91 | Me | 3-acetylphenyl |
| 9.92 | Me | 4-acetylphenyl |
| 9.93 | Me | 3-carboxyphenyl |
| 9.94 | Me | 4-carboxyphenyl |
| 9.95 | Me | 3-carbethoxyphenyl |
| 9.96 | Me | 4-carbethoxyphenyl |
| 9.97 | Me | 2-cyanophenyl |
| 9.98 | Me | 3-cyanophenyl |
| 9.99 | Me | 4-cyanophenyl |
| 9.100 | Me | 3-cyanomethylphenyl |
| 9.101 | Me | 3-cyanomethoxyphenyl |
| 9.102 | Me | 4-cyanomethylphenyl |
| 9.103 | Me | 4-cyclohexylphenyl |
| 9.104 | Me | 4-biphenylyl |
| 9.105 | Me | 2-fluorenyl |
| 9.106 | Me | 3-benzyloxyphenyl |
| 9.107 | Me | 4-benzyloxyphenyl |
| 9.108 | Me | 3,5-dibenzyloxyphenyl |
| 9.109 | Me | 4-bromo-2-fluorophenyl |
| 9.110 | Me | 4-bromo-3-methylphenyl |
| 9.111 | Me | 6-(2,2-difluoro-1,4-benzodioxanyl) |
| 9.112 | Me | 6-(2,2,3-trifluoro-1,4-benzodioxanyl) |
| 9.113 | Me | pentafluorophenyl |
| 9.114 | Me | 3-F,5-CF₃-phenyl |
| 9.115 | Me | 3-OMe,5-CF₃-phenyl |
| 9.116 | Me | 3-NO₂,5-CF₃-phenyl |
| 9.117 | Me | 4-Br,3-CF₃-phenyl |
| 9.118 | Me | 4-tert-butylphenyl |
| 9.119 | Me | 4-sec-butylphenyl |
| 9.120 | Me | 4-butylphenyl |
| 9.121 | Me | 4-butoxyphenyl |
| 9.122 | Me | 3-F,4-MeO-phenyl |
| 9.123 | Me | 3-Cl,4-MeO-phenyl |
| 9.124 | Me | 3-Cl,4-Me-phenyl |
| 9.125 | Me | 4-Cl,2-Me-phenyl |
| 9.126 | Me | 4-Cl,3-Me-phenyl |
| 9.127 | Me | 5-Cl,2-Me-phenyl |
| 9.128 | Me | 4-Cl,3-NO₂-phenyl |
| 9.129 | Me | 5-indanyl |
| 9.130 | Me | 3,5-dinitrophenyl |
| 9.131 | Me | 2-nitrophenyl |
| 9.132 | Me | 3-nitrophenyl |
| 9.133 | Me | 4-nitrophenyl |
| 9.134 | Me | 2-ethylphenyl |
| 9.135 | Me | 3-ethylphenyl |
| 9.136 | Me | 4-ethylphenyl |
| 9.137 | Me | 3-ethoxyphenyl |
| 9.138 | Me | 4-ethoxyphenyl |
| 9.139 | Me | 3-F,4-CH₃-phenyl |
| 9.140 | Me | 4-F,3-NO₂-phenyl |
| 9.141 | Me | 4-Cl,3-CF₃-phenyl |
| 9.142 | Et | 3-hydroxyphenyl |
| 9.143 | Me | 4-hydroxyphenyl |
| 9.144 | Me | 3-hydroxy-4-methoxyphenyl |
| 9.145 | Me | 4-hydroxy-3-methylphenyl |
| 9.146 | Me | 4-hydroxy-3-nitrophenyl |
| 9.147 | Me | 4-isopropylphenyl |
| 9.148 | Me | 3-iodophenyl |
| 9.149 | Me | 4-iodophenyl |
| 9.150 | Me | 3-mercaptophenyl |
| 9.151 | Me | 4-mercaptophenyl |
| 9.152 | Me | 2-NH₂C(S)-phenyl |
| 9.153 | Me | 3-NH₂C(S)-phenyl |
| 9.154 | Me | 4-NH₂C(S)-phenyl |
| 9.155 | Me | 3-methylmercaptophenyl |
| 9.156 | Me | 4-methylmercaptophenyl |
| 9.157 | Me | 2-methylthio-5-CF₃-phenyl |
| 9.158 | Me | 4-CH₃,3-NO₂-phenyl |
| 9.159 | Me | 4-CH₃,2-NO₂-phenyl |
| 9.160 | Me | 2-CH₃,4-NO₂-phenyl |
| 9.161 | Me | 2-CH₃,5-NO₂-phenyl |
| 9.162 | Me | 4-methoxy,3-NO₂-phenyl |
| 9.163 | Me | 4-(4-morpholino)phenyl |
| 9.164 | Me | 3-phenoxyphenyl |
| 9.165 | Me | 4-phenoxyphenyl |
| 9.166 | Me | 4-propylphenyl |
| 9.167 | Me | 3-methanesulfinylmethyl-4-MeO-phenyl |
| 9.168 | Me | 4-sulfamoylphenyl |
| 9.169 | Me | 4-MeO,3-CH₃SCH₂-phenyl |
| 9.170 | Me | 3-trifluoromethylsulfonyl-phenyl |
| 9.171 | Me | 3-rhodanophenyl |
| 9.172 | Me | 4-rhodanophenyl |
| 9.173 | Me | 3-rhodanomethylphenyl |
| 9.174 | Me | 4-rhodanomethylphenyl |
| 9.175 | Me | 3-prop-1-en-3-yloxyphenyl |
| 9.176 | Me | 2-cyclopropylmethoxyphenyl |
| 9.177 | Me | 2,3,4,5-tetrafluorophenyl |
| 9.178 | Me | 2,3,5,6-tetrafluorophenyl |
| 9.179 | Me | 2,3,4-trimethoxyphenyl |
| 9.180 | Me | 3,4,5-trimethoxyphenyl |
| 9.181 | Me | 5,6,7,8-tetrahydro-1-naphthyl |
| 9.182 | Me | 2,3-dihydrobenzofur-5-yl |
| 9.183 | Me | 2,3-dihydrobenzofur-6-yl |
| 9.184 | Me | 7-OMe,2,3-dihydrobenzofur-5-yl |
| 9.185 | Me | 3-trimethylsilylphenyl |
| 9.186 | CF₃ | 3-trimethylsilylphenyl |
| 9.187 | Me | benzyl |
| 9.188 | Me | 3-CF₃-benzyl |
| 9.189 | Me | 4-chlorobenzyl |
| 9.190 | Me | 3-CF₃,4-chlorobenzyl |
| 9.191 | Me | phenoxymethyl |
| 9.192 | Me | 3-chlorophenoxymethyl |
| 9.193 | Me | 3-CF₃-phenoxymethyl |
| 9.194 | Me | 2-methoxy-5-benzodioxolyl |
| 9.195 | Me | 2-methyl-5-benzodioxolyl |
| 9.196 | Me | 2-phenyl-5-benzodioxolyl |
| 9.197 | Me | 3-methoxycarbonyl-phenyl |
| 9.198 | Me | 4-methoxycarbonyl-phenyl |
| 9.199 | Me | 3-methoximinomethyl-phenyl |
| 9.200 | Me | 3-ethoximinomethyl-phenyl |
| 9.201 | Me | 4-methoximinomethyl-phenyl |
| 9.202 | Me | 2-pyrazinyl |
| 9.203 | Me | 3,5-dimethyl-pyrazin-2-yl |
| 9.204 | Me | 3-ethoxy-pyrazin-2-yl |
| 9.205 | Me | 5-CONHCH₃-pyrazin-2-yl |

TABLE 9-continued

Unless indicated otherwise, this Table describes under each number a compound of type Id and a compound of type If.

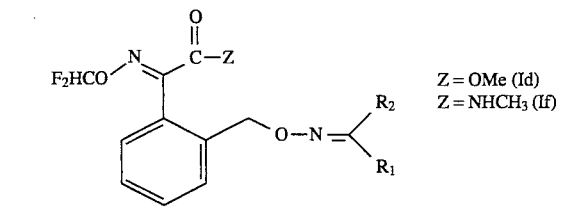

Z = OMe (Id)
Z = NHCH₃ (If)

| | | |
|---|---|---|
| 9.206 | Me | 2-pyrimidinyl |
| 9.207 | Me | 4-chloro-pyrimidin-2-yl |
| 9.208 | Me | 4-ethoxy-pyrimidin-2-yl |
| 9.209 | Me | 4-methoxy-pyrimidin-2-yl |
| 9.210 | Me | 4-(2,2,2-trifluoroethoxy)-pyrimidin-2-yl |
| 9.211 | Me | 2-SCH₃-pyrimidin-4-yl |
| 9.212 | Me | 4-isopropoxy-pyrimidin-2-yl |
| 9.213 | Me | 4,6-dimethyl-pyrimidin-2-yl |
| 9.214 | Me | 4-Me,6-cyclopropyl-pyrimidin-2-yl |
| 9.215 | Me | 4,6-diethoxy-pyrimidin-2-yl |
| 9.216 | Me | 4-Me,6-OMe-pyrimidin-2-yl |
| 9.217 | Me | 4-Me,6-CF₃-pyrimidin-2-yl |
| 9.218 | Me | 2-pyridyl |
| 9.219 | Me | 3-pyridyl |
| 9.220 | cyclopropyl | 4-pyridyl |
| 9.221 | Me | 2,6-dichloro-4-pyridyl |
| 9.222 | Me | 2-chloro-4-pyridyl |
| 9.223 | Me | 2-quinolinyl |
| 9.224 | Me | 6-quinolinyl |
| 9.225 | Me | 7-quinolinyl |
| 9.226 | Me | 5-isoquinolinyl |
| 9.227 | Me | 2-benzimidazolyl |
| 9.228 | Me | 3,4-benzocumarin-6-yl |
| 9.229 | Me | 2-thienyl |
| 9.230 | Me | 3-methylbenzo(b)thien-2-yl |
| 9.231 | Me | 5-chlorothien-2-yl |
| 9.232 | Me | 5-bromothien-2-yl |
| 9.233 | Me | 2-methoxycarbonyl-3-thienyl |
| 9.234 | Me | 2-furyl |
| 9.235 | Me | benzo[b]fur-2-yl |
| 9.236 | Me | 1-methylpyrrol-2-yl |
| 9.237 | Me | 4-methylthien-2-yl |
| 9.238 | Me | 5-methylfur-2-yl |
| 9.239 | Me | 6-bromo-2-pyridyl |
| 9.240 | Me | 4-trifluoromethyl-2-pyridyl |
| 9.241 | Me | 4-ethoxy-pyrimidin-2-yl |
| 9.242 | Me | 5-chloro-2-pyridyl |
| 9.243 | Me | 5-bromo-2-pyridyl |
| 9.244 | Me | 6-trifluoromethyl-2-pyridyl |
| 9.245 | Me | 6-quinoxalinyl |
| 9.246 | Me | 2-quinoxalinyl |
| 9.247 | Me | 6-chloro-2-quinoxalinyl |
| 9.248 | Me | 2-thiazolyl |
| 9.249 | Me | 5-trifluoromethyl-2-pyridyl |
| 9.250 | Me | 2,1,3-benzothiadiazol-5-yl |
| 9.251 | Me | 2,1,3-benzoxadiazol-5-yl |
| 9.252 | Me | 4-CN-2-pyridyl |
| 9.253 | Me | 5-bromo-3-pyridyl |
| 9.254 | Me | 6-methyl-3-pyridyl |
| 9.255 | Me | 1-morpholinyl |
| 9.256 | Me | 1-(2,6-dimethylmorpholinyl) |
| 9.257 | Me | 1-(2-methylmorpholinyl) |
| 9.258 | Me | 1-piperidinyl |
| 9.259 | Me | 1-piperazinyl |
| 9.260 | Me | methyl |
| 9.261 | Me | ethyl |
| 9.262 | Me | propyl |
| 9.263 | Me | isopropyl |
| 9.264 | Me | cyclopropyl |

TABLE 9-continued

Unless indicated otherwise, this Table describes under each number a compound of type Id and a compound of type If.

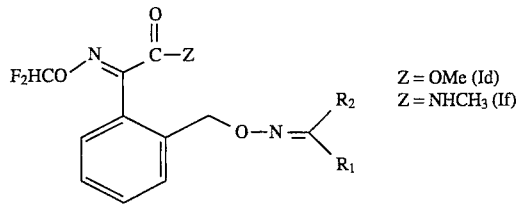

Z = OMe (Id)
Z = NHCH₃ (If)

| | | |
|---|---|---|
| 9.265 | cyclopropyl | cyclopropyl |
| 9.266 | CN | isopropyl |
| 9.267 | CN | cyclopropyl |
| 9.268 | CN | phenyl |

| Ex. No. | N=C(R₁)R₂ | Phys. data |
|---|---|---|
| 9.269 | 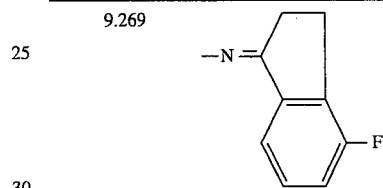 | |
| 9.270 | 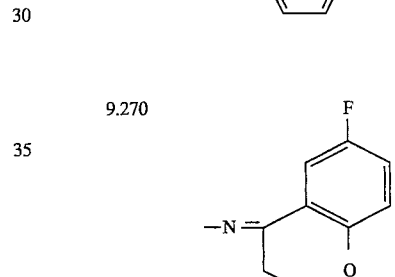 | |
| 9.271 | 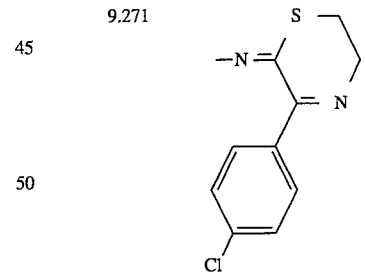 | |
| 9.272 | 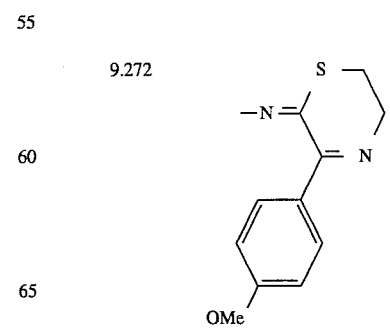 | |

TABLE 9-continued
Unless indicated otherwise, this Table describes under each number a compound of type Id and a compound of type If.
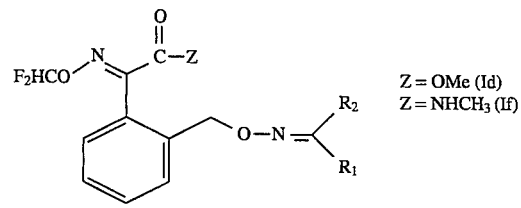
Z = OMe (Id)
Z = NHCH$_3$ (If)
9.273 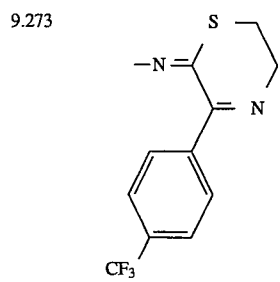
9.274 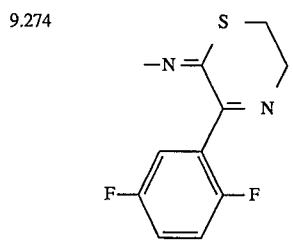
9.275 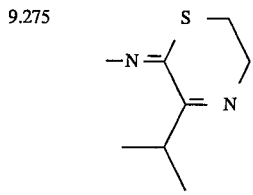
9.276 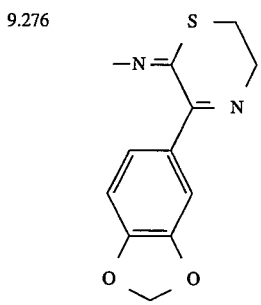
TABLE 9-continued
Unless indicated otherwise, this Table describes under each number a compound of type Id and a compound of type If.
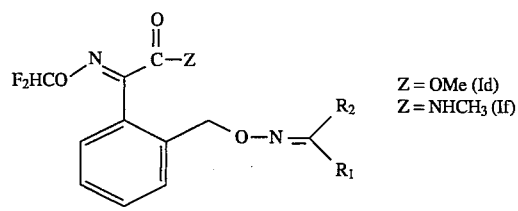
Z = OMe (Id)
Z = NHCH$_3$ (If)
9.277 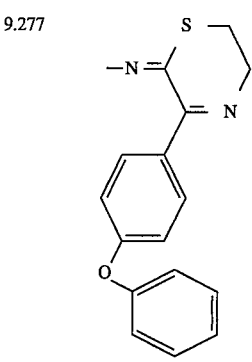
9.278 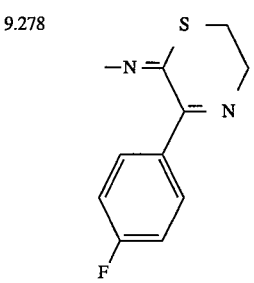

TABLE 10

Unless indicated otherwise, this Table describes under each number a compound of type Id and a compound of type If.

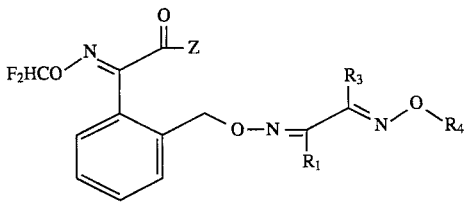

Z = OMe (Id)
Z = NHMe (If)

| Ex. No. | $R_1$ | $R_3$ | $R_4$ | Phys. data m.p. or MS: mol. peak (%) base peak |
|---|---|---|---|---|
| 10.1 | Me | Me | Me | |
| 10.2 | Δ | Me | Me | |
| 10.3 | Me | Δ | Me | |
| 10.4 | Me | Me | phenyl | |
| 10.5 | Me | Δ | phenyl | |
| 10.6 | Me | Me | benzyl | |
| 10.7 | Me | Me | Et | |
| 10.8 | Δ | Me | Et | |
| 10.9 | Me | Δ | Et | |
| 10.10 | H | Me | methoxymethyl | |
| 10.11 | Me | Me | methoxymethyl | |
| 10.12 | Me | Δ | methoxymethyl | |
| 10.13 | Δ | Me | methoxymethyl | |
| 10.14 | Me | Me | ethoxymethyl | |
| 10.15 | H | Me | cyanomethyl | |
| 10.16 | Me | Me | cyanomethyl | |
| 10.17 | Δ | Me | cyanomethyl | |
| 10.18 | H | Me | tert-butyl | |
| 10.19 | Me | Me | tert-butyl | |
| 10.20 | Me | Me | propargyl | |
| 10.21 | Δ | Me | propargyl | |
| 10.22 | Me | Δ | propargyl | |
| 10.23 | Me | Me | 2,2-dichlorocyclopropylmethyl | |
| 10.24 | Δ | Me | 2,2-dichlorocyclopropylmethyl | |
| 10.25 | H | Me | allyl | |
| 10.26 | Me | Me | allyl | |
| 10.27 | Me | Me | $CF_3CH_2$ | |
| 10.28 | Δ | Me | $CF_3CH_2$ | |
| 10.29 | Me | Me | $CF_3CH_2CH_2$ | |
| 10.30 | Me | Me | $CF_3CH_2CH_2CH_2$ | |
| 10.31 | Δ | Me | $CF_3CH_2CH_2CH_2$ | |
| 10.32 | Me | Me | 2-chloro-2-propenyl | |
| 10.33 | Δ | Me | 2-chloro-2-propenyl | |
| 10.34 | Me | Me | propyl | |
| 10.35 | Me | Me | butyl | |
| 10.36 | Me | Me | hexyl | |
| 10.37 | Me | Me | methoxycarbonylmethyl | |
| 10.38 | Me | Me | 3-fluorobenzyl | |
| 10.39 | Me | Me | 4-chlorobenzyl | |
| 10.40 | Me | Me | 2-chlorobenzyl | |
| 10.41 | Me | Me | 2-$CF_3$-benzyl | |
| 10.42 | Me | Me | 3-$CF_3$-benzyl | |
| 10.43 | Me | Me | 4-$CF_3$-benzyl | |
| 10.44 | Me | Me | 3,4-dichlorobenzyl | |
| 10.45 | Me | Me | 2,4,6-trimethylbenzyl | |
| 10.46 | Me | Me | 4-chloro-2-nitrobenzyl | |
| 10.47 | Me | Me | 3-methoxybenzyl | |
| 10.48 | Me | Me | 2-phenethyl | |
| 10.49 | Me | Me | 3-phenylpropyl | |
| 10.50 | Me | Me | 2-(4-nitrophenyl)ethyl | |
| 10.51 | Me | Me | 2-(2-$CF_3$-phenyl)ethyl | |
| 10.52 | Me | Me | 2-(4-methoxyphenyl)ethyl | |
| 10.53 | Me | Me | 2-chloro-6-fluorobenzyl | |
| 10.54 | Me | Me | 3,4-methylenedioxybenzyl | |

TABLE 10-continued

Unless indicated otherwise, this Table describes under each number a compound of type Id and a compound of type If.

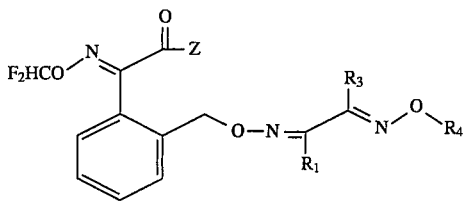

Z = OMe (Id)
Z = NHMe (If)

| Ex. No. | R₁ | R₃ | R₄ | Phys. data m.p. or MS: mol. peak (%) base peak |
|---|---|---|---|---|
| 10.55 | Me | Me | 2-cyanobenzyl | |
| 10.56 | Me | Me | 2-(4-chlorophenyl)ethyl | |
| 10.57 | Me | Me | cyclopropylmethyl | |
| 10.58 | Me | Me | 2-(1,3-dioxolanyl)methyl | |
| 10.59 | Me | Me | 2,2,3,3-tetrafluorocyclo-butylmethyl | |
| 10.60 | Me | Me | α-fluoro-ethoxycarbonylmethyl | |
| 10.61 | Me | 3-CF₃-pehnyl | Me | |
| 10.62 | Me | 4-chloro-phenyl | Me | |
| 10.63 | Me | 3-chloro-phenyl | Me | |
| 10.64 | Me | 2-fluoro-phenyl | Me | |
| 10.65 | Me | 4-methyl-phenyl | Me | |
| 10.66 | Me | 4-methoxy-phenyl | Me | |
| 10.67 | Me | 4-bromo-phenyl | Me | |
| 10.68 | Me | 2-thienyl | Me | |
| 10.69 | Me | 4-fluoro-phenyl | Me | |
| 10.70 | Me | 3-fluoro-5-CF₃-phenyl | Me | |
| 10.71 | Me | phenyl | Me | |
| 10.72 | Me | 2-methyl-phenyl | Me | |
| 10.73 | Me | 3-bromo-phenyl | Me | |
| 10.74 | Me | 3,4-methylene-dioxyphenyl | Me | |
| 10.75 | Me | 4-methyl-phenyl | Et | |
| 10.76 | Me | Δ | CH₂CH₂F | |
| 10.77 | Δ | Me | CH₂CH₂F | |
| 10.78 | Me | Me | CH₂CH₂F | |
| 10.79 | Me | 4-allyloxy-phenyl | Me | |
| 10.80 | SMe | 4-methyl-phenyl | Me | |
| 10.81 | Et | 4-methyl-phenyl | Me | |
| 10.82 | Me | 4-isobutyl-phenyl | Me | |
| 10.83 | Me | 4-propargyl-oxyphenyl | Me | |
| 10.84 | Me | 4-(2,2,2-tri-fluoroethoxy)-phenyl | Me | |
| 10.85 | Me | 4-ethoxy-phenyl | Me | |
| 10.86 | CN | 4-methyl-phenyl | Me | |
| 10.87 | CN | 4-chloro-phenyl | Me | |

TABLE 10-continued

Unless indicated otherwise, this Table describes under each number a compound of type Id and a compound of type If.

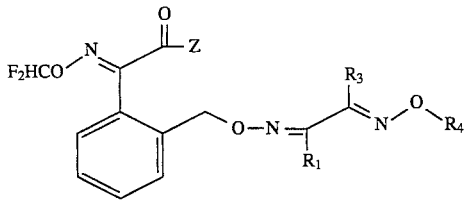

Z = OMe (Id)
Z = NHMe (If)

| Ex. No. | $R_1$ | $R_3$ | $R_4$ | Phys. data m.p. or MS: mol. peak (%) base peak |
|---|---|---|---|---|
| 10.88 | CN | 3,4-dichlorophenyl | Me | |
| 10.89 | CN | 4-trifluoromethoxyphenyl | Me | |
| 10.90 | CN | 3-trifluoromethylphenyl | Me | |
| 10.91 | CN | 2-chlorophenyl | Me | |
| 10.92 | CN | 4-fluorophenyl | Me | |

2. Formulation Examples for Compounds of Formula I (Throughout, Percentages are by Weight)

| 2.1. Wettable powders | a) | b) | c) |
|---|---|---|---|
| a compound of Tables 1–10 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.2. Emulsifiable concentrate | |
|---|---|
| a compound of Tables 1–10 | 10% |
| octylphenol polyethylene glycol ether (4–5 mol of ethylene oxide) | 3% |
| calcium dodecylbenzenesulfonate | 3% |
| cyclohexanone | 34% |
| xylene mixture | 50% |

Emulsions of any required concentration can be obtained from this concentrate by dilution with water.

| 2.3. Dusts | a) | b) |
|---|---|---|
| a compound of Tables 1–10 | 5% | 8% |
| talcum | 95% | — |
| kaolin | — | 92% |

Ready-for-use dusts are obtained by mixing the active ingredient with the carrier and grinding the mixture in a suitable mill.

| 2.4. Extruder granules | |
|---|---|
| a compound of Tables 1–10 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granules | |
|---|---|
| a compound of Tables 1–10 | 3% |
| polyethylene glycol (mol. wt. 200) | 3% |
| kaolin | 94% |

(mol. wt. = molecular weight)

The finely ground active ingredient is uniformly applied, in a mixer, to the kaolin moistened with polyethylene glycol. Non-dusty coated granules are obtained in this manner.

| 2.6. Suspension concentrate | |
|---|---|
| a compound of Tables 1–10 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |

| 2.6. Suspension concentrate | |
| --- | --- |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

In the following Examples B-1 to B-15, compounds according to the invention exhibit a pronounced activity against fungus infestation.

EXAMPLE B-1

Action against *Phytophthora infestans* on Tomato Plants a) Curative Action

After a cultivation period of 3 weeks, tomato plants of the "Red Gnome" variety are sprayed with a zoospore suspension of the fungus and incubated in a cabinet at 18° to 20° and 100% relative humidity. Humidification is stopped after 24 hours. When the plants have dried, they are sprayed with a mixture comprising the test compound formulated as a wettable powder in a concentration of 200 ppm. After the spray coating has dried, the plants are again placed in the humidity cabinet for 4 days. The activity of the test compounds is evaluated on the basis of the number and size of the typical leaf specks that have occurred after that time.

b) Preventive-systemic Action

The test compound formulated as a wettable powder is applied in a concentration of 60 ppm (based on the volume of the soil) to the soil surface of three-week-old tomato plants of the "Red Gnome" variety planted in pots. After a 3-day waiting period, the undersides of the leaves of the plants are sprayed with a zoospore suspension of *Phytophthora infestans*. The plants are then kept in a spray cabinet for 5 days at 18° to 20° C. and 100% relative humidity. After that time, typical leaf specks form, the number and size of which are used to evaluate the activity of the test compounds.

While infestation is 100% on untreated and infected control plants, the compounds of formula I according to one of Tables 1 to 10, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, limit infestation to 20% or less in both tests.

EXAMPLE B-2

Action against *Plasmopara viticola* (Bert. et Curt.) (Berl. et DeToni) on Vines a) Residual-preventive Action Vine seedlings of the "Chasselas" variety are grown in a greenhouse. 3 plants are sprayed in the 10-leaf stage with a mixture (200 ppm active ingredient). After the spray coating has dried, the undersides of the leaves of the plants are infected uniformly with a spore suspension of the fungus. The plants are then kept in a humidity chamber for 8 days. After that time, the control plants exhibit marked symptoms of disease. The activity of the test compounds is evaluated on the basis of the number and size of the sites of infection on the treated plants.

b) Curative Action

Vine seedlings of the "Chasselas" variety are grown in a greenhouse and the undersides of the leaves are infected in the 10-leaf stage with a spore suspension of *Plasmopara viticola*. After 24 hours in a humidity cabinet, the plants are sprayed with a spray mixture of the test compound (200 ppm active ingredient). Then the plants are kept in the humidity cabinet for a further 7 days. After that time the control plants exhibit symptoms of disease. The activity of the test compounds is evaluated on the basis of the number and size of the sites of infection on the treated plants.

In comparison with the control plants, infestation is 20% or less on the plants treated with compounds of formula I, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58.

EXAMPLE B-3

Action against *Pythium debaryanum* on Sugar Beet (*Beta vulgaris*)

a) Action following Soil Application

The fungus is cultivated on sterile oat grains and added to an earth/sand mixture. The earth so infected is introduced into plant pots and sown with sugar beet seeds. Immediately after sowing, the test compounds, formulated as wettable powders, in the form of an aqueous suspension are poured over the soil (20 ppm active ingredient, based on the volume of the soil). The pots are then placed in a greenhouse at 20°–24° C. for 2–3 weeks. The soil is kept uniformly moist by light spraying with water. The test is evaluated by determining the emergence of the sugar beet plants and the number of healthy and diseased plants.

b) Action following Application by Dressing

The fungus is cultivated on sterile oat grains and added to an earth/sand mixture. The earth so infected is introduced into plant pots and sown with sugar beet seeds which have been dressed with the test compounds formulated as dressing powders (1000 ppm active ingredient, based on the weight of the seeds). The pots containing the seeds are then placed in a greenhouse at 20°–24° C. for 2–3 weeks. The soil is kept uniformly moist by light spraying with water. The test is evaluated by determining the emergence of the sugar beet plants and the number of healthy and diseased plants.

Following treatment with compounds of formula I, over 80% of the plants emerge and have a healthy appearance. In the control pots, only the occasional emerged plant, with a diseased appearance, is observed.

EXAMPLE B-4

Residual-protective Action against *Cercospora arachidicola* on Groundnuts 10 to 15 cm high groundnut plants are sprayed to drip point with an aqueous spray mixture (0.02% active ingredient) and are infected 48 hours later with a conidia suspension of the fungus. The plants are incubated for 72 hours at 21° and high humidity and are then placed in a greenhouse until the typical leaf specks occur. The activity of the test compound is evaluated 12 days after infection and is based on the number and size of the leaf specks. Compounds of formula I bring about a reduction in leaf specks to less than about 10% of the leaf surface. In some cases, the disease is inhibited completely (0–5% infestation).

EXAMPLE B-5

Action against *Puccinia graminis* on Wheat a) Residual-protective Action 6 days after sowing, wheat plants are sprayed to drip point with an aqueous spray mixture (0.02% active ingredient) and are infected 24 hours later with a uredospore suspension of the fungus. After an incubation period of 48 hours (conditions: 95 to 100% relative humidity at 20°), the plants are placed in a greenhouse at 22°. Evaluation of rust pustule development is made 12 days after infection.

b) Systemic Action 5 days after sowing, wheat plants are watered with an aqueous spray mixture (0.006% active ingredient, based on the volume of the soil). Care is taken that the spray mixture does not come into contact with the parts of the plants above the soil. After 48 hours the plants are infected with a uredospore suspension of the fungus. After an incubation period of 48 hours (conditions: 95 to 100% relative humidity at 20°), the plants are placed in a greenhouse at 22°. Evaluation of rust pustule development is made 12 days after infection. Compounds of formula I, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, effect a marked reduction in fungus infestation, in some cases to 10–0%.

EXAMPLE B-6

Action against *Pyricularia oryzae* on Rice a) Residual-protective Action

After a cultivation period of 2 weeks, rice plants are sprayed to drip point with an aqueous spray mixture (0.02% active ingredient) and are infected 48 hours later with a conidia suspension of the fungus. Evaluation of fungus infestation is made 5 days after infection, during which period 95 to 100% relative humidity and a temperature of 22° are maintained.

b) Systemic Action 2-week-old rice plants are watered with an aqueous spray mixture (0.006% active ingredient, based on the volume of the soil). Care is taken that the spray mixture does not come into contact with the parts of the plants above the soil. The pots are then filled with water so that the lowermost parts of the stems of the rice plants stand in water. After 96 hours, the plants are infected with a conidia suspension of the fungus and are kept for 5 days at 95 to 100% relative humidity and a temperature of 24° C.

Compounds of formula I, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, largely prevent the disease from breaking out on the infected plants.

EXAMPLE B-7

Residual-protective Action against *Venturia inaequalis* on Apples

Apple cuttings with 10–20 cm long fresh shoots are sprayed to drip point with a spray mixture (0.02% active ingredient) and are infected 24 hours later with a conidia suspension of the fungus. The plants are incubated for 5 days at 90 to 100% relative humidity and are placed for a further 10 days in a greenhouse at 20° to 24°. Scab infestation is evaluated 15 days after infection.

Compounds of formula I of one of Tables 1 to 10 mainly exhibit sustained activity against scab diseases (less than 10% infestation).

EXAMPLE B-10

Action against *Erysiphe graminis* on Barley a) Residual-protective Action

Barley plants about 8 cm in height are sprayed to drip point with an aqueous spray mixture (0.02% active ingredient) and are dusted 3 to 4 hours later with conidia of the fungus. The infected plants are placed in a greenhouse at 22°. Fungus infestation is evaluated 10 days after infection.

b) Systemic Action

Barley plants about 8 cm in height are watered with an aqueous spray mixture (0.002% active ingredient, based on the volume of the soil). Care is taken that the spray mixture does not come into contact with the parts of the plants above the soil. The plants are dusted 48 hours later with conidia of the fungus. The infected plants are placed in a greenhouse at 22°. Evaluation of fungus infestation is made 10 days after infection.

Compounds of formula I, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, are generally able to reduce disease infestation to less than 20%, and in some cases even completely.

EXAMPLE B-9

Action against *Podosphaera leucotricha* on Apple Shoots

Residual-protective Action

Apple cuttings with about 15 cm long fresh shoots are sprayed with a spray mixture (0.06% active ingredient). After 24 hours, the treated plants are infected with a conidia suspension of the fungus and are placed in a climatic chamber at 70% relative humidity and 20° C. Fungus infestation is evaluated 12 days after infection.

Following treatment with compounds of formula I, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, disease infestation is less than 20%. Control plants exhibit 100% infestation.

EXAMPLE B-10

Action against *Botrytis cinerea* on Apple Fruits

Residual-protective Action

Artificially damaged apples are treated by dropping a spray mixture (0.02% active ingredient) onto the damaged sites. The treated fruits are then inoculated with a spore suspension of the fungus and are incubated for one week at high humidity and about 20° C. The fungicidal activity of the test compound is derived from the number of rotted damaged sites.

The compounds of formula I of Tables 1 to 10, e.g. compounds 1.13, 1.67, 1.74, 1.77, 1.270, 1.273, 1.274, 2.1, 2.27, 2.78, 2.79, 2.85, 3.8, 3.76, 3.269, 3.270, 4.27, 5.13, 6.32, 6.105, 7.58, 8.32 and 9.58, are able to prevent the rot from spreading, in some cases completely.

EXAMPLE B-11

Action against *Helminthosporium gramineum*

Wheat grains are contaminated with a spore suspension of the fungus and are left to dry. The contaminated grains are dressed with a suspension of the test compound (600 ppm active ingredient, based on the weight of the seeds). 2 days later, the grains are placed on suitable agar dishes and, after a further four days, the development of the fungus colonies around the grains is assessed. The evaluation of the test compound is based on the number and size of the fungus colonies.

Some of the compounds of formula I exhibit very good activity, i.e. complete inhibition of the fungus colonies.

EXAMPLE B-12

Action against *Colletotrichum lagenarium* on Cucumbers

After a cultivation period of 2 weeks, cucumber plants are sprayed with a spray mixture (concentration 0.002%). 2 days later, the plants are infected with a spore suspension ($1.5 \times 10^5$ spores/ml) of the fungus and are incubated for 36 hours at 23° C. and high humidity. Incubation is then continued at normal humidity and about 22°–23° C. The fungus infestation that has occurred is evaluated 8 days after infection. Fungus infestation is 100% on untreated and infected control plants.

The compounds of formula I inhibit infestation with the disease in some cases almost completely.

EXAMPLE B-13

Action against *Fusarium nivale* on Rye

Rye of the Tetrahell variety which is naturally infected with *Fusarium nivale* is dressed in a roller mixer with the test fungicide, the following concentrations being used: 20 or 6 ppm a.i. (based on the weight of the seed).

The infected and treated rye is sown in October in the open with a seeder in plots 3 meters long and in 6 rows. Three replicates are carried out with each concentration.

Until evaluation of the infestation is made, the test crop is cultivated under normal field conditions (preferably in a region with unbroken snow cover during the winter months).

In order to evaluate the phytotoxicity, the emergence is assessed in the autumn and the crop density/number of plants per unit area is assessed in the spring.

To determine the effectiveness of the test compounds, the percentage of plants attacked by Fusarium is assessed in the spring directly after the snow has melted. The number of infested plants is less than 5% in the present case. The plants that have emerged have a healthy appearance.

EXAMPLE B-14

Action against *Septoria nodorum* on Wheat

Wheat plants are sprayed in the 3-leaf stage with a spray mixture (60 ppm a.i.) prepared from a wettable powder formulation of the test compounds (2.8:1). 24 hours later, the treated plants are infected with a conidia suspension of the fungus. The plants are then incubated for 2 days at 90–100% relative humidity and are placed in a greenhouse for a further 10 days at 20°–24° C. Fungus infestation is evaluated 13 days after infection. Less than 1% of the wheat plants are infested.

EXAMPLE B-15

Action against *Rhizoctonia solani* on Rice

Protective Local Soil Application

10-day-old rice plants are watered with a suspension (spray mixture) prepared from formulated test compound, without contaminating the parts of the plants above the soil. The plants are infected three days later by placing a barley straw infected with Rhizoctonia solani between the rice plants in each pot. Fungus infestation is evaluated after incubation for 6 days in a climatic chamber at a day temperature of 29° C. and a night temperature of 26° C. and at 95% relative humidity. Less than 5% of the rice plants are infested. The plants have a healthy appearance.

Protective Local Foliar Application

12-day-old rice plants are sprayed with a suspension prepared from formulated test compounds. The plants are infected one day later by placing a barley straw infected with *Rhizoctonia solani* between the rice plants in each pot. Evaluation is made after incubation for 6 days in a climatic chamber at a day temperature of 29° C. and a night temperature of 26° C. and at 95% relative humidity. Infestation is 100% on untreated and infected control plants. The compounds of formula I inhibit disease infestation in some cases almost completely.

What is claimed is:

1. The intermediate of the formula

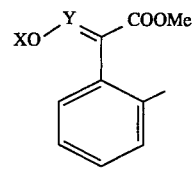

wherein X is $CH_2F$ or $CHF_2$ and Y is CH or N.

2. The intermediate of the formula

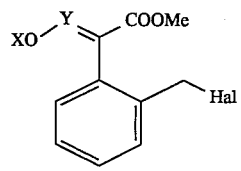

wherein X is $CH_2F$ or $CHF_2$, Y is CH or N, and Hal is chlorine or bromine.

* * * * *